US008394797B2

(12) United States Patent
Corbera Arjona et al.

(10) Patent No.: US 8,394,797 B2
(45) Date of Patent: Mar. 12, 2013

(54) SUBSTITUTED PYRAZOLE SIGMA RECEPTOR ANTAGONISTS

(75) Inventors: Jordi Corbera Arjona, Barcelona (ES); Maria Rosa Cuberes-Altisent, Barcelona (ES); Joerg Holenz, Barcelona (ES); Daniel Martínez-Olmo, Barcelona (ES); David Vaño-Domenech, Barcelona (ES)

(73) Assignee: Laboratorios Del Dr. Esteve, S.A., Barcelona (ES)

( * ) Notice: Subject to any disclaimer, the term of this patent is extended or adjusted under 35 U.S.C. 154(b) by 274 days.

(21) Appl. No.: 12/893,256

(22) Filed: Sep. 29, 2010

(65) Prior Publication Data

US 2011/0015183 A1    Jan. 20, 2011

Related U.S. Application Data

(62) Division of application No. 11/574,364, filed on Apr. 20, 2007, now Pat. No. 7,829,559.

(30) Foreign Application Priority Data

Aug. 27, 2004  (EP) .................................. 04077422
Oct. 14, 2004  (ES) .................................. 200402442

(51) Int. Cl.
*A61K 31/535*    (2006.01)
(52) U.S. Cl. .................. 514/234.5; 514/254.06; 514/32; 548/360.1
(58) Field of Classification Search ............... 514/234.5, 514/254.06, 32; 548/360.1
See application file for complete search history.

(56) References Cited

U.S. PATENT DOCUMENTS

| 4,734,429 | A | 3/1988 | Le Tourneau |
| 7,282,499 | B2 | 10/2007 | Arjona |

FOREIGN PATENT DOCUMENTS

| EP | 0 276 834 | 8/1988 |
| EP | 0 414 289 | 2/1991 |
| EP | 0 431 943 | 6/1991 |
| EP | 0 445 974 | 9/1991 |
| EP | 0 518 805 | 12/1992 |
| JP | 57-165369 A2 | 10/1982 |
| WO | WO 91/09594 | 7/1991 |
| WO | WO96/04287 A1 | 2/1996 |
| WO | WO02/102387 A1 | 12/2002 |
| WO | WO 2006/021463 | 3/2006 |

OTHER PUBLICATIONS

The Merck Manual Home Health Handbook—Autoimmune Disorders—revision Jul. 2007.*
Leslie, Science vol. 327, 1573 (Mar. 26, 2010).*
Lauren Cahoon, Science vol. 322, p. 667-669 (Oct. 31, 2008).*
American Autoimmune Related Diseases Association 2012—http://www.aarda.org/research_display.php?ID=47.*
Refer to Mitch Leslie, Science Now, May 27, 2010—http://news.sciencemag.org/sciencenow/2010/05/ocd-your-immune-system-could-be-.html.*
Kenji Hashimoto, CNS & Neurological Disorders-Drug Target, 8(6); pp. 470-474 (Dec. 2009).*
Dehaven-Hudkins, D., et al., "Characterization of the binding of [$^3$H](+)-pentazocine to σ recognition sites in guinea pig brain," *Eur. J. Pharmacol.*, vol. 227: 371-378, 1992.
Hanner, M., et al., "Purification, molecular cloning, and expression of the mammalian sigma1-binding site," *Proc. Natl. Acad. Sci.*, vol. 93: 8072-8077, Jul. 1996.
Langa, F., et al., "Generation and phenotypic analysis of sigma receptor type I (σ1) knockout mice," *European Journal of Neuroscience*, vol. 18: 2188-2196, 2003.
Lowry, O.H., et al., "Protein Measurement With the Folin Phenol Reagent," *J. Biol. Chem.*, pp. 265-275, 1951.
Mosti, L., et al., "Acetic Acids Bearing the 1-Phenyl-1H-Indazole Nucleus With Analgesic and Antiinflammatory Activity," *IL Farmaco*, vol. 43: 763-774, Oct. 1988.
Peet, N.P., et al, "Synthesis of Angular Benzodipyrazoles and Related Systems," *Heterocycles*, vol. 32, No. 1: 41-72, 1991.
Quirion, R. et al., "A proposal for the classification of sigma binding sites," *Trends Pharmacol. Sci.*, vol. 13: 85-86, 1992.
Radesca, L., et al., "Synthesis and Receptor Binding of Enantiomeric N-Substituted cis-N-[2-(3,4-Dichlorophenyl)ethyl]-2-(1-pyrrolidinyl) cyclohexylamines as High-Affinity σ Receptor Ligands," *J. Med. Chem.*, vol. 34: 3058-3065, 1991.
Schenone, P., et al., "Reaction of 2-Dimethylaminomethylene-1, 3-diones with Dinucleophiles. I. Synthesis of 1, 5-Disubstituted 4-Acylpyrazoles," *Heterocyclic Chem.*, vol. 19: 1355-1361, 1982.
Snyder, S.H., et al., "Receptor Mechanisms in Antipsychotic Drug Action: Focus on Sigma Receptors," *Journal of Neuropsychiatry*, vol. 1: 7-15, 1989.
Trehan, I. R., et al., "Synthesis of 2,3,13-Triaza-18-nor-I7-oxo-3-phenyl-A-nor-estra-I,5(10), 9(II)-triene & 2,3,13-Triaza-7,7-dimethyl-18-nor-17-oxo-3-phenyl-A-nor-estra-I,5(10), 9(II)-triene," *Indian Journal of Chemistry*, vol. 19B: 243-245, Apr. 1980.

(Continued)

*Primary Examiner* — Yong Chu
*Assistant Examiner* — Valerie Rodriguez-Garcia
(74) *Attorney, Agent, or Firm* — Locke Lord LLP

(57) ABSTRACT

The invention relates to compounds having pharmacological activity towards the sigma receptor, and more particularly to pyrazole derivatives of formula I

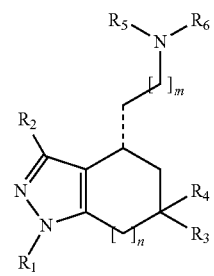

and to processes of preparation of such compounds, to pharmaceutical compositions comprising them, and to their use therapy and prophylaxis, in particular for the treatment of psychosis or pain.

12 Claims, 2 Drawing Sheets

OTHER PUBLICATIONS

Walker, J.M., et al., "Sigma Receptors: Biology and Function," *Pharmacological Reviews*, vol. 42: 355-402, 1990.

European Patent Office, European Search Report for European Application 04077422.6, dated Jan. 21, 2005.

International Search Report for International Application No. PCT/EP2005/009377, mailed Oct. 26, 2005.

Vippagunta, et al. "Crystalline Solids", *Advanced Drug Delivery Reviews*, vol. 48, pp. 3-26, 2001.

Gavezzotti, "Are Crystal Structures Predictable?", *Accounts of Chemical Research*, vol. 27, pp. 309-314, 1994

\* cited by examiner

SUBSTITUTED PYRAZOLE SIGMA RECEPTOR ANTAGONISTS

This application is a divisional of, and claims the benefit to, U.S. application Ser. No. 11/574,364 (now allowed), which claims the benefit of International Application No. PCT/EP2005/009377 filed on Aug. 29, 2005 under 35 U.S.C. §371, which claims benefit of U.S. application Ser. No. 10/977,738, filed on Oct. 29, 2004; Spanish Patent Application No. P200402442, filed on Oct. 14, 2004; and European Patent Application No. 04077422.6, filed on Aug. 27, 2004, which are all incorporated by reference in their entireties.

FIELD OF THE INVENTION

The present invention relates to compounds having pharmacological activity towards the sigma receptor, and more particularly to some pyrazole derivatives, to processes of preparation of such compounds, to pharmaceutical compositions comprising them, and to their use in therapy and prophylaxis, in particular for the treatment of psychosis or pain.

BACKGROUND OF THE INVENTION

The search for new therapeutic agents has been greatly aided in recent years by better understanding of the structure of proteins and other biomolecules associated with target diseases. One important class of these proteins is the sigma receptor, a cell surface receptor of the central nervous system (CNS) which may be related to the dysphoric, hallucinogenic and cardiac stimulant effects of opioids. From studies of the biology and function of sigma receptors, evidence has been presented that sigma receptor ligands may be useful in the treatment of psychosis and movement disorders such as dystonia and tardive dyskinesia, and motor disturbances associated with Huntington's chorea or Tourette's syndrome and in Parkinson's disease (Walker, J. M. et al, *Pharmacological Reviews*, 1990, 42, 355). It has been reported that the known sigma receptor ligand rimcazole clinically shows effects in the treatment of psycosis (Snyder, S. H., Largent, B. L. J. Neuropsychiatry 1989, 1, 7). The sigma binding sites have preferential affinity for the dextrorotatory isomers of certain opiate benzomorphans, such as (+)-SKF 10047, (+)-cyclazocine, and (+)-pentazocine and also for some narcoleptics such as haloperidol. The sigma receptor has at least two subtypes, which may be discriminated by stereoselective isomers of these pharmacoactive drugs. SKF 10047 has nanomolar affinity for the sigma-1 site, and has micromolar affinity for the sigma-2 site. Haloperidol has similar affinities for both subtypes. Endogenous sigma ligands are not known, although progesterone has been suggested to be one of them. Possible sigma-site-mediated drug effects include modulation of glutamate receptor function, neurotransmitter response, neuroprotection, behavior, and cognition (Quirion, R. et al. *Trends Pharmacol. Sci.*, 1992, 13:85-86). Most studies have implied that sigma binding sites (receptors) are plasmalemmal elements of the signal transduction cascade. Drugs reported to be selective sigma ligands have been evaluated as antipsychotics (Hanner, M. et al. *Proc. Natl. Acad. Sci*, 1996, 93:8072-8077). The existence of sigma receptors in the CNS, immune and endocrine systems have suggested a likelihood that it may serve as link between the three systems.

In view of the potential therapeutic applications of agonists or antagonists of the sigma receptor, a great effort has been directed to find selective ligands. Thus, the prior art discloses different sigma receptor ligands.

International Patent Application No. WO 91/09594 generically describes a broad class of sigma receptor ligands some of which are 4-phenylpiperidine, -tetrahydro-pyridine or -piperazine compounds having an optionally substituted aryl or heteroaryl, alkyl, alkenyl, alkynyl, alkoxy or alkoxyalkyl substituent on the ring N-atom. The terms aryl and heteroaryl are defined by mention of a number of such substituents.

European patent publication No. EP 0 414 289 A1 generically discloses a class of 1,2,3,4-tetrahydro-spiro[naphthalene-1,4'-piperidine] and 1,4-dihydro-spiro [naphthalene-1, 4'-piperidine] derivatives substituted at the piperidine N-atom with a hydrocarbon group alleged to have selective sigma receptor antagonistic activity. The term hydrocarbon, as defined in said patent, covers all possible straight chained, cyclic, heterocyclic, etc. groups. However, only compounds having benzyl, phenethyl, cycloalkylmethyl, furyl- or thienylmethyl or lower alkyl or alkenyl as the hydrocarbon substituent at the piperidine nitrogen atom are specifically disclosed. The compounds are stated to displace tritiated di-tolyl guanidine (DTG) from sigma sites with potencies better than 200 nM. As a particularly preferred compound is mentioned 1'-benzyl-1,2,3,4-tetrahydro-spiro[naphthalene-1,4'-piperidine].

European patent publication No. EP 0 445 974 A2 generically describes the corresponding spiro[indane-1,4'-piperidine] and spiro[benzocycloheptene-5,4'-piperidine] derivatives. Again the compounds are only stated to displace tritiated di-tolyl guanidine (DTG) from sigma sites with potencies better than 200 nM European patent Application No. EP 0 431 943 A2 relates to a further extremely broad class of spiropiperidine compounds substituted at the piperidine N-atom and claimed to be useful as antiarrhythmics and for impaired cardiac pump function. The said application exemplifies several compounds, the majority of which contain an oxo and/or a sulfonylamino substituent in the Spiro cyclic ring system. Of the remainder compounds, the main part has another polar substituent attached to the Spiro nucleus and/or they have some polar substituents in the substituent on the piperidine N-atom. No suggestion or indication of effect of the compounds on the sigma receptor is given.

There is still a need to find compounds that have pharmacological activity towards the sigma receptor, being both effective and selective, and having good "drugability" properties, i.e. good pharmaceutical properties related to administration, distribution, metabolism and excretion.

SUMMARY OF THE INVENTION

We have now found a family of pyrazol derivatives which are particularly selective inhibitors of the sigma receptor. The compounds present a pyrazol group which is condensed with a cycloalkyl ring having 5, 6 or 7 carbon atoms.

In one aspect the invention is directed to a compound of the formula I:

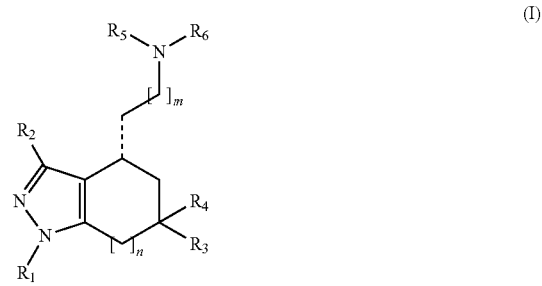

wherein
- R$_1$ is selected from the group formed by hydrogen, substituted or unsubstituted alkyl, substituted or unsubstituted cycloalkyl, substituted or unsubstituted heterocyclyl, substituted or unsubstituted aryl, substituted or unsubstituted arylalkyl, and substituted or unsubstituted heterocyclylalkyl;
- R$_2$ is selected from the group formed by hydrogen, substituted or unsubstituted alkyl, substituted or unsubstituted cycloalkyl, substituted or unsubstituted alkoxy, substituted or unsubstituted aryl, substituted or unsubstituted heterocyclyl, substituted or unsubstituted arylalkyl, and substituted or unsubstituted heterocyclylalkyl;
- R$_3$ and R$_4$ are independently selected from the group formed by hydrogen, substituted or unsubstituted alkyl, substituted or unsubstituted cycloalkyl, substituted or unsubstituted heterocyclyl, substituted or unsubstituted aryl, substituted or unsubstituted arylalkyl and substituted or unsubstituted heterocyclylalkyl or, together, R$_3$ and R$_4$ form a 3 to 6 substituted or unsubstituted member ring;
- R$_5$ and R$_6$ are independently selected from the group formed by hydrogen, substituted or unsubstituted alkyl, substituted or unsubstituted cycloalkyl, substituted or unsubstituted heterocyclyl, substituted or unsubstituted aryl, substituted or unsubstituted arylalkyl and substituted or unsubstituted heterocyclylalkyl or, R$_5$ and R$_6$ together, form a substituted or unsubstituted heterocyclyl having 3 to 7 atoms in the ring;
- n is selected from 0, 1 and 2;
- m is selected from 0, 1, 2, 3 and 4;
- the dotted line ----- is either a single or a double bond;

with the proviso that when R$_1$ is phenyl, R$_2$ is H, the dotted line ----- is a double bond, m is 1, and R$_5$ and R$_6$ form a 2,5-dioxopyrrolidine or a 5-ethoxy-2-oxo-pyrrolidine; then R$_3$ and R$_4$ are not both at the same time H or methyl;
or a pharmaceutically acceptable salt, isomer, prodrug or solvate thereof.

In one embodiment R$_2$ is preferably hydrogen or alkyl; more preferably hydrogen. It is also preferred that m is 1 or 2, and also that n is 0 or 1. Moreover, it is also preferred that R$_3$ and R$_4$ are both hydrogen or alkyl; more preferred both hydrogen or methyl; and most preferred both hydrogen. Further, it is preferred that R$_1$ is selected from the group formed by substituted or unsubstituted alkyl, substituted or unsubstituted cycloalkyl, substituted or unsubstituted heterocyclyl and substituted or unsubstituted aryl; more preferred substituted or unsubstituted alkyl, unsubstituted cycloalkyl, unsubstituted aryl and aromatic heterocyclic; and most preferred, methyl, t-butyl, cyclohexyl and phenyl. Moreover, it is also preferred that R$_5$ and R$_6$ together form a substituted or unsubstituted heterocyclyl having 3 to 7 atoms in the ring, in particular morpholin-4-yl, 2,6-dimethylmorpholin-4-yl, piperidin-1-yl, 4-phenylpiperidin-1-yl, 3-phenylpiperidin-1-yl, 4-benzylpiperazin-1-yl, 4-phenyl-piperazin-1-yl, 2-[spiro[isobenzofuran-1(3H),4'-piperidin]-1'-yl, azepan-1-yl, 1,2,3,4-tetrahydro-isoquinolin-2-yl, pyrrolidin-1-yl, 3-phenyl-pyrrolidin-1-yl, isoindolin-2-yl or imidazol-1-yl; especially when R$_2$ is hydrogen, m is 1 and n is 1; more especially when R$_3$ and R$_4$ are both hydrogen; and even more especially when R$_1$ is substituted or unsubstituted phenyl. Good results are obtained when R$_5$ is benzyl and R$_6$ is methyl.

The above embodiments and preferences for R$_1$ to R$_6$, n, m and the dotted line ----- can be combined to give further preferred compounds.

In another aspect the invention is directed to processes for the preparation of compounds of formula (I) or a salt, isomer or solvate thereof.

In another aspect the invention is directed to a pharmaceutical composition which comprises a compound as above defined or a pharmaceutically acceptable salt, enantiomer, prodrug or solvate thereof, and a pharmaceutically acceptable carrier, adjuvant or vehicle.

In a further aspect the invention is directed to the use of a compound as defined above in the manufacture of a medicament for the treatment of a sigma mediated disease or condition, i.e. diarrhoea, lipoprotein disorders, hyperlipidemia, hypertriglyceridemia, hypercholesterolemia, obesity, migraine, arthritis, hypertension, arrhythmia, ulcer, glaucoma, learning, memory and attention deficits, cognition disorders, neurodegenerative diseases, demyelinating diseases, addiction to drugs and chemical substances including cocaine, amphetamine, ethanol and nicotine; tardive diskinesia, ischemic stroke, epilepsy, stroke, stress, cancer, psychotic conditions, in particular depression, anxiety or schizophrenia; inflammation, autoimmune diseases or use as pharmacological tool or as anxiolytic or immunosuppressant.

DETAILED DESCRIPTION OF THE INVENTION

Figure 1:
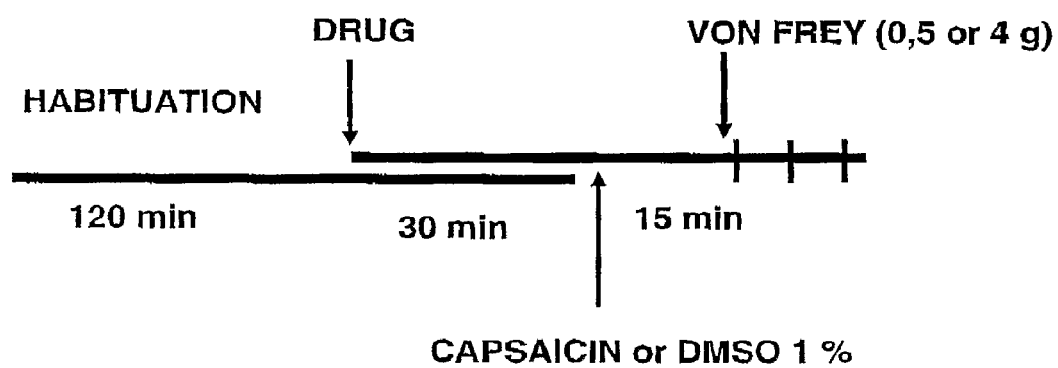
FIG. 1 shows the test protocol for all tests with von Frey filaments.

The typical compounds of this invention effectively and selectively inhibit the sigma receptor. In the above definition of compounds of formula (I) the following terms have the meaning indicated:

"Alkyl" refers to a straight or branched hydrocarbon chain radical consisting of carbon and hydrogen atoms, containing no unsaturation, having 1 to 8 carbon atoms, and which is attached to the rest of the molecule by a single bond, e.g., methyl, ethyl, n-propyl, i-propyl, n-butyl, t-butyl, n-pentyl, etc. Alkyl radicals may be optionally substituted by one or more substituents such as aryl, halo, hydroxy, alkoxy, carboxy, cyano, carbonyl, acyl, alkoxycarbonyl, amino, nitro, mercapto, alkylthio, etc. If substituted by aryl we have an "Aralkyl" radical, such as benzyl and phenethyl.

"Alkenyl" refers to an alkyl radical having at least 2 carbon atoms and having one or more unsaturated bonds.

"Cycloalkyl" refers to a stable 3- to 10-membered monocyclic or bicyclic radical which is saturated or partially saturated, and which consists solely of carbon and hydrogen atoms, such as cyclohexyl or adamantyl. Unless otherwise stated specifically in the specification, the term "cycloalkyl" is meant to include cycloalkyl radicals which are optionally substituted by one or more substituents such as alkyl, halo, hydroxy, amino, cyano, nitro, alkoxy, carboxy, alkoxycarbonyl, etc.

"Aryl" refers to single and multiple ring radicals, including multiple ring radicals that contain separate and/or fused aryl groups. Typical aryl groups contain from 1 to 3 separated or fused rings and from 6 to about 18 carbon ring atoms, such as phenyl, naphthyl, indenyl, phenanthryl or anthryl radical. The aryl radical may be optionally substituted by one or more substituents such as hydroxy, mercapto, halo, alkyl, phenyl, alkoxy, haloalkyl, nitro, cyano, dialkylamino, aminoalkyl, acyl, alkoxycarbonyl, etc.

"Heterocyclyl" refers to a stable 3- to 15 membered ring radical, aromatic or not, which consists of carbon atoms and from one to five heteroatoms selected from the group consisting of nitrogen, oxygen, and sulfur, preferably a 4- to 8-membered ring with one or more heteroatoms, more preferably a 5- or 6-membered ring with one or more heteroatoms. For the purposes of this invention, the heterocycle may be aromatic, saturated or partially saturated, and also a monocyclic, bicyclic or tricyclic ring system, which may include fused ring systems; and the nitrogen, carbon or sulfur atoms in the heterocyclyl radical may be optionally oxidised; the nitrogen atom may be optionally quaternized; and the heterocyclyl radical may be partially or fully saturated or aromatic. Examples of such heterocycles include, but are not limited to, azepines, benzimidazole, benzothiazole, furan, isothiazole, imidazole, indole, piperidine, piperazine, purine, quinoline, thiadiazole, tetrahydrofuran, coumarine, morpholine; pyrrole, pyrazole, oxazole, isoxazole, triazole, imidazole, etc. Unless otherwise stated specifically in the specification, the term "heterocyclyl" is meant to include heterocyclyl radicals which are optionally substituted by one or more substituents such as hydroxy, mercapto, halo, alkyl, phenyl, alkoxy, haloalkyl, nitro, cyano, dialkylamino, aminoalkyl, acyl, alkoxycarbonyl, sulfonyl, sulfonylamino, alkyl or arylsulfonylamino, alkylarylsulfonilamino, acylamino, acetamido, etc.

"Alkoxy" refers to a radical of the formula —ORa where Ra is an alkyl radical as defined above, e.g., methoxy, ethoxy, propoxy, etc.

"Alkoxycarbonyl" refers to a radical of the formula —C(O)ORa where Ra is an alkyl radical as defined above, e.g., methoxycarbonyl, ethoxycarbonyl, propoxycarbonyl, etc.

"Alkylthio" refers to a radical of the formula-SRa where Ra is an alkyl radical as defined above, e.g., methylthio, ethylthio, propylthio, etc.

"Amino" refers to a radical of the formula-$NH_2$, —NHRa or —NRaRb, optionally quaternized, wherein Ra and Rb are, independently, an alkyl radical as defined above, e.g., methylamino, ethylamino, dimethylamino, diethylamino, propylamino, etc.

"Halo" or "hal" refers to bromo, chloro, iodo or fluoro.

References herein to substituted groups in the compounds of the present invention refer to the specified moiety that may be substituted at one or more available positions by one or more suitable groups, e.g., halogen such as fluoro, chloro, bromo and iodo; cyano; hydroxyl; nitro; azido; alkanoyl such as a C1-6 alkanoyl group such as acyl and the like; carboxamido; alkyl groups including those groups having 1 to about 12 carbon atoms or from 1 to about 6 carbon atoms and more preferably 1-3 carbon atoms; alkenyl and alkynyl groups including groups having one or more unsaturated linkages and from 2 to about 12 carbon or from 2 to about 6 carbon atoms; alkoxy groups having one or more oxygen linkages and from 1 to about 12 carbon atoms or 1 to about 6 carbon atoms; aryloxy such as phenoxy; alkylthio groups including those moieties having one or more thioether linkages and from 1 to about 12 carbon atoms or from 1 to about 6 carbon atoms; alkylsulfinyl groups including those moieties having one or more sulfinyl linkages and from 1 to about 12 carbon atoms or from 1 to about 6 carbon atoms; alkylsulfonyl groups including those moieties having one or more sulfonyl linkages and from 1 to about 12 carbon atoms or from 1 to about 6 carbon atoms; aminoalkyl groups such as groups having one or more N atoms and from 1 to about 12 carbon atoms or from 1 to about 6 carbon atoms; carbocyclic aryl having 6 or more carbons, particularly phenyl or naphthyl and aralkyl such as benzyl. Unless otherwise indicated, an optionally substituted group may have a substituent at each substitutable position of the group, and each substitution is independent of the other.

The present invention does not include the synthesis intermediate disclosed in EP 276 834 A corresponding to the compound of general formula I in which $R_1$ is methyl, $R_3=R_4=R_2=H$, $R_5=R_6=$methyl, n=2, m=0 and the dotted line is a double bond. The present invention does not include either the synthesis intermediates disclosed in *Indian Journal of Chemistry*, Section B, 1980, 19b, 243-45 corresponding to certain compounds of general formula I in which $R_5$ and $R_6$ form together a 5-ethoxy,2-oxopirrolidin or a 5,2-dioxopirrolidin group.

Particular individual compounds of the invention falling under formula (I) include the compounds listed below:

1. 4,5,6,7-tetrahydro-4-(2-(morpholin-4-yl)ethyl)-1-phenyl-1H-indazole,
2. 4,5,6,7-tetrahydro-4-(2-(morpholin-4-yl)ethyl)-1-phenyl-1H-indazole oxalate,
3. 1-(3,4-dichlorophenyl)-4,5,6,7-tetrahydro-4-(2-(4-phenylpiperidin-1-yl)ethyl)-1H-indazole,
4. 1-(3,4-dichlorophenyl)-4,5,6,7-tetrahydro-4-(2-(4-phenylpiperidin-1-yl)ethyl)-1H-indazole oxalate,
5. (E)-4,5,6,7-tetrahydro-4-(2-(morpholin-4-yl)ethylidene)-1-phenyl-1H-indazole,
6. 1-(3,4-dichlorophenyl)-4,5,6,7-tetrahydro-4-(2-(morpholin-4-yl)ethyl)-1H-indazole,
7. 1-(3,4-dichlorophenyl)-4,5,6,7-tetrahydro-4-(2-(morpholin-4-yl)ethyl)-1H-indazole oxalate,
8. 4,5,6,7-tetrahydro-1-phenyl-4-(2-(4-phenylpiperidin-1-yl)ethyl)-1H-indazole,
9. 4,5,6,7-tetrahydro-1-phenyl-4-(2-(4-phenylpiperidin-1-yl)ethyl)-1H-indazole oxalate,
10. 4-(2-(4-benzylpiperazin-1-yl)ethyl)-4,5,6,7-tetrahydro-1-phenyl-1H-indazole,
11. 4,5,6,7-tetrahydro-1-phenyl-4-(2-[spiro[isobenzofuran-1 (3H), 4'-piperidin]-1'-yl]ethyl)-1H-indazole,
12. 4,5,6,7-tetrahydro-1-phenyl-4-(2-[spiro[isobenzofuran-1 (3H), 4'-piperidin]-1'-yl]ethyl)-1H-indazole oxalate,
13. 4,5,6,7-tetrahydro-1-phenyl-4-(2-(piperidin-1-yl)ethyl)-1H-indazole,
14. 4,5,6,7-tetrahydro-1-phenyl-4-(2-(piperidin-1-yl)ethyl)-1H-indazole oxalate,
15. (E)-4-(2-(azepan-1-yl)ethylidene)-4,5,6,7-tetrahydro-1-phenyl-1H-indazole,
16. (E)-4-(2-(azepan-1-yl)ethylidene)-4,5,6,7-tetrahydro-1-phenyl-1H-indazole oxalate,
17. (E)-4,5,6,7-tetrahydro-1-phenyl-4-(2-(4-phenylpiperidin-1-yl)ethylidene)-1H-indazole,
18. (E)-4,5,6,7-tetrahydro-1-phenyl-4-(2-[spiro[isobenzofuran-1(3H), 4'-piperidin]-1'-yl]ethylidene)-1H-indazole,
19. (E)-4,5,6,7-tetrahydro-1-phenyl-4-(2-[spiro[isobenzofuran-1 (3H),4'-piperidin]-1'-yl]ethylidene)-1H-indazole oxalate,
20. (E)-4,5,6,7-tetrahydro-1-phenyl-4-(2-(4-phenylpiperazin-1-yl)ethylidene)-1H-indazole,
21. 1,2,3,4-tetrahydro-2-((E)-2-(6,7-dihydro-1-phenyl-1H-indazol-4(5H)-ylidene)ethyl)isoquinoline,
22. 1,2,3,4-tetrahydro-2-((E)-2-(6,7-dihydro-1-phenyl-1H-indazol-4(5H)-ylidene)ethyl)isoquinoline oxalate,
23. (E)-4,5,6,7-tetrahydro-1-phenyl-4-(2-(3-phenylpiperidin-1-yl)ethylidene)-1H-indazole,
24. (E)-4,5,6,7-tetrahydro-1-phenyl-4-(2-(3-phenylpyrrolidin-1-yl)ethylidene)-1H-indazole 25. (E)-4,5,6,7-tetrahydro-1-phenyl-4-(2-(3-phenylpyrrolidin-1-yl)ethylidene)-1H-indazole oxalate,
26. (E)-4,5,6,7-tetrahydro-4-(2-(isoindolin-2-yl)ethylidene)-1-phenyl-1H-indazole,
27. (E)-4,5,6,7-tetrahydro-1-phenyl-4-(2-(piperidin-1-yl)ethylidene)-1H-indazole,
28. 1-(3,4-dichlorophenyl)-4,5,6,7-tetrahydro-4-(2-(4-phenylpiperazin-1-yl)ethyl)-1H-indazole,
29. 1-(3,4-dichlorophenyl)-4,5,6,7-tetrahydro-4-(2-(4-phenylpiperazin-1-yl)ethyl)-1H-indazole oxalate,
30. 1,4,5,6-tetrahydro-4-(2-(morpholin-4-yl)ethyl)-1-phenylcyclopenta[c]pyrazole,
31. 1,4,5,6-tetrahydro-4-(2-(morpholin-4-yl)ethyl)-1-phenylcyclopenta[c]pyrazole oxalate,
32. 4,5,6,7-tetrahydro-1-phenyl-4-(2-(4-phenylpiperazin-1-yl)ethyl)-1H-indazole,
33. 4,5,6,7-tetrahydro-1-phenyl-4-(2-(4-phenylpiperazin-1-yl)ethyl)-1H-indazole oxalate,
34. 2-(2-(1,4,5,6-tetrahydro-1-phenylcyclopenta[c]pyrazol-4-yl)ethyl)isoindoline,
35. 2-(2-(1,4,5,6-tetrahydro-1-phenylcyclopenta[c]pyrazol-4-yl)ethyl)isoindoline oxalate,
36. 1,4,5,6-tetrahydro-1-phenyl-4-(2-(4-phenylpiperidin-1-yl)ethyl)cyclopenta[c]pyrazole,
37. 1,4,5,6-tetrahydro-1-phenyl-4-(2-(piperidin-1-yl)ethyl)cyclopenta[c]pyrazole,
38. 1,4,5,6-tetrahydro-1-phenyl-4-(2-(4-phenylpiperazin-1-yl)ethyl)cyclopenta[c]pyrazole,
39. 1,4,5,6-tetrahydro-1-phenyl-4-(2-(pyrrolidin-1-yl)ethyl)cyclopenta[c]pyrazole,
40. 1,4,5,6-tetrahydro-1-phenyl-4-(2-(pyrrolidin-1-yl)ethyl)cyclopenta[c]pyrazole oxalate,
41. 4-(2-(4-benzylpiperazin-1-yl)ethyl)-1,4,5,6-tetrahydro-1-phenylcyclopenta[c]pyrazole,
42. 4-(2-(4-benzylpiperazin-1-yl)ethyl)-1,4,5,6-tetrahydro-1-phenylcyclopenta[c]pyrazole dioxalate,
43. 1,2,3,4-tetrahydro-2-(2-(1,4,5,6-tetrahydro-1-phenylcyclopenta[c]pyrazol-4-yl)ethyl)isoquinoline,
44. 1,2,3,4-tetrahydro-2-(2-(1,4,5,6-tetrahydro-1-phenylcyclopenta[c]pyrazol-4-yl)ethyl)isoquinoline oxalate,
45. 4-(2-(1H-imidazol-1-yl)ethyl)-1,4,5,6-tetrahydro-1-phenylcyclopenta[c]pyrazole,
46. cis-1,4,5,6-tetrahydro-4-(2-(2,6-dimethylmorpholin-4-yl)ethyl)-1-phenylcyclopenta[c]pyrazole,
47. cis-1,4,5,6-tetrahydro-4-(2-(2,6-dimethylmorpholin-4-yl)ethyl)-1-phenylcyclopenta[c]pyrazole oxalate,
48. cis-4,5,6,7-tetrahydro-4-(2-(2,6-dimethylmorpholin-4-yl)ethyl)-1-phenyl-1H-indazole,
49. cis-4,5,6,7-tetrahydro-4-(2-(2,6-dimethylmorpholin-4-yl)ethyl)-1-phenyl-1H-indazole oxalate,
50. 1,4,5,6-tetrahydro-1-phenyl-4-(2-[spiro[isobenzofuran-1(3H), 4'-piperidin]-1'-yl]-ethyl)cyclopenta[c]pyrazole,
51. 1,4,5,6-tetrahydro-1-phenyl-4-(2-[spiro[isobenzofuran-1(3H), 4'-piperidin]-1'-yl]-ethyl)cyclopenta[c]pyrazole oxalate,
52. N-benzyl-2-(1,4,5,6-tetrahydro-1-phenylcyclopenta[c]pyrazol-4-yl)-N-methyl-ethanamine,
53. diastereomeric mixture of 1,4,5,6-tetrahydro-1-phenyl-4-(2-(3-phenylpiperidin-1-yl)ethyl)cyclopenta[c]pyrazole,
54. N-benzyl-2-(4,5,6,7-tetrahydro-1-phenyl-1H-indazol-4-yl)-N-methylethanamine,
55. 4,5,6,7-tetrahydro-4-(2-(isoindolin-2-yl)ethyl)-1-phenyl-1H-indazole,
56. 4,5,6,7-tetrahydro-4-(2-(isoindolin-2-yl)ethyl)-1-phenyl-1H-indazole oxalate,
57. 4,5,6,7-tetrahydro-1-methyl-4-(2-(4-phenylpiperidin-1-yl)ethyl)-1H-indazole,
58. 4,5,6,7-tetrahydro-1-methyl-4-(2-(4-phenylpiperidin-1-yl)ethyl)-1H-indazole oxalate,
59. 4,5,6,7-tetrahydro-4-(2-(isoindolin-2-yl)ethyl)-1-methyl-1H-indazole,
60. 4,5,6,7-tetrahydro-4-(2-(isoindolin-2-yl)ethyl)-1-methyl-1H-indazole oxalate,
61. N-benzyl-2-(4,5,6,7-tetrahydro-1-methyl-1H-indazol-4-yl)-N-methylethanamine,
62. N-benzyl-2-(4,5,6,7-tetrahydro-1-methyl-1H-indazol-4-yl)-N-methylethanamine oxalate,
63. 4,5,6,7-tetrahydro-1-methyl-4-(2-(morpholin-4-yl)ethyl)-1H-indazole,
64. 4,5,6,7-tetrahydro-1-methyl-4-(2-(morpholin-4-yl)ethyl)-1H-indazole oxalate,
65. 1-(4-fluorophenyl)-4,5,6,7-tetrahydro-4-(2-(morpholin-4-yl)ethyl)-1H-indazole,
66. 1-(4-fluorophenyl)-4,5,6,7-tetrahydro-4-(2-(morpholin-4-yl)ethyl)-1H-indazole oxalate,
67. cis-1-(4-fluorophenyl)-4,5,6,7-tetrahydro-4-(2-(2,6-dimethylmorpholin-4-yl)ethyl)-1H-indazole,
68. cis-1-(4-fluorophenyl)-4,5,6,7-tetrahydro-4-(2-(2,6-dimethylmorpholin-4-yl)ethyl)-1H-indazole oxalate,
69. N-benzyl-2-(1-(4-fluorophenyl)-4,5,6,7-tetrahydro-1H-indazol-4-yl)-N-methyl-ethanamine,
70. 1-(4-fluorophenyl)-4,5,6,7-tetrahydro-4-(2-(isoindolin-2-yl)ethyl)-1H-indazole,
71. 1-(4-fluorophenyl)-4,5,6,7-tetrahydro-4-(2-(isoindolin-2-yl)ethyl)-1H-indazole oxalate,
72. 1-(4-fluorophenyl)-4,5,6,7-tetrahydro-4-(2-(4-phenylpiperidin-1-yl)ethyl)-1H-indazole,
73. (+)-4,5,6,7-tetrahydro-4-(2-(morpholin-4-yl)ethyl)-1-phenyl-1H-indazole,
74. (+)-4,5,6,7-tetrahydro-4-(2-(morpholin-4-yl)ethyl)-1-phenyl-1H-indazole oxalate,
75. (−)-4,5,6,7-tetrahydro-4-(2-(morpholin-4-yl)ethyl)-1-phenyl-1H-indazole,
76. (−)-4,5,6,7-tetrahydro-4-(2-(morpholin-4-yl)ethyl)-1-phenyl-1H-indazole oxalate,
77. (E)-4,5,6,7-tetrahydro-4-(2-(morpholin-4-yl)ethylidene)-1-phenyl-1H-indazole oxalate
78. (E)-4,5,6,7-tetrahydro-1-phenyl-4-(2-(piperidin-1-yl)ethylidene)-1H-indazole oxalate,
79. (E)-N-benzyl-2-(6,7-dihydro-1-phenyl-1H-indazol-4(5H)-ylidene)-N-methyl-ethanamine,
80. (E)-N-benzyl-2-(6,7-dihydro-1-phenyl-1H-indazol-4(5H)-ylidene)-N-methyl-ethanamine oxalate,
81. (E)-4,5,6,7-tetrahydro-4-(2-(cis-2,6-dimethylmorpholin-4-yl)ethylidene)-1-phenyl-1H-indazole,
82. (E)-4,5,6,7-tetrahydro-4-(2-(cis-2,6-dimethylmorpholin-4-yl)ethylidene)-1-phenyl-1H-indazole oxalate.
83. (E)-1-(3,4-dichlorophenyl)-4,5,6,7-tetrahydro-4-(2-(cis-2,6-dimethylmorpholino-4-yl)-ethylidene)-1H-indazole
84. (E)-1-(3,4-dichlorophenyl)-4,5,6,7-tetrahydro-4-(2-(cis-2,6-dimethyl-morpholino-4-yl)ethylidene)-1H-indazole oxalate
85. (E)-1-(3,4-dichlorophenyl)-4,5,6,7-tetrahydro-4-(2-(morpholino-4-yl)ethylidene)-1H-indazole
86. (E)-1-(3,4-dichlorophenyl)-4,5,6,7-tetrahydro-4-(2-(morpholino-4-yl)-ethylidene)-1H-indazole oxalate
87. (E)-1-(3,4-dichlorophenyl)-4,5,6,7-tetrahydro-4-(2-(piperidin-1-yl)-ethylidene)-1H-indazole
88. (E)-1-(3,4-dichlorophenyl)-4,5,6,7-tetrahydro-4-(2-(piperidin-1-yl)-ethylidene)-1H-indazole oxalate
89. (E)-4-(2-(N,N-diethylamino)ethylidene)-4,5,6,7-tetrahydro-1-phenyl-1H-indazole
90. (E)-4-(2-(N,N-diethylamino)ethylidene)-4,5,6,7-tetrahydro-1-phenyl-1H-indazole oxalate 91. (E)-4-(2-(4-cyclohexylpiperazin-1-yl)ethylidene)-4,5,6,7-tetrahydro-1-phenyl-1H-indazole
92. (E)-4,5,6,7-tetrahydro-4-(2-(4-methylpiperidin-1-yl)ethylidene)-1-phenyl-1H-indazole
93. 4,5,6,7-tetrahydro-4-(2-(4-methylpiperidin-1-yl)ethyl)-1-phenyl-1H-indazole
94. 4,5,6,7-tetrahydro-4-(2-(4-methylpiperidin-1-yl)ethyl)-1-phenyl-1H-indazole oxalate
95. 1,4,5,6-tetrahydro-1-phenyl-4-(2-(piperidin-1-yl)ethyl)cyclopenta[c]pyrazole oxalate
96. 1,4,5,6-tetrahydro-1-phenyl-4-[2-(thiomorpholin-4-yl)ethyl]cyclopenta[c]pyrazole
97. 1,4,5,6-tetrahydro-1-phenyl-4-[2-(thiomorpholin-4-yl)ethyl]cyclopenta[c]pyrazole oxalate
98. 1,4,5,6-tetrahydro-4-(2-(4-methylpiperidin-1-yl)ethyl)-1-phenylcyclopenta[c]pyrazole
99. 1,4,5,6-tetrahydro-4-(2-(4-methylpiperidin-1-yl)ethyl)-1-phenylcyclopenta[c]pyrazole oxalate
100. 1,4,5,6-tetrahydro-4-(2-(4-methylpiperazin-1-yl)ethyl)-1-phenylcyclopenta[c]pyrazole
101. 4-(2-(4-cyclohexylpiperazin-1-yl)ethyl)-1,4,5,6-tetrahydro-1-phenylcyclopenta[c]pyrazole
102. 4-(2-(azepan-1-yl)ethyl)-4,5,6,7-tetrahydro-1-phenyl-1H-indazole
103. N-benzyl-2-(1-tert-butyl-4,5,6,7-tetrahydro-1H-indazol-4-yl)-N-methylethanamine
104. 1-tert-butyl-4,5,6,7-tetrahydro-4-(2-(4-phenylpiperidin-1-yl)ethyl)-1H-indazole
105. 1-tert-butyl-4,5,6,7-tetrahydro-4-(2-(4-phenylpiperidin-1-yl)ethyl)-1H-indazole oxalate
106. (−)-N-bencyl-2-(4,5,6,7-tetrahydro-1-methyl-1H-indazol-4-yl)-N-methylethanamine
107. (+)-N-bencyl-2-(4,5,6,7-tetrahydro-1-methyl-1H-indazol-4-yl)-N-methylethanamine
108. N-(2-(4,5,6,7-tetrahydro-1-methyl-1H-indazol-4-yl)ethyl)-N-methylcyclohexanamine
109. 4,5,6,7-tetrahydro-4-(2-(4-hydroxy-4-phenylpiperidin-1-yl)ethyl)-1-methyl-1H-indazole
110. 4,5,6,7-tetrahydro-1-methyl-4-(2-(4-phenylpiperidin-1-yl)ethyl)-1H-indazole
111. N-benzyl-2-(4,5,6,7-tetrahydro-1-methyl-1H-indazol-4-yl)-N-methylethanamine
112. 4,5,6,7-tetrahydro-1-methyl-4-(2-[spiro[isobenzofuran-1(3H), 4'-piperidin]-1'-yl]-ethyl)-1H-indazole Although the oxalates are listed, other pharmaceutically acceptable salts also form part of this group of preferred compounds.

Unless otherwise stated, the compounds of the invention are also meant to include compounds which differ only in the presence of one or more isotopically enriched atoms. For example, compounds having the present structures except for the replacement of a hydrogen by a deuterium or tritium, or the replacement of a carbon by a $^{13}C$— or $^{14}C$— enriched carbon or $^{15}N$-enriched nitrogen are within the scope of this invention.

The term "pharmaceutically acceptable salts, solvates, prodrugs" refers to any pharmaceutically acceptable salt, ester, solvate, or any other compound which, upon administration to the recipient is capable of providing (directly or indirectly) a compound as described herein. However, it will be appreciated that non-pharmaceutically acceptable salts also fall within the scope of the invention since those may be useful in the preparation of pharmaceutically acceptable salts. The preparation of salts, prodrugs and derivatives can be carried out by methods known in the art.

For instance, pharmaceutically acceptable salts of compounds provided herein are synthesized from the parent compound which contains a basic or acidic moiety by conventional chemical methods. Generally, such salts are, for example, prepared by reacting the free acid or base forms of these compounds with a stoichiometric amount of the appropriate base or acid in water or in an organic solvent or in a mixture of the two. Generally, nonaqueous media like ether, ethyl acetate, ethanol, isopropanol, acetone or acetonitrile are preferred. Examples of the acid addition salts include mineral acid addition salts such as, for example, hydrochloride, hydrobromide, hydroiodide, sulphate, nitrate, phosphate, and organic acid addition salts such as, for example, acetate, maleate, fumarate, citrate, oxalate, succinate, tartrate, malate, mandelate, methanesulphonate and p-toluenesulphonate. Examples of the alkali addition salts include inorganic salts such as, for example, sodium, potassium, calcium, ammonium, magnesium, aluminium and lithium salts, and organic alkali salts such as, for example, ethylenediamine, ethanolamine, N,N-dialkylenethanolamine, triethanolamine, glucamine and basic aminoacids salts.

Particularly favored derivatives or prodrugs are those that increase the bioavailability of the compounds of this invention when such compounds are administered to a patient (e.g., by allowing an orally administered compound to be more readily absorbed into the blood) or which enhance delivery of the parent compound to a biological compartment (e.g., the brain or lymphatic system) relative to the parent species.

Any compound that is a prodrug of a compound of formula (I) is within the scope of the invention. The term "prodrug" is used in its broadest sense and encompasses those derivatives that are converted in vivo to the compounds of the invention. Such derivatives would readily occur to those skilled in the art, and include, depending on the functional groups present in the molecule and without limitation, the following derivatives of the present compounds: esters, amino acid esters, phosphate esters, metal salts sulfonate esters, carbamates, and amides. Examples of well known methods of producing a prodrug of a given acting compound are known to those skilled in the art and can be found e.g. in Krogsgaard-Larsen et al. "Textbook of Drug design and Discovery" Taylor & Francis (april 2002).

The compounds of the invention may be in crystalline form either as free compounds or as solvates and it is intended that both forms are within the scope of the present invention. Methods of solvation are generally known within the art. Suitable solvates are pharmaceutically acceptable solvates. In a particular embodiment the solvate is a hydrate.

The compounds of formula (I) or their salts or solvates are preferably in pharmaceutically acceptable or substantially pure form. By pharmaceutically acceptable form is meant, inter alia, having a pharmaceutically acceptable level of purity excluding normal pharmaceutical additives such as diluents and carriers, and including no material considered toxic at normal dosage levels. Purity levels for the drug substance are preferably above 50%, more preferably above 70%, most preferably above 90%. In a preferred embodiment it is above 95% of the compound of formula (I), or of its salts, solvates or prodrugs.

The compounds of the present invention represented by the above described formula (I) may include enantiomers depending on the presence of chiral centres or isomers depending on the presence of double bonds (e.g. Z, E). The single isomers, enantiomers or diastereoisomers and mixtures thereof fall within the scope of the present invention.

The compounds of formula (I) defined above can be obtained by available synthetic procedures. For example, they can be prepared by the coupling of a compound of Formula (II):

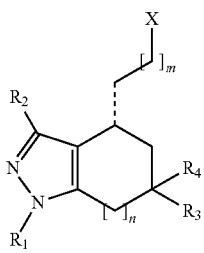

(II)

in which $R_1$-$R_4$, m and n are as defined above in formula (I), and X is a leaving group, preferably chlorine or pyridinium, with a compound of Formula (III):

HNR$_5$R$_6$ (III)

in which $R_5$ and $R_6$ are as defined above in formula (I)

The reaction of compounds of formulas (II) and (III) is preferably carried out in an aprotic solvent, but not limited to, such as dimethylformamide (DMF) in the presence of an inorganic base, such as $K_2CO_3$. Compounds of Formula (III) are commercially available or can be prepared by conventional methods.

The following schemes I to VI illustrate some methods for preparing the compounds of formula (I):

Method A:

The compounds of formula (I), in particular the compounds of formula (Ia), can be obtained according to the synthetic process described by scheme I:

Scheme I

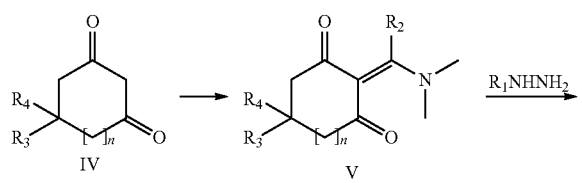

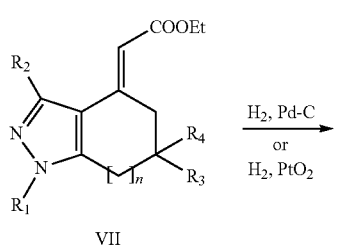

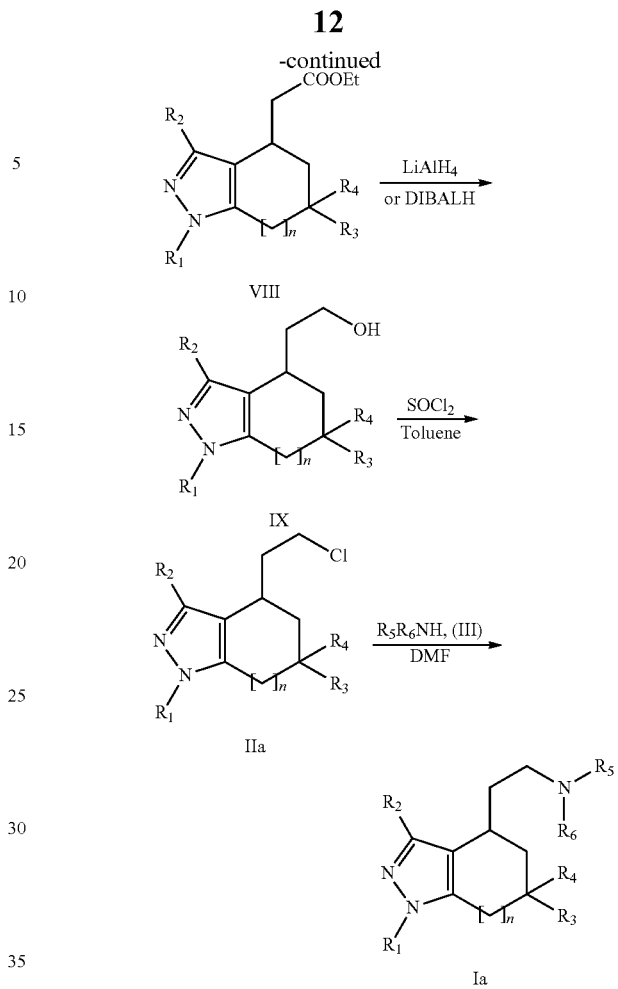

Following Method A, the compounds of formula (VII) are prepared according to methods known from the literature. See, for instance, Schenone, P., Mosti, L. Menozzi, G., *J. Heterocyclic Chem.*, 1982, 19, 1355-1361; Peet, N. P., Letourneau, E., Heterocycles, 1991, 32, 41-72; Mosti, L., et al *Il Farmaco*, 1988, 43, 763-774; Trehan, I. R. et al *Indian Journal of Chemistry*, Section B, 1980, 19b, 243-45.

Following Method A, the compounds of formula (VIII) are prepared from precursors of formula (VII) by catalytic hydrogenation in the presence of catalysts, such as Pd—C or $PtO_2$, in a solvent, such as methanol, ethanol, N,N-dimethylformamide or acetic acid. Likewise, the compounds of formula (VIII), when n=0 and $R_1$=H, can be prepared according to the process disclosed in JP 5765369 A2.

Following Method A, the compounds of formula (IX) are prepared from the intermediates of formula (VIII) by reduction of the ester group with aluminum-lithium hydride or diisobutylaluminium hydride in an inert solvent, such as ethylic ether, tetrahydrofuran, or toluene, at an appropriated temperature which may be between −78° C. and the reflux temperature of the solvent.

Finally, following Method A, the compounds of formula (IIa) are prepared from the compounds of formula (IX) by transformation of the hydroxylic group into a leaving group, such as chlorine, by reaction with thionyl chloride in an inert solvent, such as toluene, at an appropriated temperature which may be between room temperature and the reflux temperature of the solvent.

Method B:

The compounds of formula (I), in particular the compounds of formula (Ib), can be obtained according to the synthetic process described by scheme II:

Scheme II

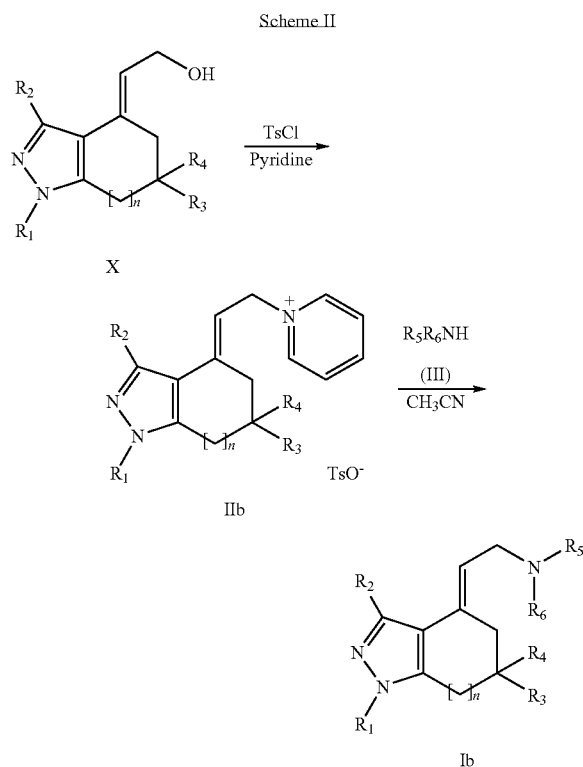

Following Method B, the compounds of formula (X) are prepared according to methods known from the literature. See, for instance, Trehan, I. R. et al *Indian Journal of Chemistry*, Section B, 1980, 19b, 243-45.

Following Method B, the compounds of formula (IIb) are prepared by reaction of compounds of formula (X) with tosyl chloride in pyridine at a temperature between 0° C. and room temperature.

Following Method B, the compounds of formula Ib are prepared by reaction of compounds of formula IIb with amines of formula $R_5R_6NH$ (III) in acetonitrile Method C:

The compounds of formula (I), in particular the compounds of formula (Ib), can be obtained according to the synthetic process described by scheme III:

Scheme III

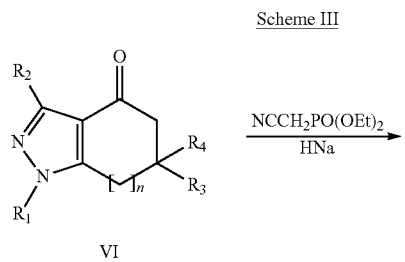

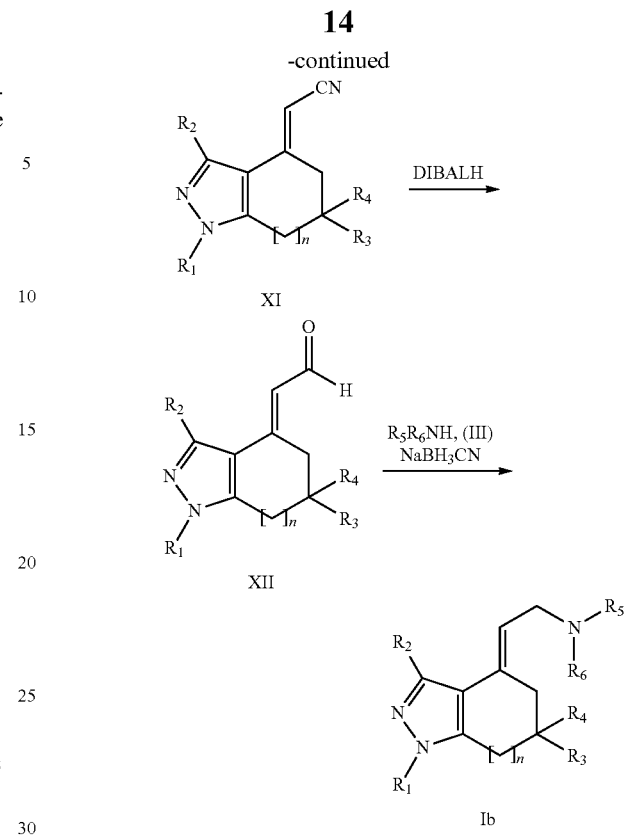

Following Method C, the compounds of formula (XI) are prepared according to well-known methods starting from compounds of formula (VI). See, for instance, Mosti, L. et al., *Il Farmaco*, 1988, 43, 763-774.

Following Method C, the compounds of formula (XII) are prepared from compounds of formula (XI) by reduction of the cyano group with diisobutylaluminum hydride in an inert solvent such as tetrahydrofuran, toluene or methylene chloride and at an appropriated temperature between –78° C. and room temperature.

Finally, following Method C, the compounds of formula (Ib) are prepared by reductive amination of the aldehydes of formula (XII) with amines of formula $R_5R_6NH$ (III) in the presence of reductive agents such as sodium cyanoborohydride ($NaBH_3CN$) or sodium borohydride ($NaBH_4$) in a solvent such as methanol or ethanol and at an appropriated temperature between 0° C. and room temperature.

Method D:

The compounds of formula (I), in particular the compounds of formula (Ib), can also be obtained according to the synthetic process described by scheme IV:

Scheme IV

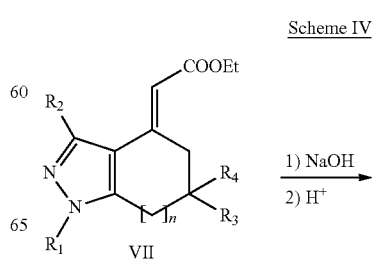

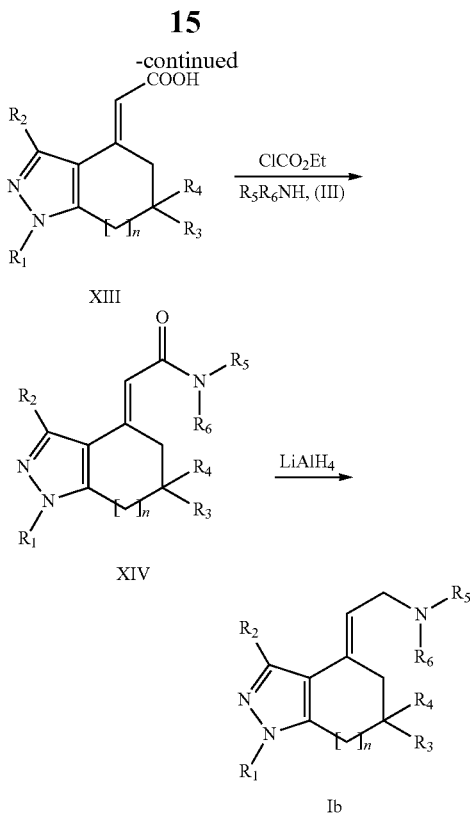

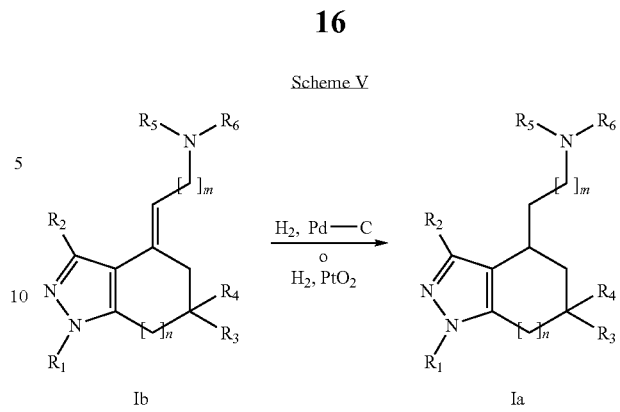

Following Method D, the compounds of formula (XIII) are prepared from the compounds of formula (VII) by hydrolysis of the ester group with a base such as NaOH, KOH or LiOH in a mixture of water and an alcohol such as methanol or ethanol, and at an appropriated temperature between room temperature and the reflux temperature of the solvent.

Following Method D, the compounds of formula (XIV) are prepared by reaction of the compounds of formula (XIII) with alkyl chloroformate, such as methyl chloroformate, ethyl chloroformate, isoprenyl chloroformate, or isobutyl chloroformate, in the presence of a base such as triethylamine, ethyldiisopropylamine or N-methylmorpholine, and subsequent treatment with amines of the formula $R_5R_6NH$ (III), in an inert solvent such as methylene chloride, tetrahydrofuran or N,N-dimethylformamide, and at an appropriated temperature between 0° C. and room temperature. The compounds of formula (XIV) can also be prepared from the compounds of formula (XIII) and the amines of formula $R_5R_6NH$ (III) in the presence of reactives which activate carbonyl groups such as N,N'-dicycloohexylcarbodiimide, 1-(3-dimethylaminopropyl)-3-ethylcarbodiimide, hydrochloride or diisopropylcarbodiimide. This reaction can also be carried out using the carbodiimides in the presence of 1-benzotriazole or N-hydroxysuccinimide. The compounds of formula (XIV) can also be prepared from the compounds of formula (XIII) and the amines of formula $R_5R_6NH$ (III) in the presence of N,N'-carbonyldiimidazole.

Following Method D, the compounds of formula (Ib) are prepared from the compounds of formula (XIV) by reaction with reducing agents such as aluminum and lithium hydride, diisobutylaluminum hydride or in two steps using triethyloxonium tetrafluoroborate and sodium borohydride (E. Cereda, et al., *Tetrahedron Letters*, 21, 4977-4980, 1980).

Method E:

The compounds of formula (I), in particular the compounds of formula (Ia), can be obtained according to the synthetic process described by scheme V:

Following Method E, the compounds of formula (Ia) are prepared from the compounds of formula (Ib) by catalytic hydrogenation in the presence of catalysts such as Pd—C or $PtO_2$, in a solvent such as methanol, ethanol, N,N-dimethylformamide or acetic acid.

Method F:

The compounds of formula (I), in particular the compounds of formula (Ia), can be obtained according to the synthetic process described by scheme VI:

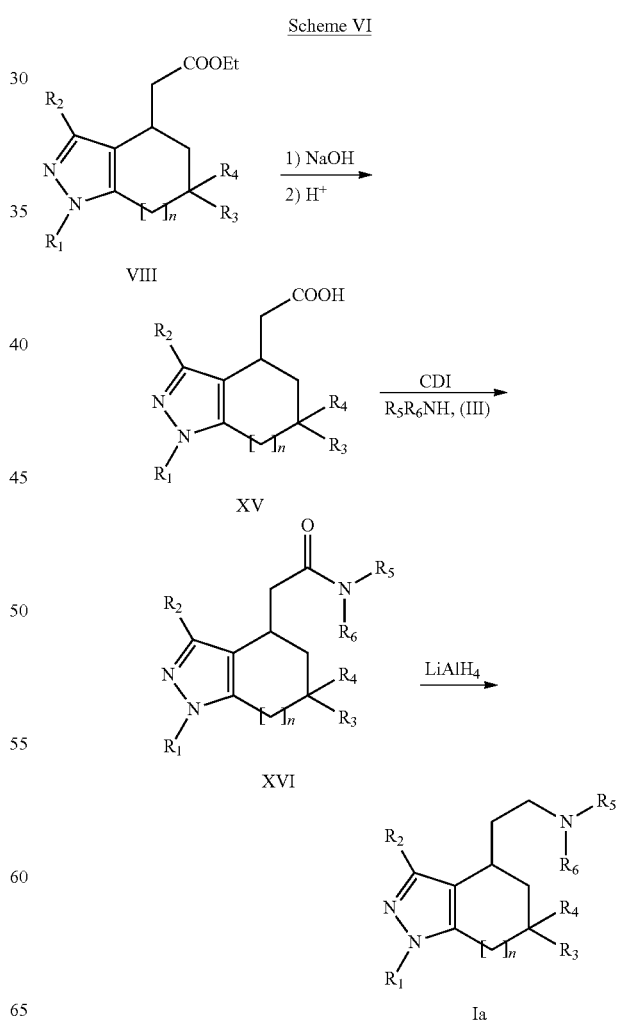

Following Method F, the compounds of formula (XV) are prepared from the compounds of formula (VIII) by hydrolysis of the ester group with a base such as NaOH, KOH or LiOH in a mixture of water and an alcohol such as methanol or ethanol, and at a suitable temperature which may be between room temperature and the reflux temperature of the solvent.

Following Method F, the compounds of formula (XVI) are prepared from the compounds of formula (XV) and the amines of formula $R_5R_6NH$ (III) in the presence of N,N'-carbonyldiimidazole. The compounds of formula (XVI) can also be prepared by reaction of the compounds of formula (XV) with alkyl chloroformate, such as methyl chloroformate, ethyl chloroformate, isoprenyl chloroformate or isobutyl chloroformate in the presence of a base such as triethylamine, ethyldiisopropylamine or N-methylmorpholine and subsequent treatment with amines of formula $R_5R_6NH$ (III), in an inert solvent such as methylene chloride, tetrahydrofuran or N,N-dimethylformamide and at a temperature that can be between 0° C. and room temperature. The compounds of formula (XVI) can also be prepared from the compounds of formula (XV) and the amines of formula $R_5R_6NH$ (III) in the presence of carbonyl group activation reagents such as N,N'-dicyclohexylcarbodiimide, 1-(3-dimethylaminopropyl)-3-ethylcarbodiimide hydro-chloride or diisopropylcarbodiimide. This reaction can also be carried out using the carbodiimides in the presence of 1-benzotriazole or N-hydroxysuccinimide.

Following Method F, the compounds of formula (Ia) are prepared from the compounds of formula (XVI) by reaction with reducing agents such as aluminum and lithium hydride, diisobutylaluminum hydride or in two steps using triethyloxonium tetrafluoroborate and sodium borohydride.

The obtained reaction products may, if desired, be purified by conventional methods, such as crystallisation, chromatography and trituration. Where the above described processes for the preparation of compounds of the invention give rise to mixtures of stereoisomers, these isomers may be separated by conventional techniques such as preparative chromatography. If there are chiral centers the compounds may be prepared in racemic form, or individual enantiomers may be prepared either by enantiospecific synthesis or by resolution.

One preferred pharmaceutically acceptable form is the crystalline form, including such form in pharmaceutical composition. In the case of salts and solvates the additional ionic and solvent moieties must also be non-toxic. The compounds of the invention may present different polymorphic forms, it is intended that the invention encompasses all such forms.

Another aspect of this invention relates to a method of treating or preventing a sigma receptor mediated disease which method comprises administering to a patient in need of such a treatment a therapeutically effective amount of a compound of formula (I) or a pharmaceutical composition thereof. Among the sigma mediated diseases that can be treated are diarrhoea, lipoprotein disorders, migraine, obesity, arthritis, hypertension, arrhythmia, ulcer, cognition disorders, cocaine dependency, tardive diskinesia, ischemic stroke, epilepsy, stroke, depression, stress, cancer, pain, especially neuropathic pain or allodynia, or psychotic condition. The compounds of the invention can also be employed as pharmacological tool or as anxiolytic or immunosuppressant.

The present invention further provides pharmaceutical compositions comprising a compound of this invention, or a pharmaceutically acceptable salt, derivative, prodrug or stereoisomers thereof together with a pharmaceutically acceptable carrier, adjuvant, or vehicle, for administration to a patient.

Examples of pharmaceutical compositions include any solid (tablets, pills, capsules, granules etc.) or liquid (solutions, suspensions or emulsions) composition for oral, topical or parenteral administration.

In a preferred embodiment the pharmaceutical compositions are in oral form, either solid or liquid. Suitable dose forms for oral administration may be tablets, capsules, syrops or solutions and may contain conventional excipients known in the art such as binding agents, for example syrup, acacia, gelatin, sorbitol, tragacanth, or polyvinylpyrrolidone; fillers, for example lactose, sugar, maize starch, calcium phosphate, sorbitol or glycine; tabletting lubricants, for example magnesium stearate; disintegrants, for example starch, polyvinylpyrrolidone, sodium starch glycollate or microcrystalline cellulose; or pharmaceutically acceptable wetting agents such as sodium lauryl sulfate.

The solid oral compositions may be prepared by conventional methods of blending, filling or tabletting. Repeated blending operations may be used to distribute the active agent throughout those compositions employing large quantities of fillers. Such operations are conventional in the art. The tablets may for example be prepared by wet or dry granulation and optionally coated according to methods well known in normal pharmaceutical practice, in particular with an enteric coating.

The pharmaceutical compositions may also be adapted for parenteral administration, such as sterile solutions, suspensions or lyophilized products in the appropriate unit dosage form. Adequate excipients can be used, such as bulking agents, buffering agents or surfactants.

The mentioned formulations will be prepared using standard methods such as those described or referred to in the Spanish and US Pharmacopoeias and similar reference texts.

Administration of the compounds or compositions of the present invention may be by any suitable method, such as intravenous infusion, oral preparations, and intraperitoneal and intravenous administration. Oral administration is preferred because of the convenience for the patient and the chronic character of the diseases to be treated.

Generally an effective administered amount of a compound of the invention will depend on the relative efficacy of the compound chosen, the severity of the disorder being treated and the weight of the sufferer. However, active compounds will typically be administered once or more times a day for example 1, 2, 3 or 4 times daily, with typical total daily doses in the range of from 0.1 to 1000 mg/kg/day.

The compounds and compositions of this invention may be used with other drugs to provide a combination therapy. The other drugs may form part of the same composition, or be provided as a separate composition for administration at the same time or at different time.

The following examples are given only as further illustration of the invention, they should not be taken as a definition of the limits of the invention.

EXAMPLES

Example 1

Synthesis of 4,5,6,7-tetrahydro-4-(2-(morpholin-4-yl)ethyl)-1-phenyl-1H-indazole (1)

Step 1: Synthesis of ethyl 2-(4,5,6,7-tetrahydro-1-phenyl-1H-indazol-4-yl)acetate

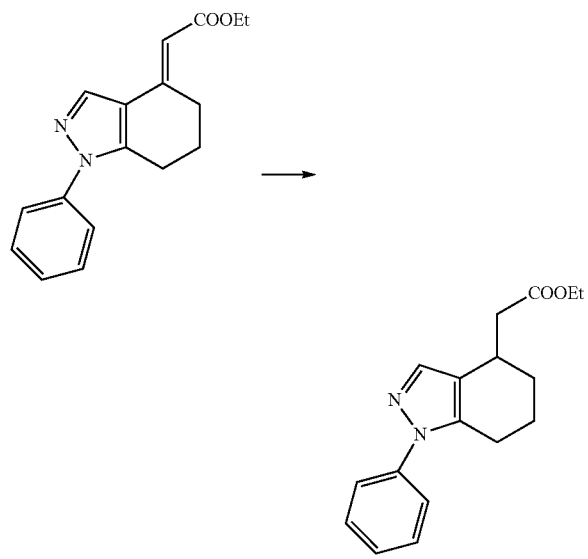

Pd—C (150 mg, 10%) is added to a solution of a mixture of E/Z isomers of ethyl (1,5,6,7-tetrahydro-1-phenyl-4H-indazol-4-ylidene)acetate (1.6 g, 5.67 mmol) in 50 mL of EtOH, and the resulting solution is stirred under nitrogen atmosphere (50 psi) in a Parr hydrogenator for 18 hours. The reaction mixture is purged with nitrogen, filtered through Celite and the solvent is evaporated under reduced pressure, to obtain ethyl 2-(4,5,6,7-tetrahydro-1-phenyl-1H-indazol-4-yl)acetate (1.60 g, 5.63 mmol, 99%, oil).

$^1$H RMN (300 MHz, CDCl$_3$): δ 1.29 (t, J=7.2 Hz, 3H), 1.48 (m, 1H), 1.73 (m, 1H), 1.98 (m, 2H), 2.45 (dd, J=15.4 Hz, J'=8.0 Hz, 1H), 2.68 (m, 3H), 3.26 (m, 1H), 4.20 (q, J=7.2 Hz, 2H), 7.31 (m, 1H), 7.41-7.52 (m, 5H).

Step 2: Synthesis of 2-(4,5,6,7-tetrahydro-1-phenyl-1H-indazol-4-yl)ethanol.

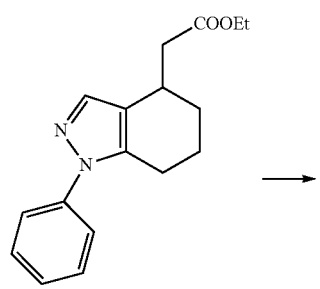

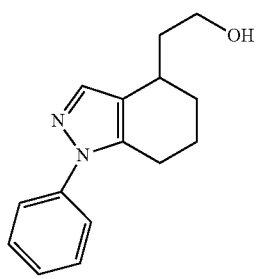

A solution of ethyl 2-(4,5,6,7-tetrahydro-1-phenyl-1H-indazol-4-yl)acetate (1.40 g, 5.79 mmol) in 5 mL of THF is added over an aluminum-lithium hydride stirred suspension (300 mg, 7.9 mmol) in 20 mL of THF at room temperature. The mixture is maintained under stirring at room temperature for 18 hours and is afterwards refluxed during 1 hour. The mixture is hydrolyzed with ice and NaOH (10%), filtered through Celite and the solvent is evaporated under reduced pressure, to obtain 2-(4,5,6,7-tetrahydro-1-phenyl-1H-indazol-4-yl)ethanol (1.10 g, 4.55 mmol, 79%, oil)

$^1$H RMN (300 MHz, CDCl$_3$): δ 1.45 (m, 1H), 1.72 (m, 2H), 1.98 (m, 3H), 2.32 (br s, 1H), 2.71 (m, 2H), 2.91 (m, 1H), 3.84 (t, J=6.7 Hz, 2H), 7.32 (m, 1H), 7.40-7.55 (m, 4H), 7.57 (s, 1H).

Step 3: Synthesis of 4-(2-chloroethyl)-4,5,6,7-tetrahydro-1-phenyl-1H-indazole

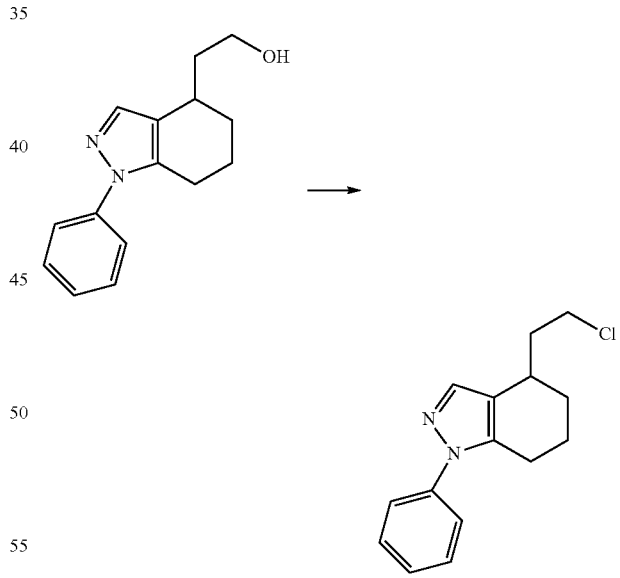

Thionyl chloride (4 mL) is slowly added at room temperature over a solution of 2-(4,5,6,7-tetrahydro-1-phenyl-1H-indazol-4-yl)ethanol (516 mg, 2.13 mmol) in 25 mL of toluene. The reaction mixture is heated at 90° C. during 2 hours. The solvent is eliminated at reduced pressure. The crude is diluted in ethyl acetate and washed twice with a NaHCO$_3$ solution. The solvent is next evaporated at reduced pressure, to obtain 4-(2-chloroethyl)-4,5,6,7-tetrahydro-1-phenyl-1H-indazole (423 mg, 1.62 mmol, 76%, oil).

¹H RMN (300 MHz, CDCl₃): δ 1.45 (m, 1H), 1.73 (m, 1H), 1.94 (m, 3H), 2.18 (m, 1H), 2.71 (m, 2H), 3.00 (m, 1H), 3.70 (t, J=6.8 Hz, 2H), 7.32 (m, 1H), 7.47 (m, 4H), 7.55 (s, 1H).

Step 4: Synthesis of 4,5,6,7-tetrahydro-4-(2-(morpholin-4-yl)ethyl)-1-phenyl-1H-indazole

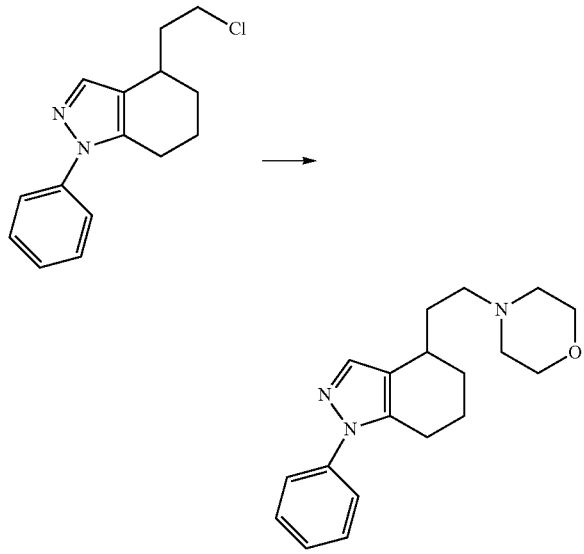

A mixture of 4-(2-chloroethyl)-4,5,6,7-tetrahydro-1-phenyl-1H-indazole (423 mg, 1.62 mmol), K₂CO₃ (336 mg, 2.43 mmol), morpholin (0.42 mL, 4.87 mmol) and a catalytic amount of KI in 20 mL of DMF is heated to reflux during 18 hours. The solvent is eliminated at reduced pressure, the crude is diluted with ethyl acetate, washed with water, and the organic phase is evaporated at reduced pressure. The resultant crude is purified by chromatography on silica-gel to obtain 4,5,6,7-tetrahydro-4-(2-(morpholin-4-yl)ethyl)-1-phenyl-1H-indazole (384 mg, 1.23 mmol, 76%, oil)

¹H RMN (300 MHz, CDCl₃): δ 1.42 (m, 1H), 1.67 (m, 2H), 1.92 (m, 3H), 2.40-2.60 (m, 6H), 2.69 (m, 2H), 2.77 (m, 1H), 3.74 (m, 4H), 7.29 (m, 1H), 7.44 (m, 4H), 7.51 (s, 1H).

Example 2

Synthesis of 4,5,6,7-tetrahydro-4-(2-(morpholin-4-yl)ethyl)-1-phenyl-1H-indazole oxalate (2)

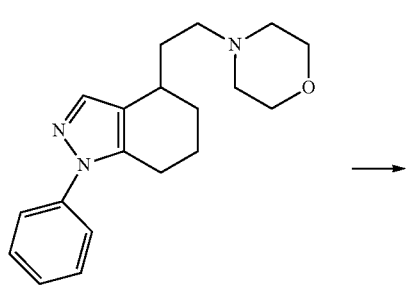

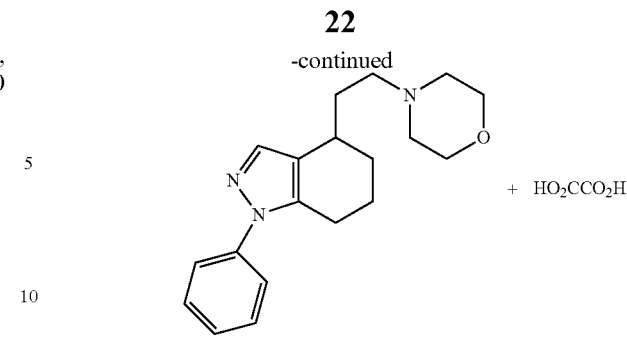

HO₂CCO₂H.2H₂O (156 mg, 1.23 mmol) is added to a solution of 4,5,6,7-tetrahydro-4-(2-(morpholin-4-yl)ethyl)-1-phenyl-1H-indazole (380 mg, 1.22 mmol) in 4 mL of acetone giving 4,5,6,7-tetrahydro-4-(2-(morpholin-4-yl)ethyl)-1-phenyl-1H-indazole oxalate (318 mg, 0.79 mmol, 65%, white solid).

m.p.=150-151° C.

¹H RMN (300 MHz, DMSO-d₆, TFA): δ 1.36 (m, 1H), 1.60 (m, 1H), 1.71-1.93 (m, 3H), 2.04 (m, 1H), 2.56-2.77 (m, 3H), 3.03 (m, 2H), 3.21 (m, 2H), 3.44 (d, J=12.7 Hz, 2H), 3.62 (t, J=11.6 Hz, 2H), 3.92 (m, 2H), 7.29 (m, 1H), 7.38-7.49 (m, 4H), 7.62 (s, 1H), 9.69 (m, 1H).

Example 3

Synthesis of 1-(3,4-dichlorophenyl)-4,5,6,7-tetrahydro-4-(2-(4-phenylpiperidin-1-yl)-ethyl)-1H-indazole (3)

Step 1: Synthesis of 1-(3,4-dichlorophenyl)-1,5,6,7-tetrahydro-4H-indazol-4-one

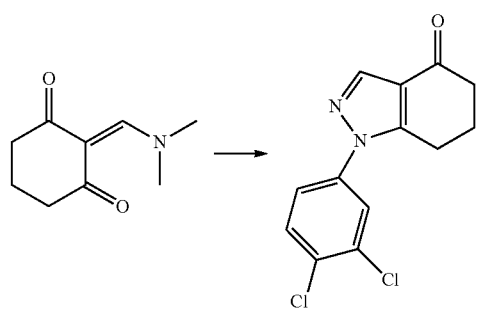 [SMILES: CN(C)C=C1C(=O)CCCC1=O ; O=C1CCCc2c1cnn2-c1ccc(Cl)c(Cl)c1]

A mixture of 1-(3,4-dichlorophenyl)hydrazine hydrochloride (6.78 g, 31.8 mmol) and anhydrous sodium acetate (2.60 g, 31.8 mmol) in n-BuOH (20 mL) is slowly added to a solution of 2-((dimethylamino)methylene)cyclohexane-1,3-dione (5.32 g, 31.8 mmol) in n-BuOH (100 mL) and acetic acid (5 mL). The resulting mixture is heated to reflux during 2 hours, effecting follow-up of the reaction by TLC. The solvent is evaporated at reduced pressure, the residue is diluted in AcOEt and washed with H₂O. The solvent is next evaporated, and the crude is purified by silica-gel chromatography, to obtain 1-(3,4-dichlorophenyl)-1,5,6,7-tetrahydro-4H-indazol-4-one (5.0 g, 17.79 mmol, 56%, orange solid).

¹H RMN (300 MHz, CDCl₃): δ 2.17 (m, 2H), 2.51 (m, 2H), 2.96 (t, J=6.1 Hz, 2H), 7.36 (t, J=8.6 Hz, J'=2.4 Hz, 1H), 7.54 (d, J=8.6 Hz, 1H), 7.64 (d, J=2.4 Hz, 1H), 8.02 (s, 1H).

Step 2: Synthesis of a E/Z isomers mixture of ethyl (1-(3,4-dichlorophenyl)-1,5,6,7-tetrahydro-4H-indazol-4-ylidene)acetate

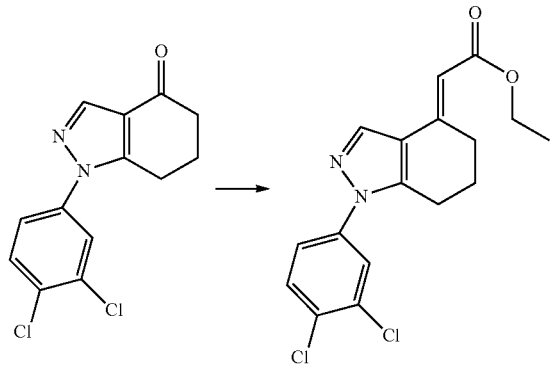 [SMILES: O=C1CCCc2c1cnn2-c1ccc(Cl)c(Cl)c1 ; CCOC(=O)/C=C1\CCCc2c1cnn2-c1ccc(Cl)c(Cl)c1]

A suspension of sodium hydride (428 mg, 60% suspension, 10.6 mmol) is added under nitrogen atmosphere to a solution of triethyl phosphonoacetate (2.40 g, 10.6 mmol) in THF (40 mL) and maintained to room temperature during 10 minutes. Next, 1-(3,4-dichlorophenyl)-1,5,6,7-tetrahydro-4H-indazol-4-one (1.0 g, 3.56 mmol) is added to the previous solution and the mixture is refluxed during 18 hours, effecting a follow-up of the reaction with TLC. The solution is poured over water and is then extracted with AcOEt. The organic phase is next evaporated at reduced pressure to obtain a solidifying oil and the crude is purified by silica-gel chromatography, to obtain a E/Z isomers mixture of ethyl (1-(3,4-dichlorophenyl)-1,5,6,7-tetrahydro-4H-indazol-4-ylidene)acetate (1.2 g, 3.41 mmol, 96%, orange solid).

¹H RMN (300 MHz, CDCl₃): δ 1.31 (t, J=7.1 Hz, 3H), 1.96 (m, 2H), 2.56 y 3.16 (2 m, 2H), 2.84 (m, 2H), 4.20 (m, 2H), 5.67 y 6.09 (2s, 1H), 7.35 (d, J=8.6 Hz, 1H), 7.53 (d, J=8.6 Hz, 1H), 7.64 (s, 1H), 7.90 y 8.83 (2s, 1H).

Step 3: Synthesis of ethyl 2-(1-(3,4-dichlorophenyl)-4,5,6,7-tetrahydro-1H-indazol-4-yl)acetate

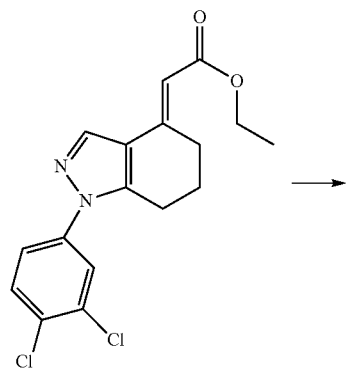

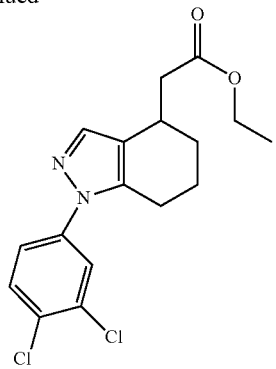

PtO₂ (30 mg) is added to a solution of a E/Z isomers mixture of ethyl (1-(3,4-dichlorophenyl)-1,5,6,7-tetrahydro-4H-indazol-4-ylidene)acetate (1.5 g, 4.27 mmol) in acetic acid (25 mL); the mixture is maintained under stiffing under a pressure of 1H₂ atm. A sample is next extracted and a ¹H NRM is done. The mixture is then filtered, diluted with AcOEt, and washed with H₂O and with a saturated solution of NaHCO₃. The solvent is next evaporated at reduced pressure, giving ethyl 2-(1-(3,4-dichlorophenyl)-4,5,6,7-tetrahydro-1H-indazol-4-yl)acetate (1.0 g, 2.83 mmol, purity 66%, oil).

¹H RMN (300 MHz, CDCl₃): δ 1.29 (t, J=7.2 Hz, 3H), 1.45 (m, 1H), 1.74 (m, 1H), 1.98 (m, 2H), 2.44 (dd, J=15.4 Hz, J'=7.9 Hz, 1H), 2.61-2.73 (m, 3H), 3.24 (m, 1H), 4.20 (q, J=7.2 Hz, 2H), 7.36 (dd, J=8.8 Hz, J'=2.5 Hz, 1H), 7.50 (m, 2H), 7.64 (d, J=2.5 Hz, 1H).

Step 4: Synthesis of 2-(1-(3,4-dichlorophenyl)-4,5,6,7-tetrahydro-1H-indazol-4-yl)ethanol

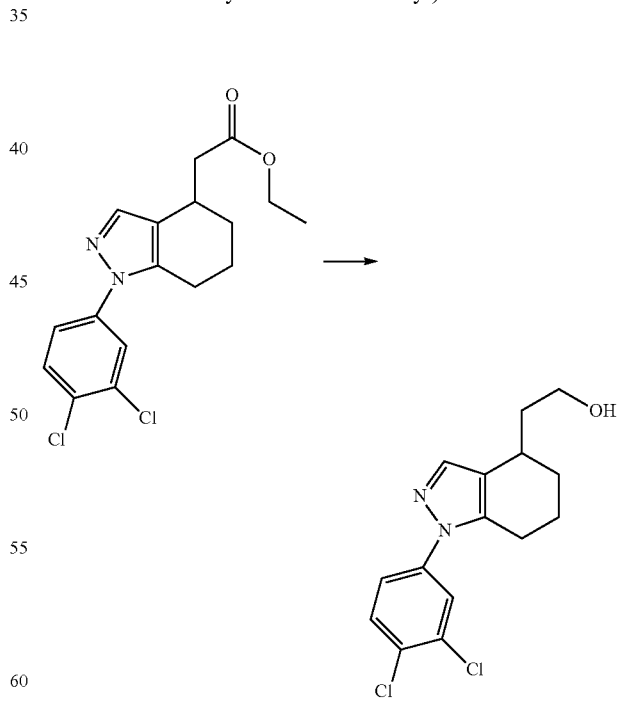

A solution of DIBALH (1 M) in toluene (13 mL, 13.0 mmol) is slowly added, maintaining the reaction temperature under −65° C., to a solution of ethyl 2-(1-(3,4-dichlorophenyl)-4,5,6,7-tetrahydro-1H-indazol-4-yl)acetate (1.83 g, 5.2 mmol) in 20 mL of dried Cl₂CH₂ cooled at −75° C. under N₂ atmosphere. The resulting mixture is maintained under stirring at −70° C. during 30 minutes, effecting a follow-up of the reaction by TLC. Next, the temperature is raised to 0° C., and 10 mL of cold water are added, while the temperature is maintained at 0° C. A precipitate is formed, which is filtered and washed with Cl$_2$CH$_2$. The organic phase is washed twice with water, dried, and evaporated under reduced pressure. The resulting crude is purified by silica-gel chromatography, giving 2-(1-(3,4-dichlorophenyl)-4,5,6,7-tetrahydro-1H-indazol-4-yl)ethanol (1.06 g, 3.41 mmol, 66%, oil).

$^1$H RMN (300 MHz, CDCl$_3$): δ 1.43 (m, 1H), 1.70 (m, 2H), 1.90-2.18 (m, 4H), 2.69 (m, 2H), 2.87 (m, 1H), 3.79 (t, J=6.6 Hz, 2H), 7.35 (dd, J=8.7 Hz, J'=2.5 Hz, 1H), 7.49 (d, J=8.7 Hz, 1H), 7.53 (s, 1H), 7.64 (d, J=2.5 Hz, 1H).

Step 5: Synthesis of 4-(2-chloroethyl)-4,5,6,7-tetrahydro-1-(3,4-dichlorophenyl)-1H-indazole

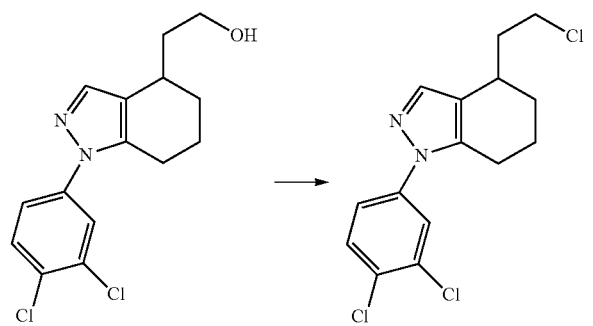 [SMILES: OCCC1CCCc2c1cnn2-c1ccc(Cl)c(Cl)c1 ; ClCCC1CCCc2c1cnn2-c1ccc(Cl)c(Cl)c1]

Thionyl chloride (4 mL) is slowly added at room temperature over a solution of 2-(1-(3,4-dichlorophenyl)-4,5,6,7-tetrahydro-1H-indazol-4-yl)ethanol (512 mg, 1.65 mmol) in 20 mL of toluene. The reaction mixture is heated at 90° C. during 2 hours. The solvent is eliminated at reduced pressure. The crude is diluted in ethyl acetate and washed twice with a NaHCO$_3$ solution. The solvent is next evaporated at reduced pressure to obtain 4-(2-chloroethyl)-4,5,6,7-tetrahydro-1-(3,4-dichlorophenyl)-1H-indazole (462 mg, 1.40 mmol, 85%, oil).

$^1$H RMN (300 MHz, CDCl$_3$): δ 1.44 (m, 1H), 1.75 (m, 1H), 1.84-2.12 (m, 3H), 2.18 (m, 1H), 2.72 (m, 2H), 2.99 (m, 1H), 3.69 (t, J=7.0 Hz, 2H), 7.37 (dd, J=8.6 Hz, J'=2.5 Hz, 1H), 7.50 (d, J=8.6 Hz, 1H), 7.54 (s, 1H), 7.65 (d, J=2.5 Hz, 1H).

Step 6: Synthesis of 1-(3,4-dichlorophenyl)-4,5,6,7-tetrahydro-4-(2-(4-phenylpiperidin-1-yl)ethyl)-1H-indazole

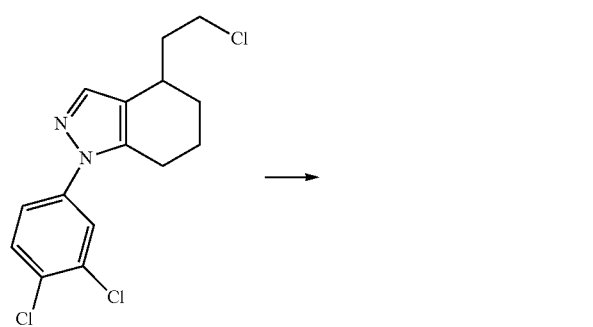

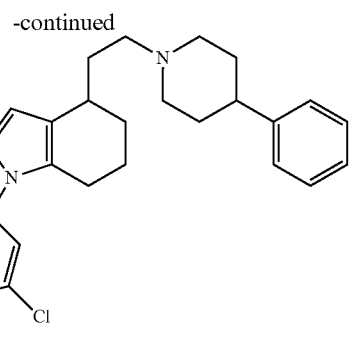

A mixture of 4-(2-chloroethyl)-4,5,6,7-tetrahydro-1-(3,4-dichlorophenyl)-1H-indazole (235 mg, 0.71 mmol), K$_2$CO$_3$ (99 mg, 0.71 mmol), 4-phenylpiperidine (97 mg, 0.71 mmol) and a catalytic amount of KI in 5 mL of DMF is heated to reflux during 18 hours. The solvent is eliminated at reduced pressure, the crude is diluted with ethyl acetate, washed with water, and the organic phase is evaporated at reduced pressure. The resultant crude is purified by chromatography on silica-gel to obtain 1-(3,4-dichlorophenyl)-4,5,6,7-tetrahydro-4-(2-(4-phenylpiperidin-1-yl)ethyl)-1H-indazole (146 mg, 0.32 mmol, 45%, oil).

$^1$H RMN (300 MHz, CDCl$_3$): δ 1.36-2.30 (m, 12H), 2.50-2.83 (m, 6H), 3.20 (m, 2H), 7.18-7.40 (m, 6H), 7.51 (d, J=8.6 Hz, 1H), 7.55 (s, 1H), 7.66 (d, J=2.3 Hz, 1H).

Example 4

Synthesis of 1-(3,4-dichlorophenyl)-4,5,6,7-tetrahydro-4-(2-(4-phenylpiperidin-1-yl)ethyl)-1H-indazole oxalate (4)

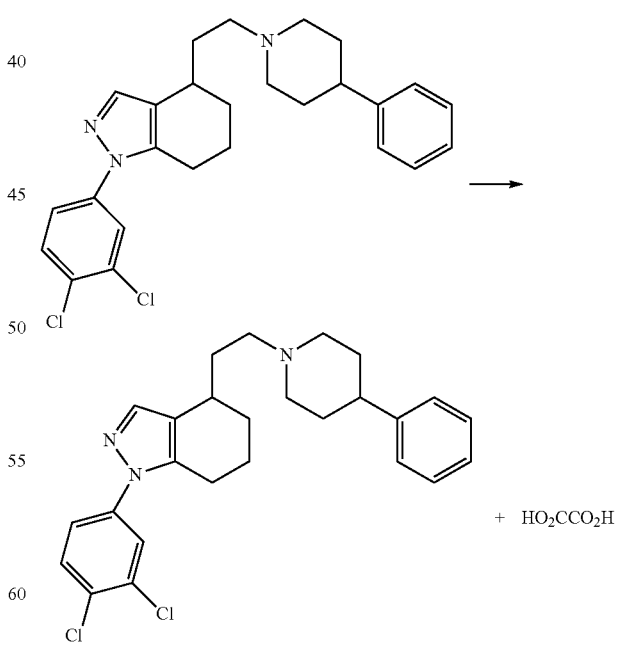

HO$_2$CCO$_2$H.2H$_2$O (40 mg, 0.32 mmol) is added to a solution of 1-(3,4-dichlorophenyl)-4,5,6,7-tetrahydro-4-(2-(4-phenylpiperidin-1-yl)ethyl)-1H-indazole (140 mg, 0.31 mmol) in 4 mL of acetone, giving 1-(3,4-dichlorophenyl)-4, 5,6,7-tetrahydro-4-(2-(4-phenylpiperidin-1-yl)ethyl)-1H-indazole oxalate (125 mg, 0.23 mmol, 74%, white solid).

m.p.=133-134° C.

Example 5

Synthesis of (E)-4,5,6,7-tetrahydro-4-(2-(morpholin-4-yl)ethylidene)-1-phenyl-1H-indazole (5)

Method D

Step 1: Synthesis of the E/Z mixture of 2-(1,5,6,7-tetrahydro-1-phenyl-4H-inazol-4-ylidene)acetic acid

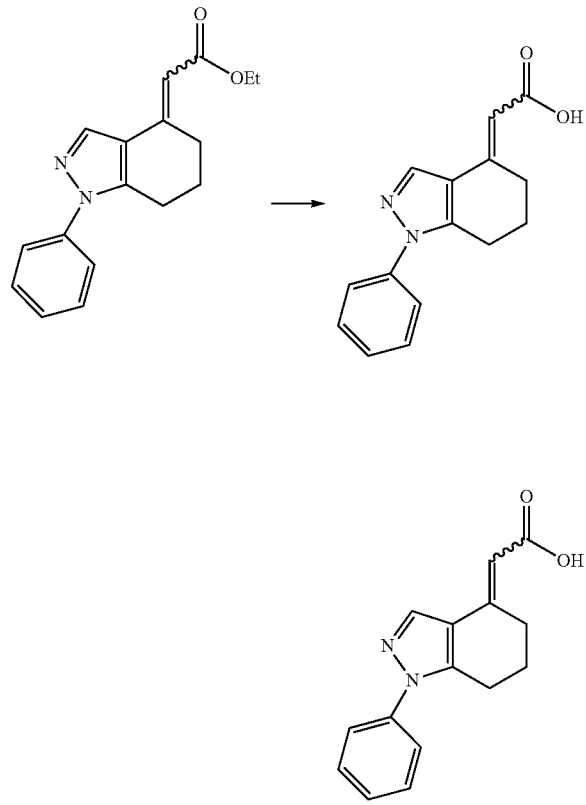

H$_2$O (15 mL) and 10% NaOH (3 mL, 7.5 mmol) are added to a solution of a mixture of E/Z of ethyl 2-(1,5,6,7-tetrahydro-1-phenyl-4H-indazol-4-ylidene)acetate (2.06 g, 7.31 mmol) in ethanol (30 mL) and refluxed for 3 hours, following the reaction by means of TLC. The ethanol is evaporated under reduced pressure and acidified with 1N HCl, and the precipitate that is formed is filtered, washed with H$_2$O and dried, giving a mixture of E/Z (85/15) of 2-(1,5,6,7-tetrahydro-1-phenyl-4H-indazol-4-ylidene)acetic acid (1.37 g, 5.39 mmol, 74%).

$^1$H NMR (300 MHz, CDCl$_3$): δ 1.94 (m, 2H), 2.59 (2×m, (0.30+1.70)H), 2.86 (m, 2H), 5.70 and 6.12 (2×s, (0.15+0.85) H), 7.38 (m, 1H), 7.48 (m, 4H), 7.94 and 8.85 (2×s, (0.85+ 0.15)H).

Step 2: Synthesis of (E/Z)-4-(2-(1-phenyl-6,7-dihydro-1H-indazol-4(5H)-ylidene)acetyl)-morpholine

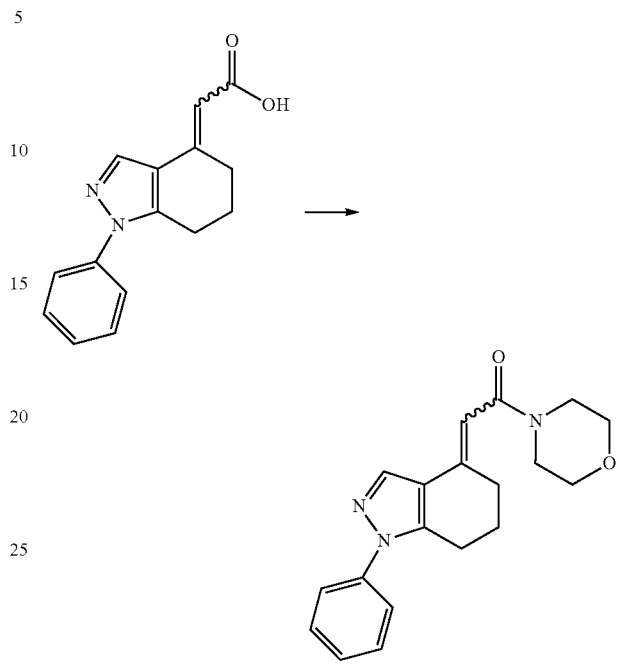

Triethylamine (0.054 mL, 0.39 mmol) and ethyl chloroformate (0.037 mL, 0.30 mmol) are added to a solution of a mixture of E/Z of 2-(1,5,6,7-tetrahydro-1-phenyl-4H-indazol-4-ylidene)acetic acid (100 mg, 0.39 mmol) in CH$_2$Cl$_2$ (5 mL) cooled to 0° C. and is stirred for 45 minutes at 0° C. Then morpholine (0.034 mL, 0.39 mmol) is added following the reaction by means of TLC. The solution is washed with diluted NaOH, the organic phase is separated, dried and evaporated under reduced pressure. The resulting crude product is purified by means of silica gel chromatography giving an E/Z mixture (80/20) of 4-(2-(1-phenyl-6,7-dihydro-1H-indazol-4(5H)-ylidene)acetyl)morpholine (40 mg, 0.12 mmol, 32%).

$^1$H NMR (300 MHz, CDCl$_3$): δ 1.91 (m, 2H), 2.50 and 2.75-3.00 (2×m, (0.40+3.60)H), 3.50-3.90 (m, 8H), 5.67 and 6.24 (2×s, (0.20+0.80)H), 7.36 (m, 1H), 7.48 (m, 4H), 7.86 and 7.93 (2×s, (0.80+0.20)H).

Step 3: Synthesis of (E)-4,5,6,7-tetrahydro-4-(2-(morpholin-4-yl)ethylidene)-1-phenyl-1H-indazole

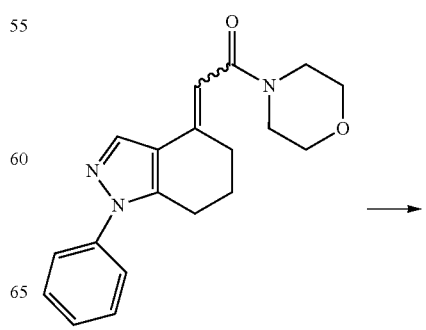

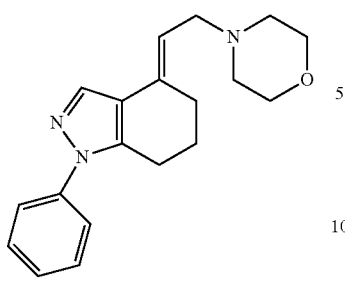

An E/Z mixture of 4-(2-(1-phenyl-6,7-dihydro-1H-indazol-4(5H)-ylidene)acetyl)-morpholine (398 mg, 1.23 mmol) is added to a mixture of LiAlH₄ (129 mg, 3.70 mmol) in THF (10 mL) cooled to 0° C. The temperature of the reaction is allowed to increase up to room temperature and is stirred for 4 hours, and then the reaction is refluxed for 30 minutes. The mixture is cooled in an ice bath and ice is added. The insoluble solid is filtered and washed with AcOEt. The organic phase is washed with H₂O, dried and evaporated under reduced pressure, giving an E/Z mixture of 4,5,6,7-tetrahydro-4-(2-(morpholin-4-yl)ethylidene)-1-phenyl-1H-indazol which is purified by means of silica gel chromatography giving (E)-4,5,6,7-tetrahydro-4-(2-(morpholin-4-yl)ethylidene)-1-phenyl-1H-indazole (118 mg, 0.38 mmol, 31%) and an E/Z mixture of 4,5,6,7-tetrahydro-4-(2-(morpholin-4-yl)ethylidene)-1-phenyl-1H-indazole (80.2 mg, 0.26 mmol, 21%).

The ¹H NMR spectrum (300 MHz, CDCl₃) of (E)-4,5,6,7-tetrahydro-4-(2-(morpholin-4-yl)ethylidene)-1-phenyl-1H-indazole coincides with the one obtained according to Method A.

A further synthesis for compound (5):

Step 1: Synthesis of 1-[2-(1-phenyl-1,5,6,7-tetrahydro-indazol-4-ylidene)-ethyl]-pyridinium toluene-4-sulfonate

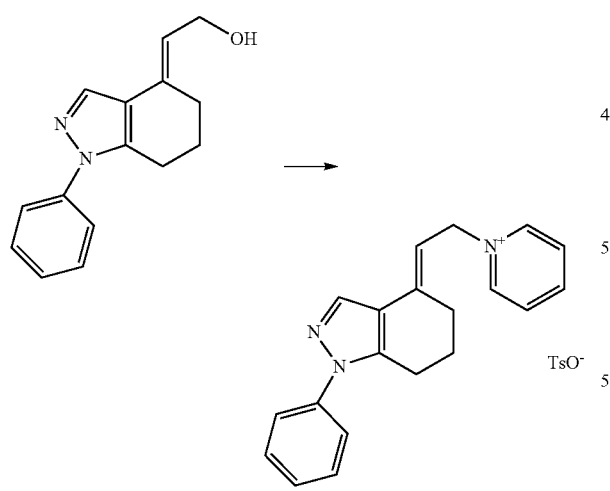

P-toluenesulfonyl chloride (210 mg, 1.10 mmol) is added to a solution of (E)-2-(6,7-dihydro-1-phenyl-1H-indazol-4(5H)-ylidene)ethanol (254 mg, 1.05 mmol) in 10 mL de pyridine cooled to a 0° C. The reaction is followed up by TLC. Next, the solvent is evaporated, the crude is diluted with CHCl₃, and washed with a diluted solution of NaHCO₃. The organic phase is evaporated at reduced pressure, to obtain 1-[2-(1-phenyl-1,5,6,7-tetrahydroindazol-4-ylidene)-ethyl]-pyridinium toluene-4-sulfonate (300 mg, 0.63 mmol, 60%, yellow solid).

Step 2: Synthesis of (E)-4,5,6,7-tetrahydro-4-(2-(morpholin-4-yl)ethylidene)-1-phenyl-1H-indazole

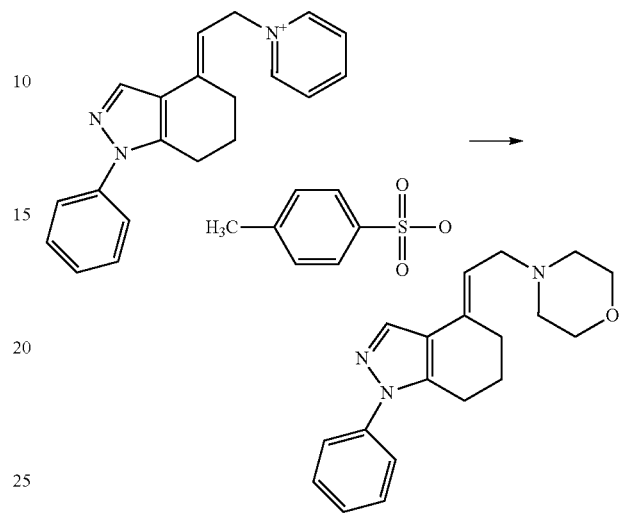

A mixture of 1-[2-(1-phenyl-1,5,6,7-tetrahydro-indazol-4-ylidene)-ethyl]-pyridinium toluene-4-sulfonate (290 mg, 0.63 mmol) and morpholin (180 mg, 1.5 mmol) in 15 mL of acetonitrile is refluxed during 4 hours, following the reaction by TLC. The solvent is next evaporated, the crude is diluted in ethyl acetate and washed three times with water. Then the organic phase is evaporated under reduced pressure. The crude thus obtained is purified by silica gel chromatography giving (E)-4,5,6,7-tetrahydro-4-(2-(morpholin-4-yl)ethylidene)-1-phenyl-1H-indazole (110 mg, 0.36 mmol, 57%, beige solid, m.p=114-116° C.).

¹H RMN (300 MHz, CDCl₃): δ 1.87 (m, 2H), 2.40-2.62 (m, 6H), 2.81 (t, J=6.1 Hz, 2H), 3.18 (d, J=7.3 Hz, 2H), 3.75 (m, 4H), 5.81 (t, J=7.3 Hz, 1H), 7.33 (m, 1H), 7.47 (m, 4H), 7.81 (s, 1H).

The following compounds are prepared in a similar way:

Example 6

1-(3,4-dichlorophenyl)-4,5,6,7-tetrahydro-4-(2-(morpholin-4-yl)ethyl)-1H-indazole (6)

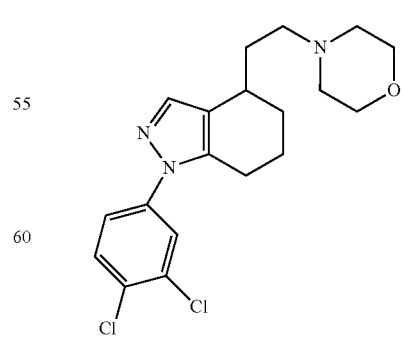

¹H RMN (300 MHz, CDCl₃): δ 1.41 (m, 1H), 1.66 (m, 2H), 1.93 (m, 3H), 2.47 (m, 6H), 2.62-2.79 (m, 3H), 3.71 (t, J=4.7

Hz, 4H), 7.34 (dd, J=8.7 Hz, J'=2.5 Hz, 1H), 7.48 (d, J=8.7 Hz, 1H), 7.49 (s, 1H), 7.63 (d, J=2.5 Hz, 1H), (65 mg, 0.17 mmol, 23%, oil).

Example 7

1-(3,4-dichlorophenyl)-4,5,6,7-tetrahydro-4-(2-(morpholin-4-yl)ethyl)-1H-indazole oxalate (7)

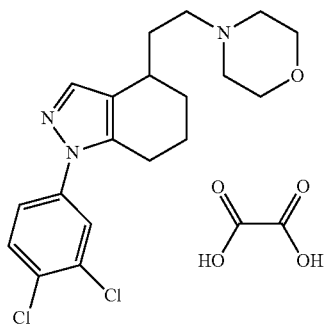

(45 mg, 0.10 mmol, 59%, cream solid, m.p.=148.0-149.8° C.).

Example 8

4,5,6,7-tetrahydro-1-phenyl-4-(2-(4-phenylpiperidin-1-yl)ethyl)-1H-indazole (8)

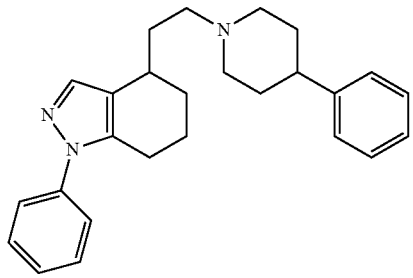 [SMILES: c1ccc(C2CCN(CCC3CCCc4c3cnn4-c3ccccc3)CC2)cc1]

$^1$H RMN (300 MHz, CDCl$_3$): δ 1.44 (m, 1H), 1.70 (m, 1H), 1.79-2.11 (m, 8H), 2.23 (m, 2H), 2.48-2.85 (m, 6H), 3.22 (m, 2H), 7.16-7.35 (m, 6H), 7.40-7.52 (m, 4H), 7.54 (s, 1H), (106 mg, 0.28 mmol, 28%, oil).

Example 9

4,5,6,7-tetrahydro-1-phenyl-4-(2-(4-phenylpiperidin-1-yl)ethyl)-1H-indazole oxalate (9)

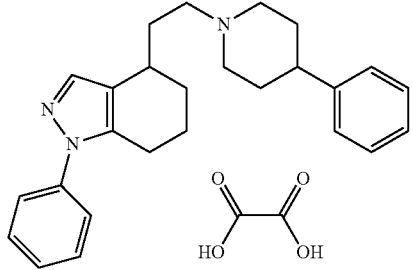

(47 mg, 0.10 mmol, 36%, white solid, m.p.=124-125° C.).

Example 10

4-(2-(4-benzylpiperazin-1-yl)ethyl)-4,5,6,7-tetrahydro-1-phenyl-1H-indazole (10)

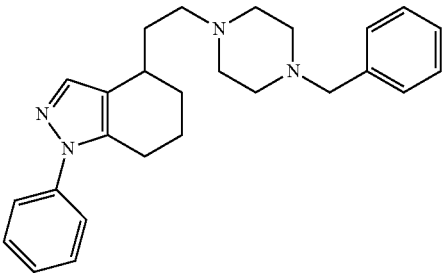 [SMILES: c1ccc(CN2CCN(CCC3CCCc4c3cnn4-c3ccccc3)CC2)cc1]

$^1$H RMN (300 MHz, CDCl$_3$): δ 1.42 (m, 1H), 1.68 (m, 2H), 1.92 (m, 3H), 2.40-2.80 (m, 13H), 3.52 (s, 2H), 7.20-7.37 (m, 6H), 7.39-7.52 (m, 5), (110 mg, 0.27 mmol, 23%, beige solid, m.p.=98-101° C.).

Example 11

4,5,6,7-tetrahydro-1-phenyl-4-(2-[spiro[isobenzofuran-1(3H),4'-piperidin]-1'-yl]ethyl)-1H-indazole (11)

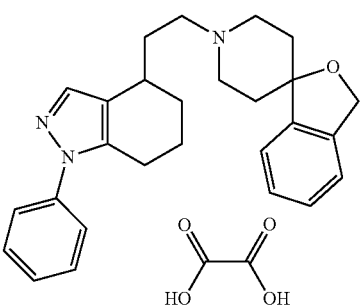

$^1$H RMN (300 MHz, CDCl$_3$): δ 1.40 (m, 1H), 1.60-1.80 (m, 4H), 1.88-2.05 (m, 5H), 2.40 (m, 2H), 2.57 (t, J=7.9 Hz, 2H), 2.67 (m, 2H), 2.74 (m, 1H), 2.90 (m, 2H), 5.04 (s, 2H), 7.10-7.30 (m, 5H), 7.37-7.48 (m, 4H), 7.51 (s, 1H), (163 mg, 0.39 mmol, 34%, oil).

Example 12

4,5,6,7-tetrahydro-1-phenyl-4-(2-[spiro[isobenzofuran-1(3H), 4'-piperidin]-1'-yl]ethyl)-1H-indazole oxalate (12)

(148 mg, 0.29 mmol, 74%, white solid, m.p.=133-135° C.).

Example 13

4,5,6,7-tetrahydro-1-phenyl-4-(2-(piperidin-1-yl)ethyl)-1H-indazole (13)

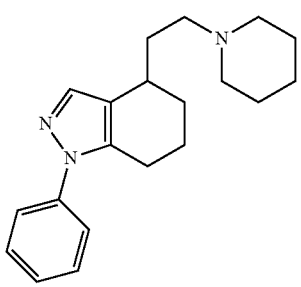 [SMILES: c1ccc(-n2ncc3c2CCCC3CCN2CCCCC2)cc1]

¹H RMN (300 MHz, CDCl₃): δ 1.44 (m, 3H), 1.69 (m, 6H), 1.95 (m, 3H), 2.55 (m, 6H), 2.69 (m, 2H), 2.76 (m, 1H), 7.30 (m, 1H), 7.40-7.50 (m, 4H), 7.51 (s, 1H), (83 mg, 0.27 mmol, 23%, oil).

Example 14

4,5,6,7-tetrahydro-1-phenyl-4-(2-(piperidin-1-yl)ethyl)-1H-indazole oxalate (14)

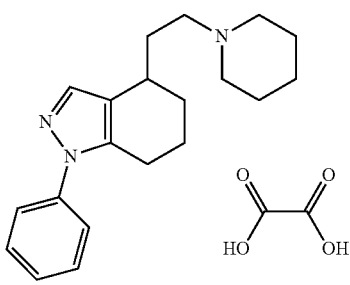 [SMILES: c1ccc(-n2ncc3c2CCCC3CCN2CCCCC2)cc1 ; O=C(O)C(=O)O]

(50 mg, 0.13 mmol, 48%, white solid, m.p.=185-188° C.).

Example 15

(E)-4-(2-(azepan-1-yl)ethylidene)-4,5,6,7-tetrahydro-1-phenyl-1H-indazole (15)

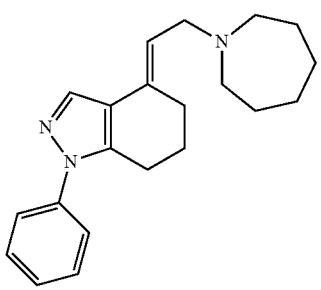 [SMILES: C(/CN1CCCCCC1)=C1/CCCc2c1cnn2-c1ccccc1]

¹H RMN (300 MHz, CDCl₃): δ 1.56-1.80 (m, 8H), 1.85 (m, 2H), 2.47 (m, 2H), 2.73 (m, 4H), 2.81 (t, J=6.1 Hz, 2H), 3.34 (d, J=7.1 Hz, 2H), 5.87 (t, J=7.1 Hz, 1H), 7.32 (m, 1H), 7.47 (m, 4H), 7.83 (s, 1H), (17 mg, 0.05 mmol, 11%, oil).

Example 16

(E)-4-(2-(azepan-1-yl)ethylidene)-4,5,6,7-tetrahydro-1-phenyl-1H-indazole oxalate (16)

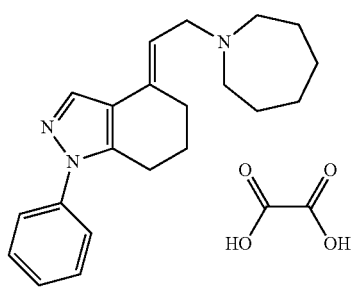 [SMILES: C(/CN1CCCCCC1)=C1/CCCc2c1cnn2-c1ccccc1 ; O=C(O)C(=O)O]

(15 mg, 0.04 mmol, 80%, white solid, m.p.=171-173° C.).

Example 17

(E)-4,5,6,7-tetrahydro-1-phenyl-4-(2-(4-phenylpiperidin-1-yl)ethylidene)-1H-indazole (17)

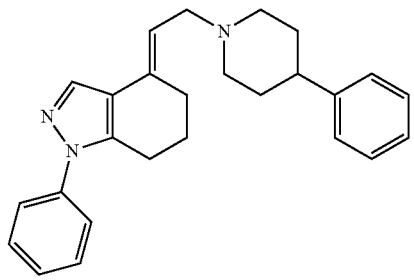 [SMILES: C(/CN1CCC(c2ccccc2)CC1)=C1/CCCc2c1cnn2-c1ccccc1]

¹H RMN (300 MHz, CDCl₃): δ 1.90 (m, 4H), 2.02 (m, 2H), 2.29 (m, 2H), 2.46 (m, 3H), 2.82 (t, J=6.1 Hz, 2H), 3.26 (m, 2H), 3.36 (m, 2H), 5.90 (t, J=7.1 Hz, 1H), 7.18-7.38 (m, 6H), 7.47 (m, 4H), 7.85 (s, 1H), (30 mg, 0.08 mmol, 16%, beige solid, m.p.=110-112° C.).

Example 18

(E)-4,5,6,7-tetrahydro-1-phenyl-4-(2-[spiro[isobenzofuran-1(3H), 4'-piperidin]-1'-yl]ethylidene)-1H-indazole (18)

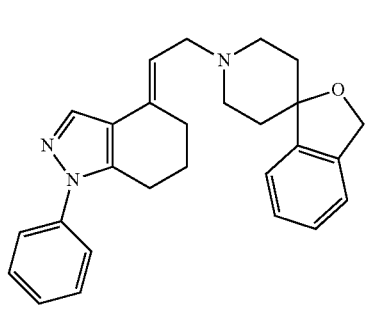 [SMILES: C(/CN1CCC2(CC1)OCc1ccccc12)=C1/CCCc2c1cnn2-c1ccccc1]

¹H RMN (300 MHz, CDCl₃): δ 1.78-1.97 (m, 4H), 2.20 (m, 2H), 2.48-2.70 (m, 4H), 2.82 (t, J=6.0 Hz, 2H), 3.08 (m, 2H), 3.36 (m, 2H), 5.08 (s, 2H), 5.91 (t, J=7.5 Hz, 1H), 7.18-7.38 (m, 5H), 7.47 (m, 4H), 7.86 (s, 1H), (50 mg, 0.12 mmol, 24%, oil).

Example 19

(E)-4,5,6,7-tetrahydro-1-phenyl-4-(2-[spiro[isobenzofuran-1(3H), 4'-piperidin]-1'-yl]ethylidene)-1H-indazole oxalate (19)

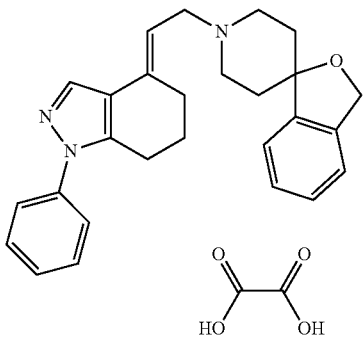

(18 mg, 0.04 mmol, 36%, white solid, m.p.=155-157° C.).

Example 20

(E)-4,5,6,7-tetrahydro-1-phenyl-4-(2-(4-phenylpiperazin-1-yl)ethylidene)-1H-indazole (20)

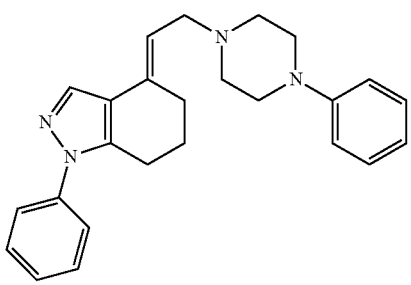 [SMILES: C(/CN1CCN(c2ccccc2)CC1)=C1/CCCc2c1cnn2-c1ccccc1]

¹H RMN (300 MHz, CDCl₃): δ 1.89 (m, 2H), 2.51 (m, 2H), 2.73 (m, 4H), 2.83 (t, J=6.1 Hz, 2H), 3.28 (m, 6H), 5.87 (t, J=7.2 Hz, 1H), 6.86 (t, J=7.4 Hz, 1H), 6.94 (d, J=7.9 Hz, 1H), 7.22-7.37 (m, 3H), 7.48 (m, 4H), 7.84 (s, 1H), (20 mg, 0.05 mmol, 10%, beige solid, m.p.=114-116° C.).

Example 21

1,2,3,4-tetrahydro-2-((E)-2-(6,7-dihydro-1-phenyl-1H-indazol-4(5H)-ylidene)ethyl)isoquinoline (21)

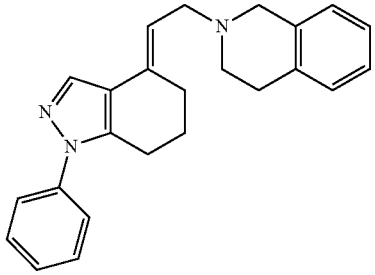 [SMILES: C(/CN1CCc2ccccc2C1)=C1/CCCc2c1cnn2-c1ccccc1]

¹H RMN (300 MHz, CDCl₃): δ 1.90 (m, 2H), 2.52 (m, 2H), 2.83 (m, 4H), 2.95 (m, 2H), 3.38 (d, J=7.2 Hz, 2H), 3.75 (s, 2H), 5.93 (t, J=7.2 Hz, 1H), 7.03 (m, 1H), 7.12 (m, 3H), 7.33 (m, 1H), 7.42-7.52 (m, 4H), 7.84 (s, 1H), (60 mg, 0.17 mmol, 34%, oil).

Example 22

1,2,3,4-tetrahydro-2-((E)-2-(6,7-dihydro-1-phenyl-1H-indazol-4(5H)-ylidene)ethyl)-isoquinoline oxalate (22)

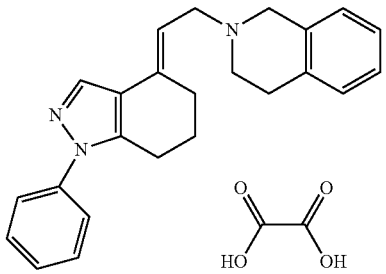 [SMILES: C(/CN1CCc2ccccc2C1)=C1/CCCc2c1cnn2-c1ccccc1 ; O=C(O)C(=O)O]

(25 mg, 0.06 mmol, 40%, white solid, m.p.=217-218° C.).

Example 23

(E)-4,5,6,7-tetrahydro-1-phenyl-4-(2-(3-phenylpiperidin-1-yl)ethylidene)-1H-indazole (23)

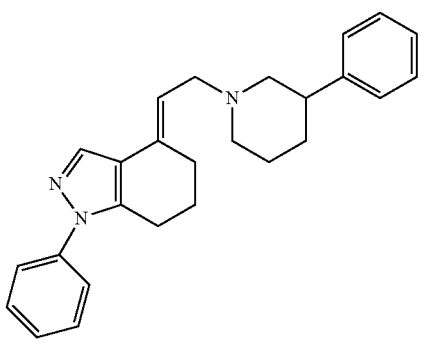 [SMILES: C(/CN1CCCC(c2ccccc2)C1)=C1/CCCc2c1cnn2-c1ccccc1]

¹H RMN (300 MHz, CDCl₃): δ 1.40-2.20 (m, 9H), 2.46 (m, 2H), 2.80 (t, J=6.2 Hz, 2H), 2.85-3.38 (m, 4H), 5.87 (t, J=7.9 Hz, 1H), 7.18-7.38 (m, 6H), 7.46 (m, 4H), 7.83 (s, 1H), (46 mg, 0.12 mmol, 24%, beige solid, m.p.=136-138° C.).

Example 24

(E)-4,5,6,7-tetrahydro-1-phenyl-4-(2-(3-phenylpyrrolidin-1-yl)ethylidene)-1H-indazole (24)

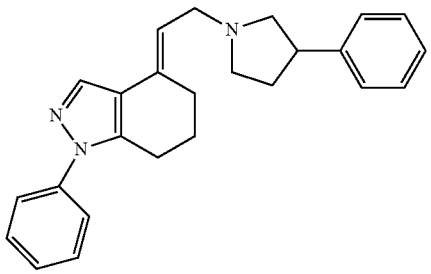 [SMILES: C(/CN1CCC(c2ccccc2)C1)=C1/CCCc2c1cnn2-c1ccccc1]

¹H RMN (300 MHz, CDCl₃): δ 1.82 (m, 2H), 1.92 (m, 1H), 2.32 (m, 1H), 2.45 (m, 2H), 2.57 (m, 1H), 2.75 (m, 3H), 3.01 (m, 1H), 3.23 (m, 1H), 3.38 (m, 3H), 5.83 (t, J=7.5 Hz, 1H), 7.09-7.30 (m, 6H), 7.34-7.46 (m, 4H), 7.77 (s, 1H), (60 mg, 0.16 mmol, 32%, oil).

Example 25

(E)-4,5,6,7-tetrahydro-1-phenyl-4-(2-(3-phenylpyrrolidin-1-yl)ethylidene)-1H-indazole oxalate (25)

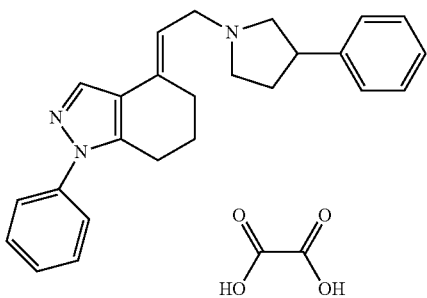 [SMILES: C(/CN1CCC(c2ccccc2)C1)=C1/CCCc2c1cnn2-c1ccccc1 ; O=C(O)C(=O)O]

(46 mg, 0.10 mmol, 67%, white solid, m.p.=178-181° C.).

Example 26

(E)-4,5,6,7-tetrahydro-4-(2-(isoindolin-2-yl)ethylidene)-1-phenyl-1H-indazole (26)

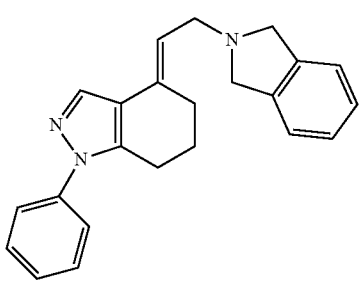 [SMILES: C(/CN1Cc2ccccc2C1)=C1/CCCc2c1cnn2-c1ccccc1]

¹H RMN (300 MHz, CDCl₃): δ 1.91 (m, 2H), 2.52 (m, 2H), 2.83 (t, J=6.1 Hz, 2H), 3.70 (d, J=7.3 Hz, 2H), 4.20 (s, 4H), 5.93 (t, J=7.3 Hz, 1H), 7.20-7.50 (m, 9H), 7.83 (s, 1H), (20 mg, 0.06 mmol, 12%, beige solid, m.p.=130-131° C.).

Example 27

(E)-4,5,6,7-tetrahydro-1-phenyl-4-(2-(piperidin-1-yl)ethylidene)-1H-indazole (27)

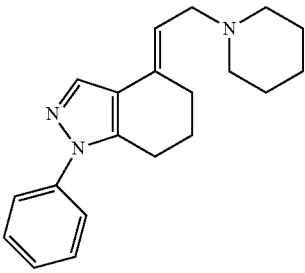 [SMILES: C(/CN1CCCCC1)=C1/CCCc2c1cnn2-c1ccccc1]

¹H RMN (300 MHz, CDCl₃): δ 1.48 (m, 2H), 1.68 (m, 4H), 1.87 (m, 2H), 2.37-2.66 (m, 6H), 2.81 (t, J=6.1 Hz, 2H), 3.22 (d, J=7.3 Hz, 2H), 5.86 (t, J=7.3 Hz, 1H), 7.32 (m, 1H), 7.41-7.50 (m, 4H), 7.83 (s, 1H), (60 mg, 0.20 mmol, 40%, beige solid, m.p.=101-104° C.).

Example 28

1-(3,4-dichlorophenyl)-4,5,6,7-tetrahydro-4-(2-(4-phenylpiperazin-1-yl)ethyl)-1H-indazole (28)

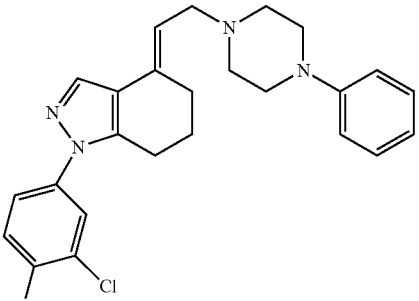

¹H RMN (300 MHz, CDCl₃): δ 1.44 (m, 1H), 1.71 (m, 2H), 1.98 (m, 3H), 2.55-2.85 (m, 9H), 3.29 (br s, 4H), 6.83-6.95 (m, 3H), 7.25 (m, 2H), 7.35 (dd, J=8.8 Hz, J=2.5 Hz, 1H), 7.49 (m, 1H), 7.53 (s, 1H), 7.64 (d, J=2.5 Hz, 1H), (75 mg, 0.16 mmol, 47%, oil).

Example 29

1-(3,4-dichlorophenyl)-4,5,6,7-tetrahydro-4-(2-(4-phenylpiperazin-1-yl)ethyl)-1H-indazole oxalate (29)

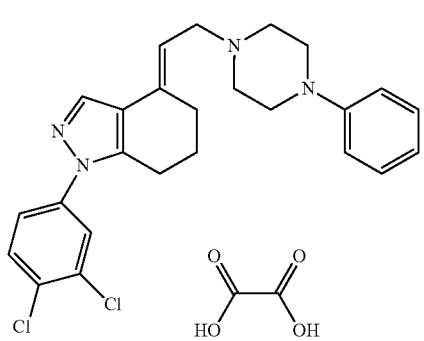 [SMILES: Clc1ccc(-n2ncc3c2CCC/C3=C\CN2CCN(c3ccccc3)CC2)cc1Cl ; O=C(O)C(=O)O]

(50 mg, 0.09 mmol, 60%, white solid, m.p.=183-184° C.).

Example 30

1,4,5,6-tetrahydro-4-(2-(morpholin-4-yl)ethyl)-1-phenylcyclopenta[c]pyrazole (30)

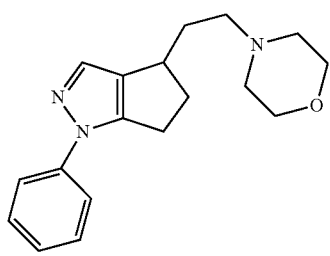 [SMILES: c1ccc(-n2ncc3c2CCC3CCN2CCOCC2)cc1]

$^1$H RMN (300 MHz, CDCl$_3$): δ 1.82 (m, 2H), 2.25 (m, 1H), 2.59 (m, 6H), 2.80 (m, 1H), 2.89-3.12 (m, 3H), 3.80 (br s, 4H), 7.23 (m, 1H), 7.37 (s, 1H), 7.41 (m, 2H), 7.61 (d, J=8.2 Hz, 2H), (114 mg, 0.38 mmol, 72%, oil).

Example 31

1,4,5,6-tetrahydro-4-(2-(morpholin-4-yl)ethyl)-1-phenylcyclopenta[c]pyrazole oxalate (31)

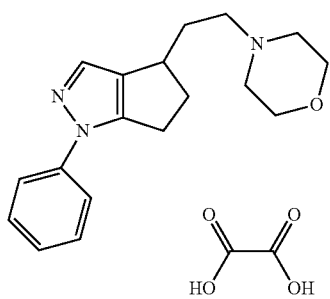 [SMILES: c1ccc(-n2ncc3c2CCC3CCN2CCOCC2)cc1 ; O=C(O)C(=O)O]

(98 mg, 0.25 mmol, 71%, beige solid, m.p.=159.0-161.8).

Example 32

4,5,6,7-tetrahydro-1-phenyl-4-(2-(4-phenylpiperazin-1-yl)ethyl)-1H-indazole (32)

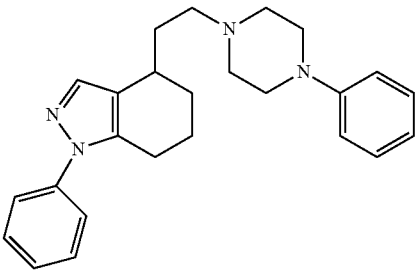 [SMILES: c1ccc(N2CCN(CCC3CCCc4c3cnn4-c3ccccc3)CC2)cc1]

$^1$H RMN (300 MHz, CDCl$_3$): δ 1.44 (m, 1H), 1.62-1.78 (m, 2H), 1.99 (m, 3H), 2.58 (m, 2H), 2.63-2.75 (m, 6H), 2.80 (m, 1H), 3.23 (m, 4H), 6.85 (t, J=7.3 Hz, 1H), 6.94 (d, J=8.8 Hz, 2H), 7.23-7.34 (m, 3H), 7.40-7.52 (m, 4H), 7.55 (s, 1H), (160 mg, 0.41 mmol, 36%, oil).

Example 33

4,5,6,7-tetrahydro-1-phenyl-4-(2-(4-phenylpiperazin-1-yl)ethyl)-1H-indazole oxalate (33)

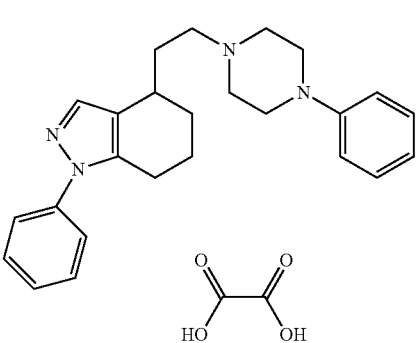 [SMILES: c1ccc(N2CCN(CCC3CCCc4c3cnn4-c3ccccc3)CC2)cc1 ; O=C(O)C(=O)O]

(150 mg, 0.31 mmol, 76%, white solid, m.p.=177-80° C.).

Example 34

2-(2-(1,4,5,6-tetrahydro-1-phenylcyclopenta[c]pyrazol-4-yl)ethyl)isoindoline (34)

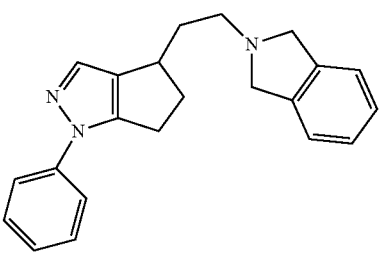 [SMILES: c1ccc(-n2ncc3c2CCC3CCN2Cc3ccccc3C2)cc1]

¹H RMN (300 MHz, CDCl₃): δ 1.97 (m, 2H), 2.30 (m, 1H), 2.85 (m, 1H), 3.01 (m, 4H), 3.17 (m, 1H), 4.16 (s, 4H), 7.23 (s, 5H), 7.23 (s, 1H), 7.42 (m, 2H), 7.63 (d, J=7.8 Hz, 2H), (93 mg, 0.28 mmol, 70%, oil).

Example 35

2-(2-(1,4,5,6-tetrahydro-1-phenylcyclopenta[c]pyrazol-4-yl)ethyl)isoindoline oxalate (35)

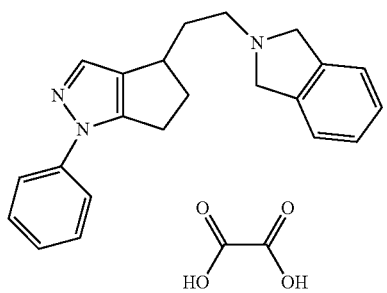 [SMILES: c1ccc(-n2ncc3c2CCC3CCN2Cc3ccccc3C2)cc1 ; O=C(O)C(=O)O]

(35 mg, 0.08 mmol, 33%, greyish solid, m.p.=195-197° C.).

Example 36

1,4,5,6-tetrahydro-1-phenyl-4-(2-(4-phenylpiperidin-1-yl)ethyl)cyclopenta[c]pyrazole (36)

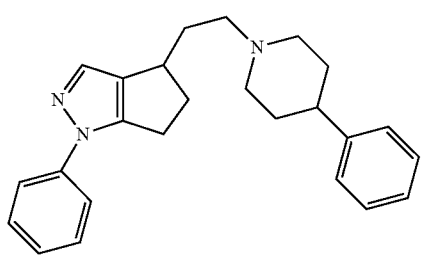 [SMILES: c1ccc(C2CCN(CCC3CCc4c3cnn4-c3ccccc3)CC2)cc1]

¹H RMN (300 MHz, CDCl₃): δ 1.63 (m, 2H), 1.90-2.18 (m, 3H), 2.35 (m, 2H), 2.52-3.20 (m, 9H), 3.69 (m, 2H), 7.20-7.46 (m, 9H), 7.61 (d, J=7.8 Hz, 2H), (41.8 mg, 0.11 mmol, 27%, beige solid, m.p.=83-86° C.).

Example 37

1,4,5,6-tetrahydro-1-phenyl-4-(2-(piperidin-1-yl)ethyl)cyclopenta[c]pyrazole (37)

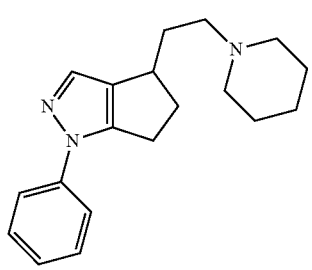 [SMILES: c1ccc(-n2ncc3c2CCC3CCN2CCCCC2)cc1]

¹H RMN (300 MHz, CDCl₃): δ 1.49 (m, 2H), 1.70 (m, 4H), 1.86 (m, 2H), 2.24 (m, 1H), 2.56 (m, 6H), 2.79 (m, 1H), 2.90-3.10 (m, 3H), 7.23 (m, 1H), 7.37 (s, 1H), 7.41 (m, 2H), 7.62 (d, J=7.9 Hz, 2H), (14 mg, 0.05 mmol, 10%, orange solid, m.p.=213-219° C.).

Example 38

1,4,5,6-tetrahydro-1-phenyl-4-(2-(4-phenylpiperazin-1-yl)ethyl)cyclopenta[c]pyrazole (38)

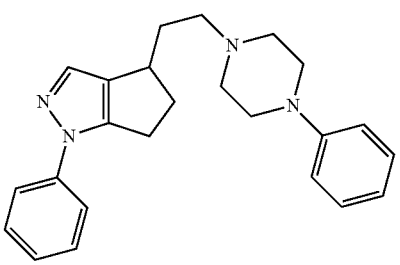 [SMILES: c1ccc(N2CCN(CCC3CCc4c3cnn4-c3ccccc3)CC2)cc1]

¹H RMN (300 MHz, CDCl₃): δ 1.82 (m, 2H), 2.24 (m, 1H), 2.58 (m, 2H), 2.68 (m, 4H), 2.80 (m, 1H), 2.90-3.20 (m, 3H), 3.24 (m, 4H), 6.86 (m, 1H), 6.94 (d, J=8.1 Hz, 2H), 7.22-7.30 (m, 3H), 7.40 (s, 1H), 7.42 (m, 2H), 7.63 (d, J=8.1 Hz, 2H), (65 mg, 0.17 mmol, 32%, beige solid, m.p.=82.5-83.5C).

Example 39

1,4,5,6-tetrahydro-1-phenyl-4-(2-(pyrrolidin-1-yl)ethyl)cyclopenta[c]pyrazole (39)

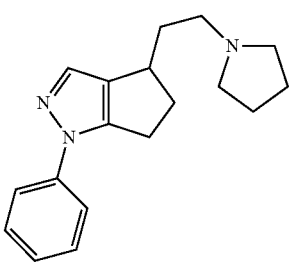 [SMILES: c1ccc(-n2ncc3c2CCC3CCN2CCCC2)cc1]

¹H RMN (300 MHz, CDCl₃): δ 1.84 (m, 6H), 3.25 (m, 1H), 2.65 (m, 6H), 2.79 (m, 1H), 2.90-3.12 (m, 3H), 7.23 (m, 1H), 7.38 (s, 1H), 7.42 (m, 2H), 7.62 (d, J=7.8 Hz, 2H), (55 mg, 0.20 mmol, 38%, oil).

Example 40

1,4,5,6-tetrahydro-1-phenyl-4-(2-(pyrrolidin-1-yl)ethyl)cyclopenta[c]pyrazole oxalate (40)

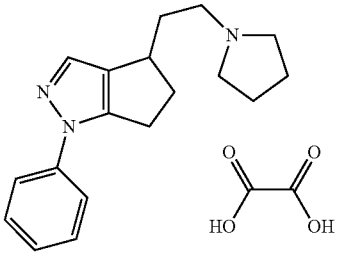

(21.5 mg, 0.06 mmol, 33%, white solid, m.p.=134, 2-136° C.).

Example 41

4-(2-(4-benzylpiperazin-1-yl)ethyl)-1,4,5,6-tetrahydro-1-phenylcyclopenta[c]pyrazole (41)

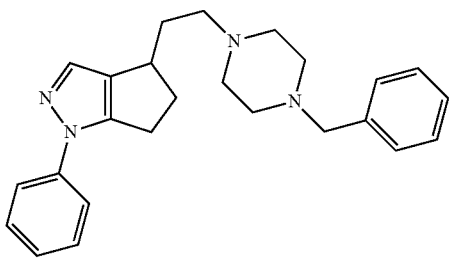 [SMILES: c1ccc(CN2CCN(CCC3CCc4c3cnn4-c3ccccc3)CC2)cc1]

$^1$H RMN (300 MHz, CDCl$_3$): δ 1.76 (m, 2H), 2.22 (m, 1H), 2.38-2.65 (m, 1H), 2.78 (m, 1H), 2.90-3.10 (m, 3H), 3.52 (s, 2H), 7, 18-739 (m, 6H), 7.41 (s, 1H), 7.44 (m, 2H), 7.62 (d, J=7.8 Hz, 2H), (124 mg, 0.33 mmol, 62%, oil).

Example 42

4-(2-(4-benzylpiperazin-1-yl)ethyl)-1,4,5,6-tetrahydro-1-phenylcyclopenta[c]pyrazole dioxalate (42)

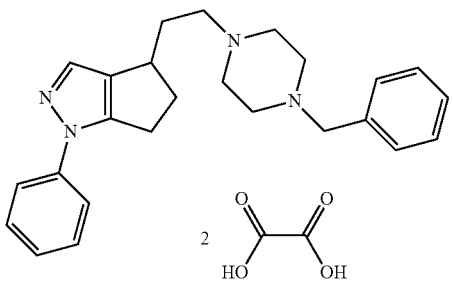 [SMILES: c1ccc(CN2CCN(CCC3CCc4c3cnn4-c3ccccc3)CC2)cc1 ; O=C(O)C(=O)O]

(149 mg, 0.26 mmol, 87%, white solid, m.p.=215-218° C.).

Example 43

1,2,3,4-tetrahydro-2-(2-(1,4,5,6-tetrahydro-1-phenylcyclopenta[c]pyrazol-4-yl)ethyl)isoquinoline (43)

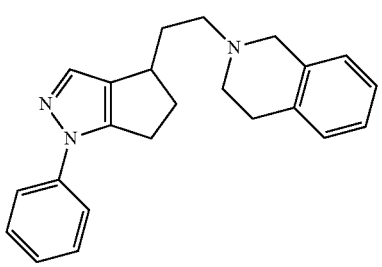 [SMILES: c1ccc(-n2ncc3c2CCC3CCN2CCc3ccccc3C2)cc1]

$^1$H RMN (300 MHz, CDCl$_3$): δ 1.86 (m, 2H), 2.28 (m, 1H), 2.65 (m, 2H), 2.70-3.18 (m, 8H), 3.66 (s, 2H), 7.03 (m, 1H), 7.11 (m, 3H), 7.23 (m, 1H), 7.41 (m, 3H), 7.63 (d, J=7.8 Hz, 2H), (73 mg, 0.21 mmol, 39%, oil).

Example 44

1,2,3,4-tetrahydro-2-(2-(1,4,5,6-tetrahydro-1-phenyl-cyclopenta[c]pyrazol-4-yl)ethyl)isoquinoline oxalate (44)

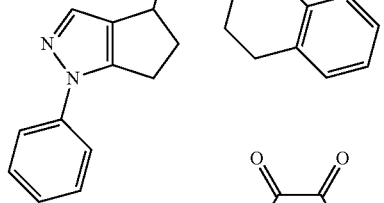

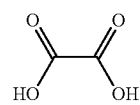

(47.9 mg, 0.11 mmol, 58%, beige solid, m.p.=200.5-203.0° C.).

Example 45

4-(2-(1H-imidazol-1-yl)ethyl)-1,4,5,6-tetrahydro-1-phenylcyclopenta[c]pyrazole (45)

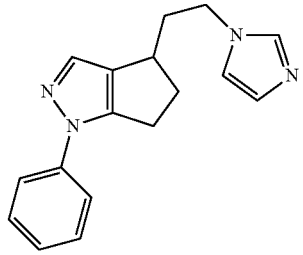 [SMILES: c1ccc(-n2ncc3c2CCC3CCn2ccnc2)cc1]

$^1$H RMN (300 MHz, CDCl$_3$): δ 2.04 (m, 2H), 2.22 (m, 1H), 2.81 (m, 1H), 2.90-3.10 (m, 3H), 4.09 (m, 2H), 6.96 (s, 1H), 7.09 (s, 1H), 7.25 (m, 1H), 7.38 (s, 1H), 7.42 (m, 2H), 7.62 (m, 3H), (65.8 mg, 0.24 mmol, 44%, orange solid, m.p.=102.9-105.7° C.).

Example 46 cis-1,4,5,6-tetrahydro-4-(2-(2,6-dimethylmorpholin-4-yl)ethyl)-1-phenylcyclopenta-[c]pyrazole (46)

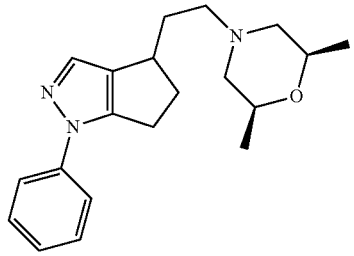 [SMILES: C[C@@H]1CN(CCC2CCc3c2cnn3-c2ccccc2)C[C@H](C)O1]

¹H RMN (300 MHz, CDCl₃): δ 1.17 (d, J=5.9 Hz, 6H), 1.78 (m, 4H), 2.23 (m, 1H), 2.48 (m, 2H), 2.82 (m, 3H), 3.02 (m, 3H), 3.74 (m, 2H), 7.23 (m, 1H), 7.38 (s, 1H), 7.42 (m, 2H), 7.62 (d, J=7.7 Hz, 2H), (220 mg, 0.68 mmol, 64%, oil).

Example 47 cis-1,4,5,6-tetrahydro-4-(2-(2,6-dimethylmorpholin-4-yl)ethyl)-1-phenylcyclopenta-[c]pyrazole oxalate (47)

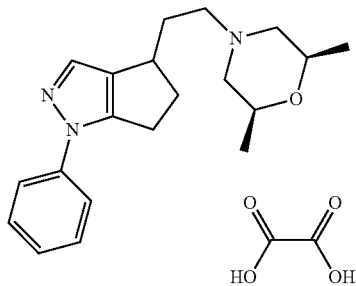

(193 mg, 0.46 mmol, 68%, white solid, m.p.=160.2-161.5° C.).

Example 48 cis-4,5,6,7-tetrahydro-4-(2-(2,6-dimethylmorpholin-4-yl)ethyl)-1-phenyl-1H-indazole (48)

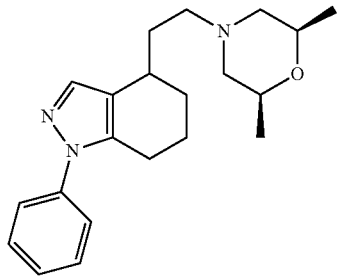 [SMILES: C[C@@H]1CN(CCC2CCCc3c2cnn3-c2ccccc2)C[C@H](C)O1]

¹H RMN (300 MHz, CDCl₃): δ 1.70 (d, J=6.3 Hz, 6H), 1.42 (m, 1H), 1.56-1.84 (m, 4H), 1.94 (m, 3H), 2.51 (m, 2H), 2.62-2.90 (m, 5H), 3.74 (m, 2H), 7.30 (m, 1H), 7.40-7.52 (m, 5H), (200 mg, 0.59 mmol, 51%, oil).

Example 49 cis-4,5,6,7-tetrahydro-4-(2-(2,6-dimethylmorpholin-4-yl)ethyl)-1-phenyl-1H-indazole oxalate (49)

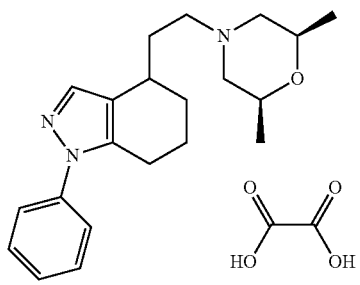

(150 mg, 0.35 mmol, 61%, white solid, m.p.=186.6-190.0° C.).

Example 50

1,4,5,6-tetrahydro-1-phenyl-4-(2-[spiro[isobenzofuran-1(3H), 4'-piperidin]-1'-yl]ethyl)cyclopenta[c]pyrazole (50)

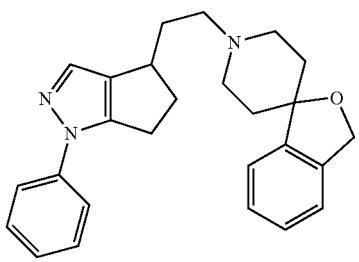

¹H RMN (300 MHz, CDCl₃): δ 1.60-1.92 (m, 4H), 2.00 (m, 2H), 2.24 (m, 1H), 2.43 (m, 2H), 2.57 (m, 2H), 2.70-3.12 (m, 6H), 5.06 (s, 2H), 7.05-7.30 (m, 5H), 7.40 (m, 3H), 7.62 (d, J=7.6 Hz, 2H), (159 mg, 0.40 mmol, 74%, oil).

Example 51

1,4,5,6-tetrahydro-1-phenyl-4-(2-[spiro[isobenzofuran-1(3H), 4'-piperidin]-1'-yl]ethyl)cyclopenta[c]pyrazole oxalate (51)

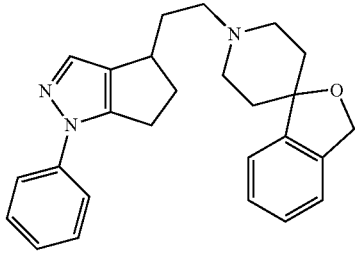 [SMILES: c1ccc(-n2ncc3c2CCC3CCN2CCC3(CC2)OCc2ccccc23)cc1]

(48.6 mg, 0.10 mmol, 25%, white solid, m.p.=170.5-173.6° C.).

Example 52

N-benzyl-2-(1,4,5,6-tetrahydro-1-phenylcyclopenta[c]pyrazol-4-yl)-N-methylethanamine (52)

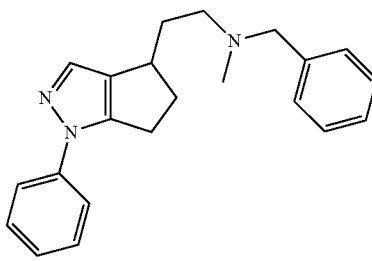

¹H RMN (300 MHz, CDCl₃): δ 1.82 (m, 2H), 2.21 (m, 1H), 2.32 (br s, 3H), 2.61 (m, 2H), 2.77 (m, 1H), 2.97 (m, 2H), 3.08 (m, 1H), 3.64 (m, 2H), 7.20-7.45 (m, 9H), 7.61 (d, J=7.8 Hz, 2H), (60 mg, 0.18 mmol, 37%, oil).

Example 53

Diastereomeric mixture of 1,4,5,6-tetrahydro-1-phenyl-4-(2-(3-phenylpiperidin-1-yl)ethyl)cyclopenta[c]pyrazole (53)

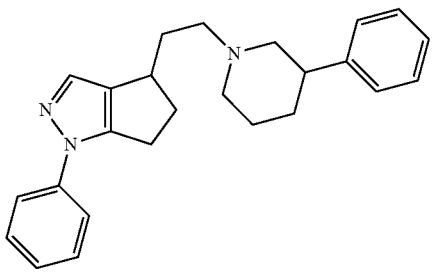 [SMILES: c1ccc(C2CCCN(CCC3CCc4c3cnn4-c3ccccc3)C2)cc1]

(128 mg, 0.35 mmol, 65%, oil).

Example 54

N-benzyl-2-(4,5,6,7-tetrahydro-1-phenyl-1H-indazol-4-yl)-N-methylethanamine (54)

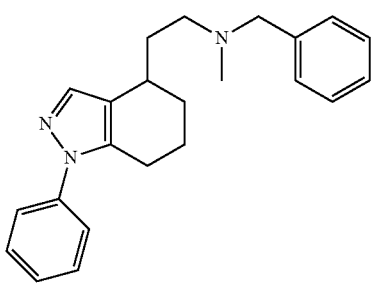 [SMILES: CN(CCC1CCCc2c1cnn2-c1ccccc1)Cc1ccccc1]

¹H RMN (300 MHz, CDCl₃): δ 1.39 (m, 1H), 1.67 (m, 2H), 1.93 (m, 3H), 2.29 (s, 3H), 2.60 (m, 2H), 2.69 (m, 2H), 2.81 (m, 1H), 3.59 (m, 2H), 7.20-7.53 (m, 11H), (149.7 mg, 0.43 mmol, 45%, oil).

Example 55

4,5,6,7-tetrahydro-4-(2-(isoindolin-2-yl)ethyl)-1-phenyl-1H-indazole (55)

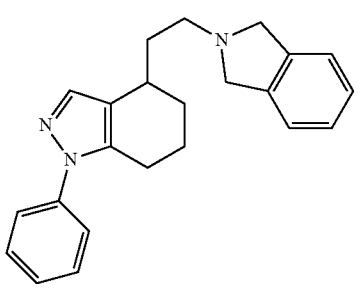 [SMILES: c1ccc(-n2ncc3c2CCCC3CCN2Cc3ccccc3C2)cc1]

¹H RMN 300 MHz, CDCl₃): δ 1.48 (m, 1H), 1.62-1.909 (m, 2H), 1.92-2.15 (m, 3H), 2.72 (br s, 2H), 2.83-3.05 (m, 3H), 4.09 (s, 4H), 7.16-7.39 (m, 5H), 7.40-7.60 (m, 5H), (201 mg, 0.59 mmol, 62%, oil).

Example 56

4,5,6,7-tetrahydro-4-(2-(isoindolin-2-yl)ethyl)-1-phenyl-1H-indazole oxalate (56)

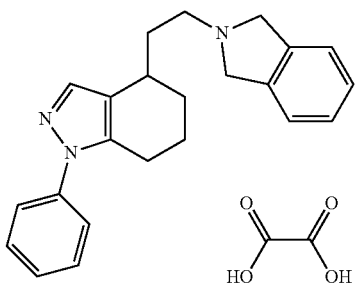 [SMILES: c1ccc(-n2ncc3c2CCCC3CCN2Cc3ccccc3C2)cc1 ; O=C(O)C(=O)O]

(146.9 mg, 0.34 mmol, 60%, greyish solid, m.p.=195.7-200.0° C.).

Example 57

4,5,6,7-tetrahydro-1-methyl-4-(2-(4-phenylpiperidin-1-yl)ethyl)-1H-indazole (57)

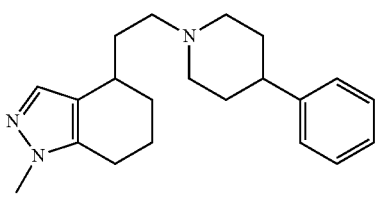 [SMILES: Cn1ncc2c1CCCC2CCN1CCC(c2ccccc2)CC1]

¹H RMN (300 MHz, CDCl₃): δ 1.39 (m, 1H), 1.63-2.40 (m, 11H), 2.42-2.78 (m, 6H), 3.24 (m, 2H), 3.71 (s, 3H), 7.18-7.38 (m, 6H), (158 mg, 0.49 mmol, 39%, white solid, m.p.=63-70° C.).

Example 58

4,5,6,7-tetrahydro-1-methyl-4-(2-(4-phenylpiperidin-1-yl)ethyl)-1H-indazole oxalate (58)

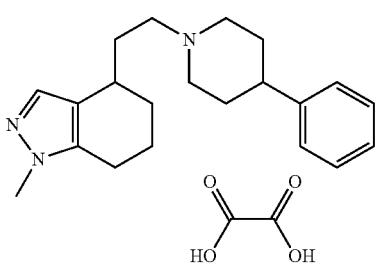

(77.5 mg, 0.19 mmol, 40%, white solid, m.p.=117.3-120.5° C.).

Example 59

4,5,6,7-tetrahydro-4-(2-(isoindolin-2-yl)ethyl)-1-methyl-1H-indazole (59)

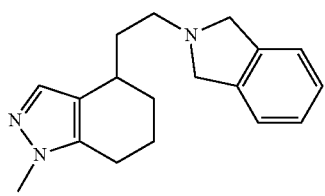 [SMILES: Cn1ncc2c1CCCC2CCN1Cc2ccccc2C1]

$^1$H RMN (300 MHz, CDCl$_3$): δ 1.40 (m, 1H), 1.76 (m, 2H), 1.98 (m, 3H), 2.54 (br s, 2H), 2.79 (m, 1H), 2.93 (m, 2H), 3.71 (s, 3H), 4.08 (m, 4H), 7.18-7.40 (m, 5H), (96.4 mg, 0.34 mmol, 45%, oil).

Example 60

4,5,6,7-tetrahydro-4-(2-(isoindolin-2-yl)ethyl)-1-methyl-1H-indazole oxalate (60)

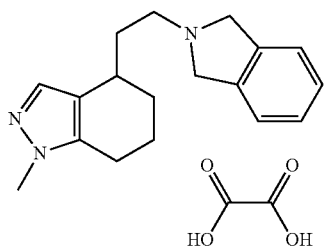

(51 mg, 0.14 mmol, 45%, greyish solid, m.p.=150-151° C.).

Example 61

N-benzyl-2-(4,5,6,7-tetrahydro-1-methyl-1H-indazol-4-yl)-N-methylethanamine (61)

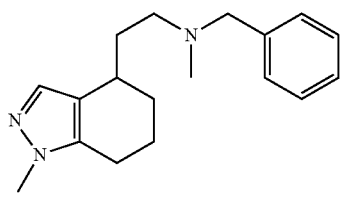 [SMILES: CN(CCC1CCCc2c1cnn2C)Cc1ccccc1]

$^1$H RMN (300 MHz, CDCl$_3$): δ 1.30 (m, 1H), 1.68 (m, 2H), 1.92 (m, 3H), 2.27 (s, 3H), 2.42-2.62 (m, 4H), 2.69 (m, 1H), 3.60 (m, 2H), 3.70 (s, 3H), 7.20-7.42 (m, 6H), (90.8 mg, 0.32 mmol, 43%, oil).

Example 62

N-benzyl-2-(4,5,6,7-tetrahydro-1-methyl-1H-indazol-4-yl)-N-methylethanamine oxalate (62)

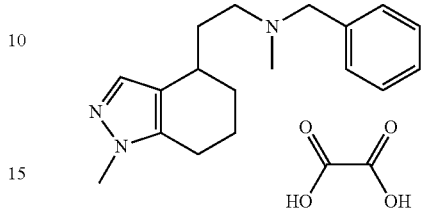

(42.6 mg, 0.11 mmol, 37%, white solid, m.p.=140.2-141.7° C.).

Example 63

4,5,6,7-tetrahydro-1-methyl-4-(2-(morpholin-4-yl)ethyl)-1H-indazole (63)

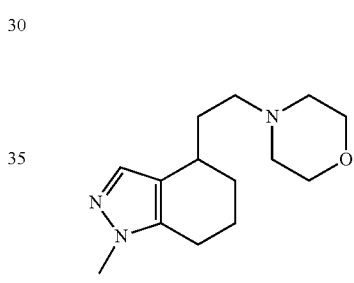

$^1$H RMN (300 MHz, CDCl$_3$): δ 1.35 (m, 1H), 1.65 (m, 2H), 1.92 (m, 3H), 2.42-2.60 (m, 8H), 2.66 (m, 1H), 3.71 (s, 3H), 3.75 (m, 4H), 7.27 (s, 1H), (60.8 mg, 0.24 mmol, 32%, oil).

Example 64

4,5,6,7-tetrahydro-1-methyl-4-(2-(morpholin-4-yl)ethyl)-1H-indazole oxalate (64)

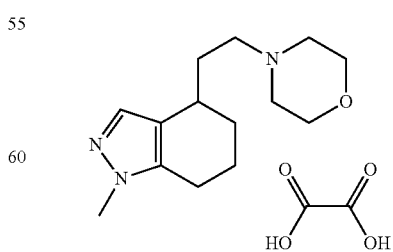

(22 mg, 0.06 mmol, 30%, white solid, m.p.=137.7-139.3° C.).

Example 65

1-(4-fluorophenyl)-4,5,6,7-tetrahydro-4-(2-(morpholin-4-yl)ethyl)-1H-indazole (65)

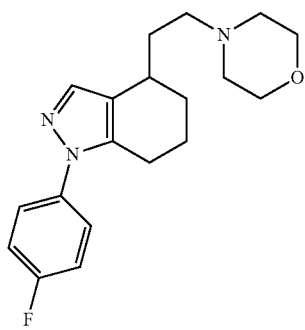 [SMILES: Fc1ccc(-n2ncc3c2CCCC3CCN2CCOCC2)cc1]

¹H RMN (300 MHz, CDCl₃): δ 1.43 (m, 1H), 1.69 (m, 2H), 1.94 (m, 3H), 2.52 (m, 6H), 2.65 (m, 2H), 2.77 (m, 1H), 3.75 (m, 4H), 7.13 (m, 2H), 7.44 (dd, J=9.2 Hz, J'=4.8 Hz, 2H), 7.50 (s, 1H), (84 mg, 0.25 mmol, 46%, oil).

Example 66

1-(4-fluorophenyl)-4,5,6,7-tetrahydro-4-(2-(morpholin-4-yl)ethyl)-1H-indazole oxalate (66)

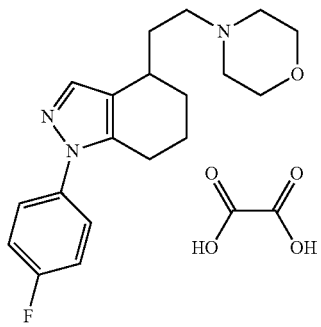

(67 mg, 0.16 mmol, 70%, white solid, m.p.=148-151° C.).

Example 67 cis-1-(4-fluorophenyl)-4,5,6,7-tetrahydro-4-(2-(2,6-dimethylmorpholin-4-yl)ethyl)-1H-indazole (67)

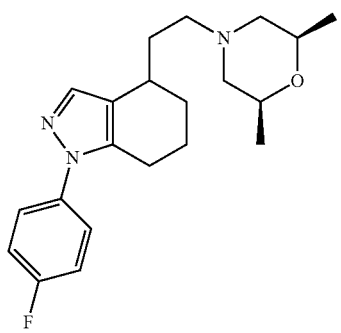 [SMILES: C[C@@H]1CN(CCC2CCCc3c2cnn3-c2ccc(F)cc2)C[C@H](C)O1]

¹H RMN (300 MHz, CDCl₃): δ 1.17 (d, J=6.3 Hz, 6H), 1.41 (m, 1H), 1.60-1.81 (m, 4H), 1.94 (m, 3H), 2.48 (t, J=7.7 Hz, 2H), 2.65 (m, 2H), 2.71-2.86 (m, 3H), 3.71 (m, 2H), 7.13 (m, 2H), 7.44 (dd, J=9.1 Hz, J'=4.8 Hz, 2H), 7.50 (s, 1H), (114 mg, 0.32 mmol, 59%, oil).

Example 68 cis-1-(4-fluorophenyl)-4,5,6,7-tetrahydro-4-(2-(2,6-dimethylmorpholin-4-yl)ethyl)-1H-indazole oxalate (68)

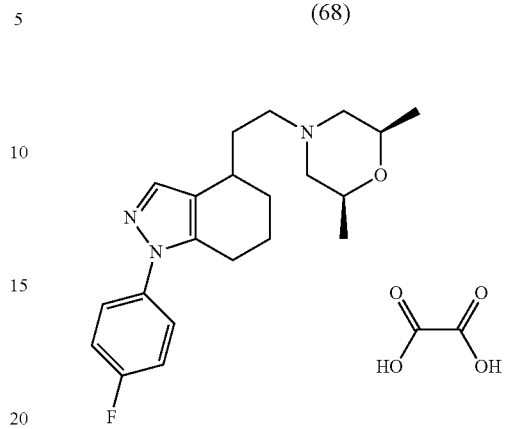

(86 mg, 0.19 mmol, 63%, white solid, m.p.=164-169° C.).

Example 69

N-benzyl-2-(1-(4-fluorophenyl)-4,5,6,7-tetrahydro-1H-indazol-4-yl)-N-methylethanamine (69)

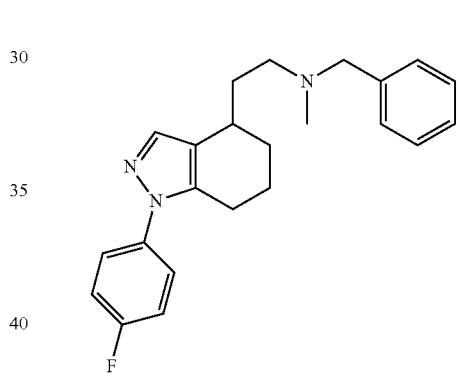

¹H RMN (300 MHz, CD₃OD): δ 1.42 (m, 1H), 1.70 (m, 2H), 1.96 (m, 3H), 2.29 (s, 3H), 2.54-2.67 (m, 4H), 2.57 (m, 1H), 3.59 y 3.61 (AB System, J$_{AB}$=12.8 Hz, 2H), 7.21-7.40 (m, 7H), 7.43-7.56 (m, 3H), (100 mg, 0.28 mmol, 52%, oil).

Example 70

1-(4-fluorophenyl)-4,5,6,7-tetrahydro-4-(2-(isoindolin-2-yl)ethyl)-1H-indazole (70)

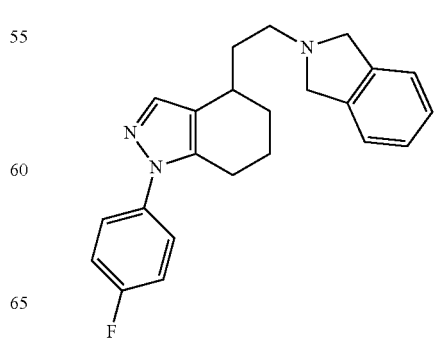

$^1$H RMN (300 MHz, CDCl$_3$): δ 1.48 (m, 1H), 1.74 (m, 2H), 2.00 (m, 3H), 2.67 (m, 2H), 2.82-2.94 (m, 3H), 4.00 (s, 4H), 7.13 (m, 2H), 7.21 (m, 4H), 7.46 (dd, J=8.9 Hz, J'=4.8 Hz, 2H), 7.55 (s, 1H), (117 mg, 0.32 mmol, 59%, oil).

Example 71

1-(4-fluorophenyl)-4,5,6,7-tetrahydro-4-(2-(isoindolin-2-yl)ethyl)-1H-indazole oxalate (71)

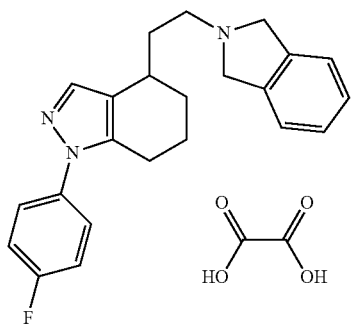 [SMILES: Fc1ccc(-n2ncc3c2CCCC3CCN2Cc3ccccc3C2)cc1 ; O=C(O)C(=O)O]

(55 mg, 0.12 mmol, 40%, greyish solid, m.p.=176-179° C.).

Example 72

1-(4-fluorophenyl)-4,5,6,7-tetrahydro-4-(2-(4-phenylpiperidin-1-yl)ethyl)-1H-indazole (72)

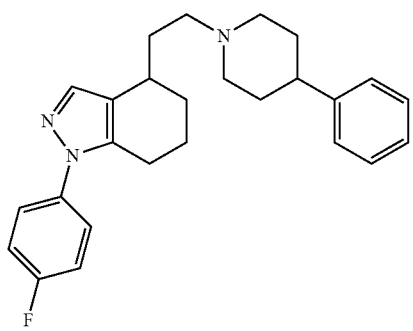 [SMILES: Fc1ccc(-n2ncc3c2CCCC3CCN2CCC(c3ccccc3)CC2)cc1]

$^1$H RMN (300 MHz, CDCl$_3$): δ 1.47 (m, 1H), 1.71 (m, 1H), 1.80-2.95 (m, 16H), 3.41 (m, 2H), 7.13 (m, 2H), 7.20-7.38 (m, 5H), 7.44 (dd, J=9.1 Hz, J'=4.8 Hz, 2H), 7.51 (s, 1H), (65 mg, 0.16 mmol, 30%, beige solid, m.p.=93-94.5° C.).

Chiral Separation of Example 1

The enantiomeric separation of the racemic compound 4,5,6,7-tetrahydro-4-(2-(morpholin-4-yl)ethyl)-1-phenyl-1H-indazole (Example 1) is carried out by chiral semi-preparative HPLC, using a Chiralpak AS, 10 microm. p.s. 25×2 cm column from Daicel. The mobile phase used is n-hexane/ethanol 95/5 v/v at a flow rate of 13 mL/min.

Compound's Data:

1$^{st}$ Peak: retention time=11.5 min (examples 73 and 74).

Example 73

(+)-4,5,6,7-tetrahydro-4-(2-(morpholin-4-yl)ethyl)-1-phenyl-1H-indazole

Oil, [alpha]$_D^{20}$+4.3 (c=1, CHCl$_3$), ee>99.9%.

Example 74

(+)-4,5,6,7-tetrahydro-4-(2-(morpholin-4-yl)ethyl)-1-phenyl-1H-indazole oxalate 102 mg, white solid, m.p.=175-176° C., [alpha]$_D^{20}$+1.7 (c=1, MeOH), ee 99.5%.

2$^{nd}$ Peak: retention time=13.2 min (examples 75 and 76).

Example 75

(−)-4,5,6,7-tetrahydro-4-(2-(morpholin-4-yl)ethyl)-1-phenyl-1H-indazole

Oil, [alpha]$_D^{20}$-5.8 (c=1, CHCl$_3$), ee>98.4%.

Example 76

(−)-4,5,6,7-tetrahydro-4-(2-(morpholin-4-yl)ethyl)-1-phenyl-1H-indazole oxalate 104 mg, white solid, m.p.=175-176° C., [alpha]$_D^{20}$-1.3 (c=1, MeOH), ee>98.4%).

Example 77

(E)-4,5,6,7-tetrahydro-4-(2-(morpholin-4-yl)ethylidene)-1-phenyl-1H-indazole oxalate (77)

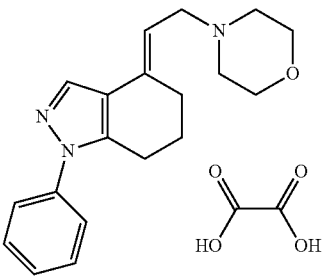

(127 mg, 0.32 mmol, 16.7%, white solid, p.f.=156-157° C.)

Example 78

(E)-4,5,6,7-tetrahydro-1-phenyl-4-(2-(piperidin-1-yl)ethylidene)-1H-indazole oxalate (78)

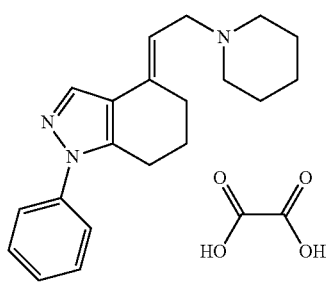

(82 mg, 0.21 mmol, 29.1%, white solid, p.f.=188-189° C.)

Example 79

Synthesis of (E)-N-benzyl-2-(6,7-dihydro-1-phenyl-1H-indazol-4(5H)-ylidene)-N-ethyl-ethanamine (79)

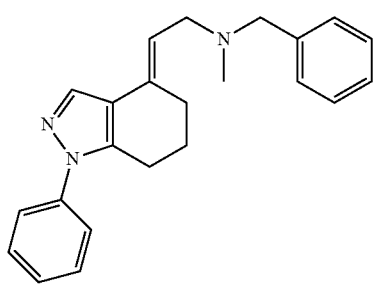 [SMILES: CN(C/C=C1\CCCc2c1cnn2-c1ccccc1)Cc1ccccc1]

Method C

Step 1: Synthesis of (E)-2-(1,5,6,7-tetrahydro-1-phenyl-4H-indazol-4-ylidene)acetaldehyde

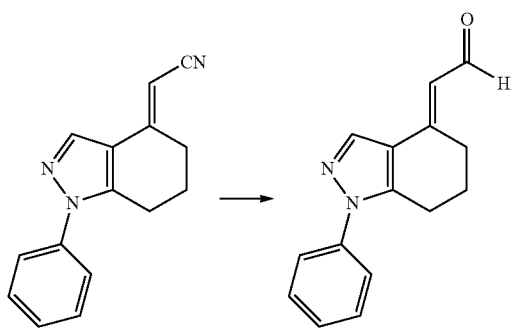 [SMILES: N#C/C=C1\CCCc2c1cnn2-c1ccccc1 ; O=C/C=C1\CCCc2c1cnn2-c1ccccc1]

A solution of 1M diisobutyl aluminium hydride in toluene (0.7 mL, 0.7 mmol) is slowly added to a solution of (E)-2-(1,5,6,7-tetrahydro-1-phenyl-4H-indazol-4-ylidene)acetonitrile (120 mg, 0.51 mmol) in methylene chloride (5 mL) cooled to 0° C. and is maintained at this temperature for 3 hours following the TLC reaction. Water and a 0.5 N HCl solution and the insoluble solid are filtered. The mixture is diluted in methylene chloride and is washed with water and with a sodium chloride saturated solution. The phase is eliminated under reduced pressure and the resulting crude is purified by means of silica gel chromatography, giving (E)-2-(1,5,6,7-tetrahydro-1-phenyl-4H-indazol-4-ylidene)acetaldehyde (74.5 mg, 0.31 mmol, 61%, oil).

$^1$H NMR (300 MHz, CDCl$_3$): δ 2.02 (m, 2H), 2.91 (m, 2H), 3.05 (m, 2H), 6.31 (d, J=8.1 Hz, 1H), 7.35-7.55 (m, 5H), 7.93 (s, 1H), 10.11 (d, J=8.1 Hz, 1H).

When the reaction is carried out with the mixture of E/Z isomers of 2-(1,5,6,7-tetrahydro-1-phenyl-4H-indazol-4-ylidene)acetonitrile, a mixture of E/Z isomers of 2-(1,5,6,7-tetrahydro-1-phenyl-4H-indazol-4-ylidene)acetaldehyde is obtained.

Step 2: Synthesis of (E)-N-benzyl-2-(6,7-dihydro-1-phenyl-1H-indazol-4(5H)-ylidene)-N-methylethanamine

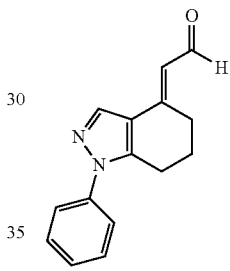

A solution of (E)-2-(1,5,6,7-tetrahydro-1-phenyl-4H-indazol-4-ylidene) acetaldehyde (299 mg, 1.25 mmol) and N-benzylmethylamine (0.18 mL, 1.38 mmol) in methanol (20 mL) cooled to 0° C. is left stirring for 20 minutes. Then sodium cyanoborohydride (213 mg, 3.39 mmol) at 0° C. is added, and then it is left to increase to room temperature following the TLC reaction. The solvent is evaporated at reduced pressure, diluted in ethyl acetate, washed with water and with sodium chloride saturated solution, dried and evaporated under reduced pressure. The resulting crude product is purified by means of silica gel chromatography, giving (E)-N-benzyl-2-(6,7-dihydro-1-phenyl-1H-indazol-4(5H)-ylidene)-N-methylethanamine (158 mg, 0.46 mmol, 36%, oil).

$^1$H NMR (300 MHz, CDCl$_3$): δ 1.87 (m, 2H), 2.27 (s, 3H), 2.45 (m, 2H), 2.81 (t, J=6.1 Hz, 2H), 3.23 (d, J=6.9 Hz, 2H), 3.59 (s, 2H), 5.88 (m, 1H), 7.20-7.50 (m, 10H), 7.83 (s, 1H),

When the reaction is carried out with the mixture of E/Z isomers of 2-(1,5,6,7-tetrahydro-1-phenyl-4H-indazol-4-ylidene)acetaldehyde, a mixture of E/Z isomers of N-benzyl-2-(6,7-dihydro-1-phenyl-1H-indazol-4(5H)-ylidene)-N-methylethanamine is obtained.

$^1$H RMN (300 MHz, CDCl$_3$): δ 1.87 (m, 2H), 2.27 (s, 3H), 2.45 (m, 2H), 2.81 (t, J=6.1 Hz, 2H), 3.23 (d, J=6.9 Hz, 2H), 3.59 (s, 2H), 5.88 (m, 1H), 7.20-7.50 (m, 10H), 7.83 (s, 1H), (158 mg, 0.46 mmol, 26%, oil).

Example 80

(E)-N-benzyl-2-(6,7-dihydro-1-phenyl-1H-indazol-4 (5H)-ylidene)-N-methylethanamine oxalate (80)

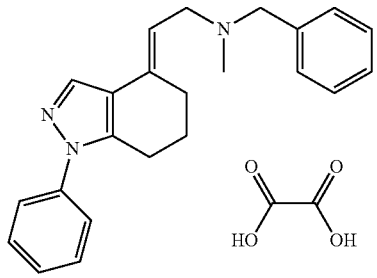 [SMILES: CN(C/C=C1\CCCc2c1cnn2-c1ccccc1)Cc1ccccc1 ; O=C(O)C(=O)O]

(118 mg, 0.27 mmol, 59%, p.f.=107-108° C., yellow solid).

Example 81

(E)-4,5,6,7-tetrahydro-4-(2-(cis-2,6-dimethylmorpholin-4-yl)ethylidene)-1-phenyl-1H-indazole (81)

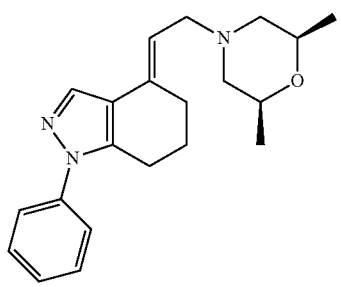 [SMILES: C[C@@H]1CN(C/C=C2\CCCc3c2cnn3-c2ccccc2)C[C@H](C)O1]

$^1$H RMN (300 MHz, CDCl$_3$): δ 1.17 (d, J=6.3 Hz, 6H), 1.80 (m, 4H), 2.48 (m, 2H), 2.84 (m, 4H), 3.19 (d, J=6.4 Hz, 2H), 3.77 (m, 2H), 5.82 (m, 1H), 7.35 (m, 1H), 7.46 (m, 4H), 7.83 (s, 1H), (84 mg, 0.25 mmol, 15%, oil).

Example 82

(E)-4,5,6,7-tetrahydro-4-(2-(cis-2,6-dimethylmorpholin-4-yl)ethylidene)-1-phenyl-1H-indazole oxalate (82)

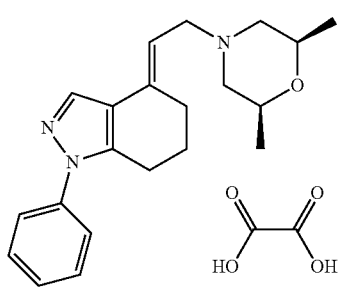

(40 mg, 0.09 mmol, 37%, p.f.=133-136° C., yellow solid).

Example 83

(E)-1-(3,4-dichlorophenyl)-4,5,6,7-tetrahydro-4-(2-(cis-2,6-dimethylmorpholino-4-yl)ethylidene)-1H-indazole (83)

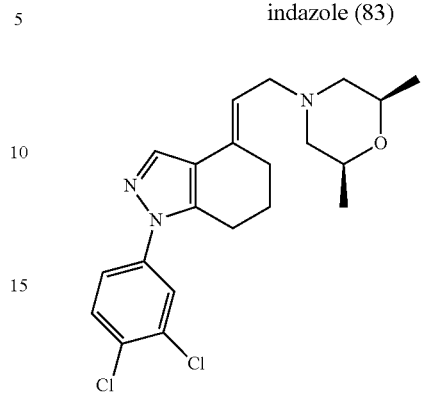

$^1$H RMN (300 MHz, CDCl$_3$): δ 1.15 (d, J=6.2 Hz, 6H), 1.87 (m, 4H), 2.45 (m, 2H), 2.75-2.93 (m, 4H), 3.21 (m, 2H), 3.79 (m, 2H), 5.81 (m, 1H), 7.35 (m, 1H), 7.49 (m, 1H), 7.62 (m, 1H), 7.81 (s, 1H),
(95 mg, 0.23 mmol, 72%, yellowish oil).

Example 84

(E)-1-(3,4-dichlorophenyl)-4,5,6,7-tetrahydro-4-(2-(cis-2,6-dimethylmorpholino-4-yl)ethylidene)-1H-indazole oxalate (84)

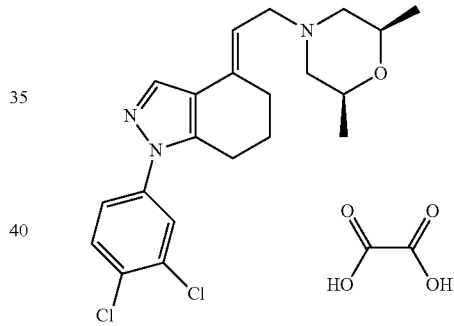

(59 mg, 0.12 mmol, 51%, p.f.=129-130° C., white solid).

Example 85

(E)-1-(3,4-dichlorophenyl)-4,5,6,7-tetrahydro-4-(2-(morpholino-4-yl)ethylidene)-1H-indazole (85)

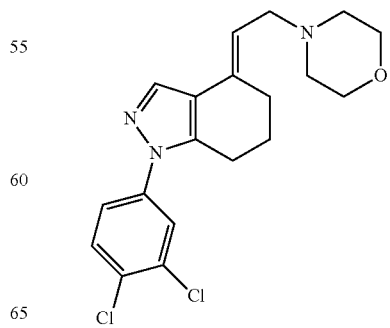

¹H RMN (300 MHz, CDCl₃): δ 1.89 (m, 2H), 2.40-2.63 (m, 6H), 2.81 (t, J=6.1 Hz, 2H), 3.21 (d, J=7.2 Hz, 2H), 3.78 (m, 4H), 5.82 (t, J=6.1 Hz, 1H), 7.35 (dd, J=8.6 Hz, J'=2.2 Hz, 1H), 7.52 (d, J=8.6 Hz, 1H), 7.64 (d, J=2.2 Hz, 1H), 7.81 (s, 1H), (97 mg, 0.26 mmol, 79%, yellowish oil).

Example 86

(E)-1-(3,4-dichlorophenyl)-4,5,6,7-tetrahydro-4-(2-(morpholino-4-yl)ethylidene)-1H-indazole oxalate (86)

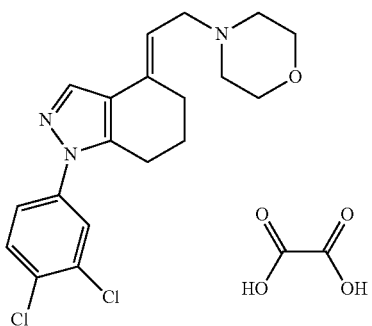 [SMILES: Clc1ccc(-n2ncc3c2CCC/C3=C\CN2CCOCC2)cc1Cl ; O=C(O)C(=O)O]

(66 mg, 0.14 mmol, 54%, p.f.=170-172° C., white solid).

Example 87

(E)-1-(3,4-dichlorophenyl)-4,5,6,7-tetrahydro-4-(2-(piperidin-1-yl)ethylidene)-1H-indazole (87)

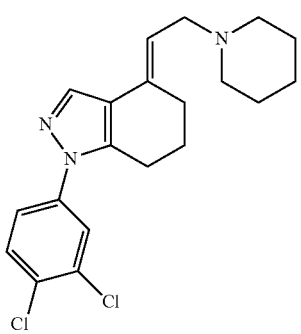 [SMILES: Clc1ccc(-n2ncc3c2CCC/C3=C\CN2CCCCC2)cc1Cl]

(42 mg, 0.11 mmol, 48%, yellowish oil).

Example 88

(E)-1-(3,4-dichlorophenyl)-4,5,6,7-tetrahydro-4-(2-(piperidin-1-yl)ethylidene)-1H-indazole oxalate (88)

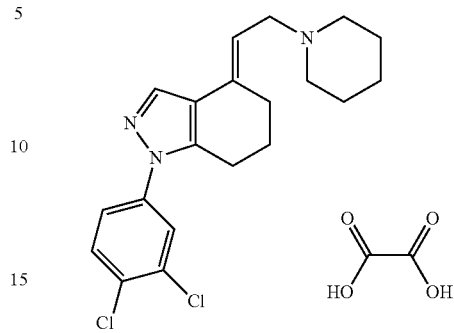

¹H RMN (300 MHz, CD₃OD): δ 1.40-2.05 (m, 8H), 2.62 (m, 2H), 2.88-3.10 (m, 4H), 3.53 (m, 2H), 3.90 (d, J=7.6 Hz, 2H), 5.86 (m, 1H), 7.51 (dd, J=8.6 Hz, r=2.3 Hz, 1H), 7.70 (d, J=8.6 Hz, 1H), 7.78 (d, J=2.3 Hz, 1H), 8.01 (s, 1H), (12 mg, 0.03 mmol, 16%, p.f.=100-102° C., white solid).

Example 89

(E)-4-(2-(N,N-diethylamino)ethylidene)-4,5,6,7-tetrahydro-1-phenyl-1H-indazole (89)

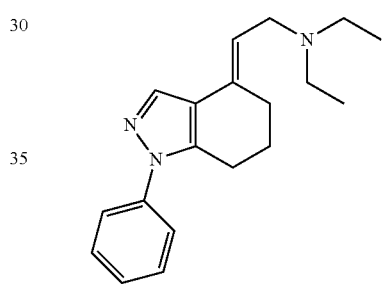

¹H RMN (300 MHz, CDCl₃): δ 1.14 (t, J=7.2 Hz, 6H), 1.89 (m, 2H), 2.49 (m, 2H), 2.67 (q, J=7.2 Hz, 4H), 2.82 (t, J=6.0 Hz, 2H), 3.36 (d, J=7.0 Hz, 2H), 5.83 (t, J=7.0 Hz, 1H), 7.32 (m, 1H), 7.40-7.50 (m, 4H), 7.83 (s, 1H), (68.8 mg, 0.23 mmol, 27.7%, oil).

Example 90

(E)-4-(2-(N,N-diethylamino)ethylidene)-4,5,6,7-tetrahydro-1-phenyl-1H-indazole oxalate (90)

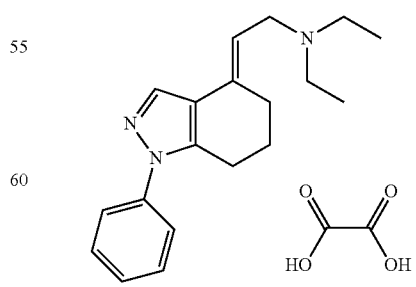

(34.2 mg, 0.09 mmol, 10.6%, p.f.=163-164° C., yellowish solid).

Example 91

(E)-4-(2-(4-cyclohexylpiperazin-1-yl)ethylidene)-4,5,6,7-tetrahydro-1-phenyl-1H-indazole (91)

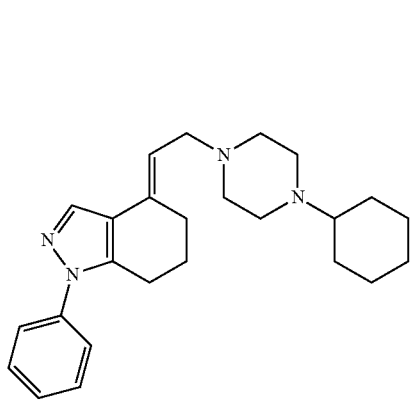 [SMILES: C(/CN1CCN(C2CCCCC2)CC1)=C1/CCCc2c1cnn2-c1ccccc1]

$^1$H RMN (300 MHz, CDCl$_3$): δ 1.05-1.32 (m, 5H), 1.58-2.01 (m, 7H), 2.30 (m, 1H), 2.40-2.75 (m, 10H), 2.81 (t, J=6.0 Hz, 2H), 3.17 (d, J=7.3 Hz, 2H), 5.83 (t, J=7.3 Hz, 1H), 7.33 (m, 1H), 7.47 (m, 4H), 7.81 (s, 1H), (81 mg, 0.21 mmol, 25%, p.f.=124-130° C., yellowish solid).

Example 92

(E)-4,5,6,7-tetrahydro-4-(2-(4-methylpiperidin-1-yl)ethylidene)-1-phenyl-1H-indazole (92)

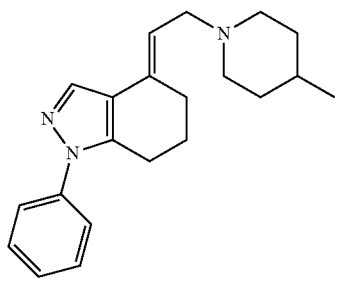 [SMILES: CC1CCN(C/C=C2\CCCc3c2cnn3-c2ccccc2)CC1]

$^1$H RMN (300 MHz, CDCl$_3$): δ 0.93 (d, J=6.0 Hz, 3H), 1.28 (m, 3H), 1.65 (m, 2H), 1.82-2.03 (m, 4H), 2.47 (m, 2H), 2.81 (t, J=6.1 Hz, 2H), 2.97 (m, 2H), 3.14 (d, J=7.2 Hz, 2H), 5.86 (t, J=7.2 Hz, 1H), 7.53 (m, 1H), 7.40-7.50 (m, 4H), 7.82 (s, 1H), (30 mg, 0.09 mmoles, 11%, p.f.=83-90° C., white solid)

Example 93

Synthesis of 4,5,6,7-tetrahydro-4-(2-(4-methylpiperidin-1-yl)ethyl)-1-phenyl-1H-indazole (93)

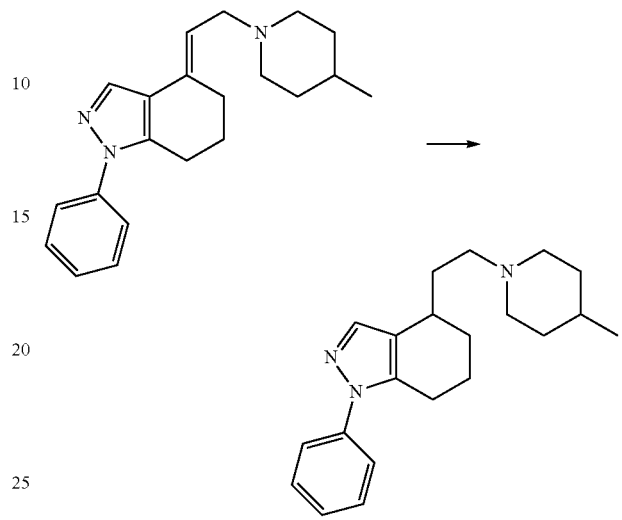

Method E:

Pd—C (100 mg, 20%) is added to a solution of a mixture of E/Z isomers of 4,5,6,7-tetrahydro-4-(2-(4-methylpiperidin-1-yl)ethylidene)-1-phenyl-1H-indazole (324 mg, 1.01 mmol) in 75 mL of EtOH, and the resulting solution is stirred in a nitrogen atmosphere (45 psi) in a Parr hydrogenator for 18 hours. The reaction mixture is purged with nitrogen, filtered through Celite and the solvent is evaporated under reduced pressure. The resulting crude product is purified by means of silica gel chromatography giving 4,5,6,7-tetrahydro-4-(2-(4-methylpiperidin-1-yl)ethyl)-1-phenyl-1H-indazole (130 mg, 0.40 mmol, 40%, oil).

$^1$H NMR (300 MHz, CDCl$_3$): δ 1.00 (d, J=6.3 Hz, 3H), 1.40-2.25 (m, 11H), 2.50 (m, 2H), 2.69 (m, 2H), 2.80-3.00 (m, 3H), 3.40 (m, 2H), 7.33 (m, 1H), 7.46 (m, 4H), 7.49 (s, 1H).

$^1$H RMN (300 MHz, CDCl$_3$): δ 1.00 (d, J=6.3 Hz, 3H), 1.40-2.25 (m, 11H), 2.50 (m, 2H), 2.69 (m, 2H), 2.80-3.00 (m, 3H), 3.40 (m, 2H), 7.33 (m, 1H), 7.46 (m, 4H), 7.49 (s, 1H). (130 mg, 0.40 mmoles, 40%, oil)

Example 94

4,5,6,7-Tetrahydro-4-(2-(4-methylpiperidin-1-yl)ethyl)-1-phenyl-1H-indazole oxalate (94)

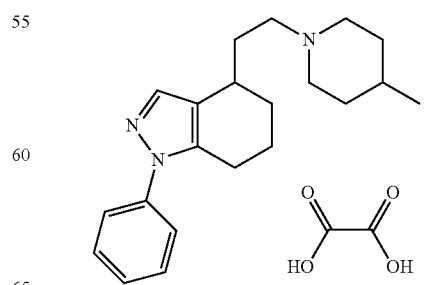

(55 mg, 0.13 mmol, 33%, p.f.=201-203° C., beige solid)

Example 95

1,4,5,6-tetrahydro-1-phenyl-4-(2-(piperidin-1-yl)ethyl)cyclopenta[c]pyrazole oxalate (95)

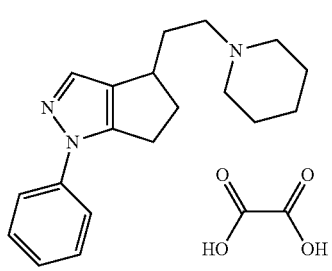 [SMILES: c1ccc(-n2ncc3c2CCC3CCN2CCCCC2)cc1 ; O=C(O)C(=O)O]

(75 mg, 0.19 mmol, 68%, p.f.=166-169° C., beige solid)

Example 96

1,4,5,6-tetrahydro-1-phenyl-4-[2-(thiomorpholin-4-yl)ethyl]cyclopenta[c]pyrazole (96)

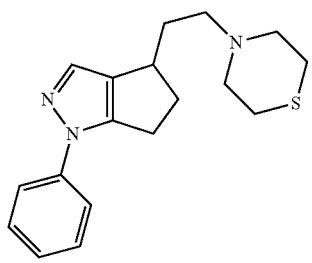 [SMILES: c1ccc(-n2ncc3c2CCC3CCN2CCSCC2)cc1]

$^1$H RMN (300 MHz, CDCl$_3$): δ 1.77 (m, 2H), 2.23 (m, 1H), 2.54 (m, 2H), 2.65-2.90 (m, 9H), 3.01 (m, 3H), 7.24 (m, 1H), 7.37 (s, 1H), 7.42 (m, 2H), 7.62 (d, J=8.5 Hz, 2H).

(71 mg, 0.23 mmol, 56%, oil)

Example 97

1,4,5,6-tetrahydro-1-phenyl-4-[2-(thiomorpholin-4-yl)ethyl]cyclopenta[c]pyrazole oxalate (97)

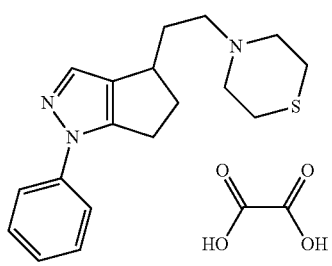 [SMILES: c1ccc(-n2ncc3c2CCC3CCN2CCSCC2)cc1 ; O=C(O)C(=O)O]

(48 mg, 0.12 mmol, 52%, p.f.=168-172° C., greyish solid)

Example 98

1,4,5,6-tetrahydro-4-(2-(4-methylpiperidin-1-yl)ethyl)-1-phenylcyclopenta[c]pyrazole (98)

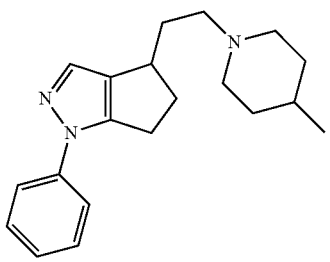

$^1$H RMN (300 MHz, CDCl$_3$): δ 0.93 (d, J=5.9 Hz, 3H), 1.35 (m, 3H), 1.65 (m, 2H), 1.80 (m, 2H), 1.99 (m, 2H), 2.24 (m, 1H), 2.49 (m, 2H), 2.80 (m, 1H), 3.01 (m, 5H), 7.23 (m, 1H), 7.38 (s, 1H), 7.42 (m, 2H), 7.62 (d, J=8.2 Hz, 2H).

(58 mg, 0.19 mmol, 46%, p.f.=78-82° C., beige solid).

Example 99

1,4,5,6-tetrahydro-4-(2-(4-methylpiperidin-1-yl)ethyl)-1-phenylcyclopenta[c]pyrazole oxalate (99)

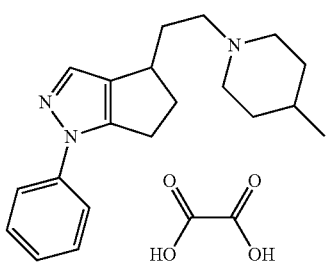

(45 mg, 0.11 mmol, 58%, p.f.=198-206° C., greyish solid)

Example 100

1,4,5,6-tetrahydro-4-(2-(4-methylpiperazin-1-yl)ethyl)-1-phenylcyclopenta[c]pyrazole (100)

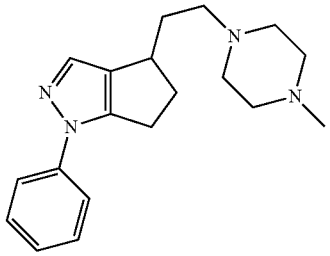 [SMILES: CN1CCN(CCC2CCc3c2cnn3-c2ccccc2)CC1]

$^1$H RMN (300 MHz, CDCl$_3$): δ 1.76 (m, 2H), 2.25 (m, 1H), 2.30 (s, 3H), 2.38-2.70 (m, 10H), 2.80 (m, 1H), 3.01 (m, 3H), 7.23 (m, 1H), 7.38 (s, 1H), 7.42 (m, 2H), 7.72 (d, J=7.6 Hz, 2H).

(30 mg, 0.10 mmol, 24%, p.f.=80-86° C., beige solid)

Example 101

4-(2-(4-cyclohexylpiperazin-1-yl)ethyl)-1,4,5,6-tetrahydro-1-phenylcyclopenta[c]pyrazole (101)

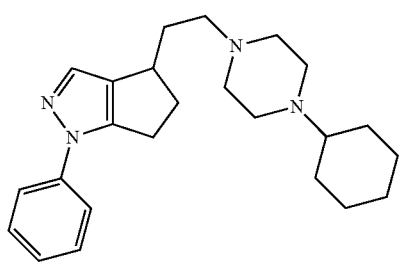 [SMILES: c1ccc(-n2ncc3c2CCC3CCN2CCN(C3CCCCC3)CC2)cc1]

$^1$H RMN (300 MHz, CDCl$_3$): δ 1.06-1.30 (m, 5H), 1.58-1.98 (m, 7H), 2.24 (m, 2H), 2.40-2.85 (m, 11H), 3.00 (m, 3H), 7.23 (m, 1H), 7.38 (s, 1H), 7.42 (m, 2H), 7.63 (m, 2H).

(35 mg, 0.09 mmol, 22%, p.f.=81-84° C., beige solid)

Example 102

Synthesis of 4-(2-(azepan-1-yl)ethyl)-4,5,6,7-tetrahydro-1-phenyl-1H-indazole (102)

Method F

Step 1: Synthesis of 2-(4,5,6,7-tetrahydro-1-phenyl-1H-indazol-4-yl)acetic acid

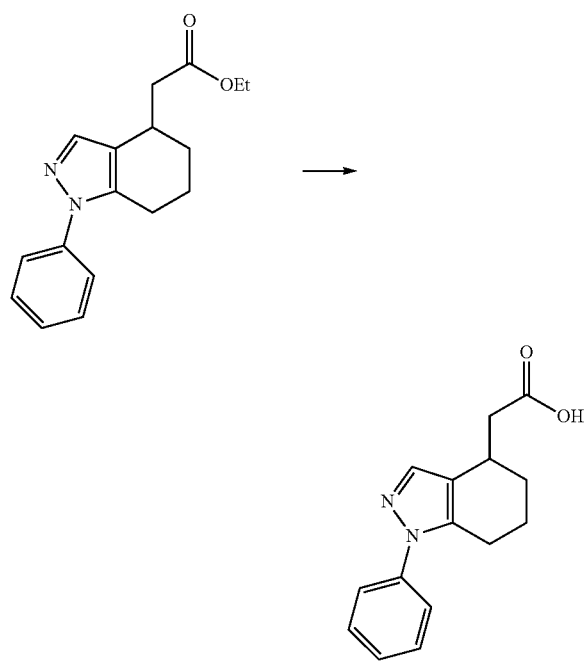

LiOH.H$_2$O (120 mg, 2.85 mmol), dissolved in 1 ml of water, is added to a solution of ethyl 2-(4,5,6,7-tetrahydro-1-phenyl-1H-indazol-4-yl)acetate (808 mg, 2.85 mmol) in methanol (20 mL) and is stirred at room temperature for 1 hour following the reaction by means of TLC. The methanol is evaporated under reduced pressure, the residue is suspended in water and acidified with diluted HCl forming a pulp that is extracted with ethyl acetate. The organic phase is washed with water, dried and evaporated at reduced pressure, giving 2-(4,5,6,7-tetrahydro-1-phenyl-1H-indazol-4-yl)acetic acid (410 mg, 1.59 mmol, 53%, solid).

$^1$H NMR (300 MHz, CDCl$_3$): δ 1.51 (m, 1H), 1.76 (m, 1H), 1.85-2.11 (m, 2H), 2.51 (dd, J=15.7 Hz, J'=8.1 Hz, 1H), 2.65-2.80 (m, 3H), 3.27 (m, 1H), 7.34 (m, 1H), 7.47 (m, 4H), 7.60 (s, 1H).

Step 2: Synthesis of 1-(2-(4,5,6,7-tetrahydro-1-phenyl-1H-indazol-4-yl)acetyl)azepane

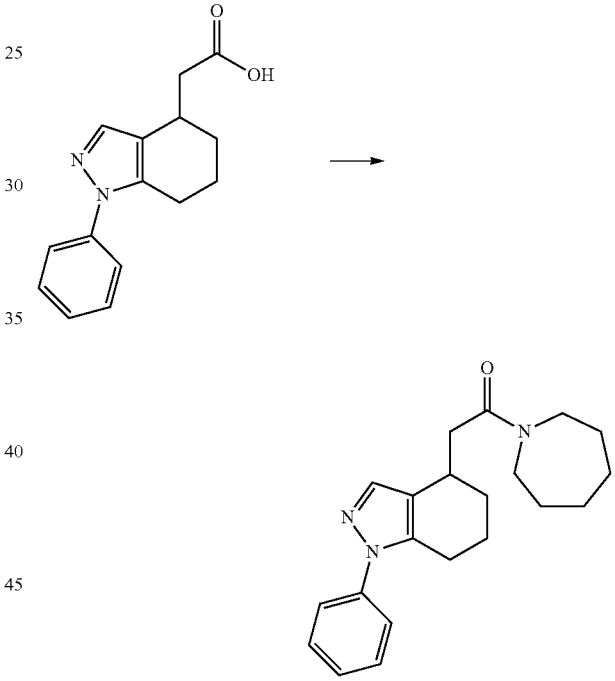

CDI (63.2 mg, 0.39 mmol) is added to a solution of 2-(4,5,6,7-tetrahydro-1-phenyl-1H-indazol-4-yl)acetic acid (100 mg, 0.39 mmol) in CH$_2$Cl$_2$ (20 mL) cooled in an ice bath, and is heated to 45° C. for 2.5 hours. Then it is cooled to 0° C. and azacycloheptane (38.7 mg, 0.39 mmol) is added and is heated at 45° C. for 1 hour. The solvent is evaporated under reduced pressure, diluted in AcOEt and washed with diluted HCl. The organic phase is dried and evaporated under reduced pressure. The resulting crude product is purified by means of silica gel chromatography, giving 1-(2-(4,5,6,7-tetrahydro-1-phenyl-1H-indazol-4-yl)acetyl)azepane (45 mg, 0.13 mmol, 33%, oil).

$^1$H NMR (300 MHz, CDCl$_3$): δ 1.45 (m, 1H), 1.52-1.81 (m, 9H), 1.92 (m, 1H), 2.08 (m, 1H), 2.47 (dd, J=15.2 Hz, J'=7.6 Hz, 1H), 2.61-2.75 (m, 3H), 3.42 (m, 3H), 3.59 (m, 2H), 7.34 (m, 1H), 7.46 (m, 4H), 7.57 (s, 1H).

Step 3: Synthesis of 4-(2-(azepan-1-yl)ethyl)-4,5,6,7-tetrahydro-1-phenyl-1H-indazole

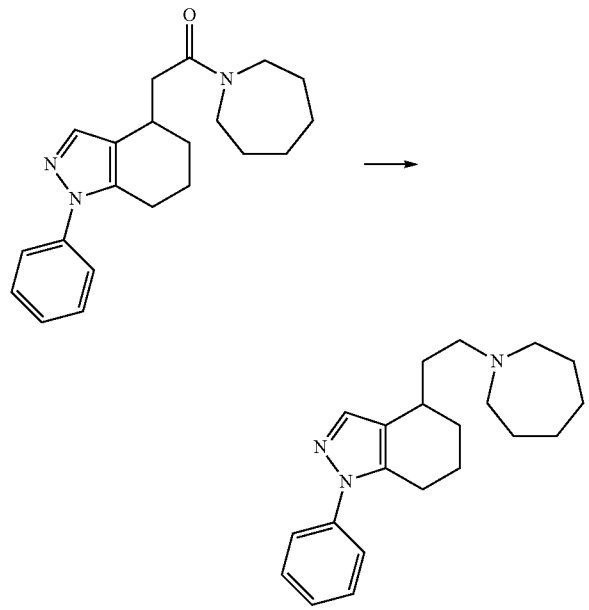

A solution of 1-(2-(4,5,6,7-tetrahydro-1-phenyl-1H-indazol-4-yl)acetyl)azepane (60 mg, 0.18 mmol) in anhydrous THF (2 mL) is slowly added to a suspension of LiAlH$_4$ (20 mg, 0.53 mmol) in anhydrous THF (10 mL) cooled to 0° C. The mixture is refluxed for 3 hours following the reaction by means of TLC. The mixture is cooled, and water and a NaOH solution are added, the precipitate is filtered and washed with AcOEt. The organic phase is separated and washed with water and dried, giving 4-(2-(azepan-1-yl)ethyl)-4,5,6,7-tetrahydro-1-phenyl-1H-indazole (36 mg, 0.11 mmol, 63%, oil).

$^1$H NMR (300 MHz, CDCl$_3$): δ 1.60-2.05 (m, 14H), 2.60-2.92 (m, 9H), 7.30 (m, 1H), 7.40-7.50 (m, 4H), 7.53 (s, 1H).

Example 103

N-benzyl-2-(1-tert-butyl-4,5,6,7-tetrahydro-1H-indazol-4-yl)-N-methylethanamine (103)

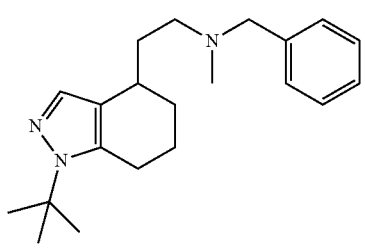 [SMILES: CN(CCC1CCCc2c1cnn2C(C)(C)C)Cc1ccccc1]

$^1$H RMN (300 MHz, CDCl$_3$): δ 1.29 (m, 1H), 1.50-2.05 (m, 14H, (δ=1.60, s, 9H)), 2.26 (br s, 3H), 2.45-2.90 (m, 5H), 3.59 (m, 2H), 7.20-7.43 (m, 6H).

Example 104

1-tert-butyl-4,5,6,7-tetrahydro-4-(2-(4-phenylpiperidin-1-yl)ethyl)-1H-indazole (104)

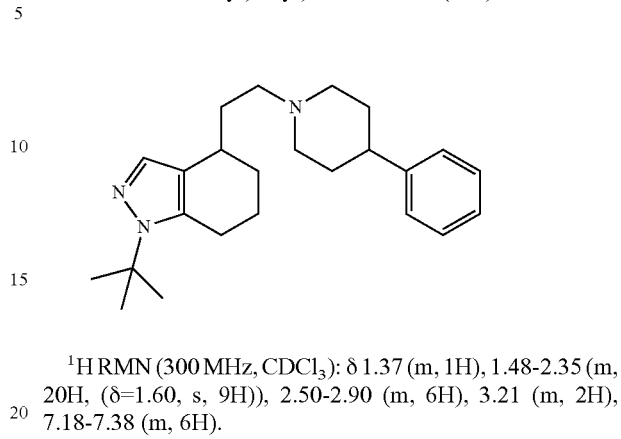

$^1$H RMN (300 MHz, CDCl$_3$): δ 1.37 (m, 1H), 1.48-2.35 (m, 20H, (δ=1.60, s, 9H)), 2.50-2.90 (m, 6H), 3.21 (m, 2H), 7.18-7.38 (m, 6H).

Example 105

1-tert-butyl-4,5,6,7-tetrahydro-4-(2-(4-phenylpiperidin-1-yl)ethyl)-1H-indazole oxalate (105)

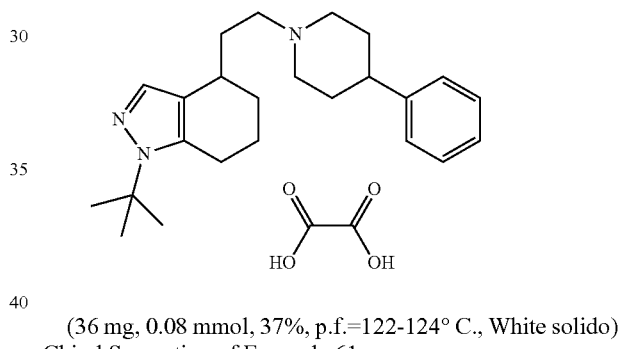

(36 mg, 0.08 mmol, 37%, p.f.=122-124° C., White solido)

Chiral Separation of Example 61

Chiral separation of the racemic N-benzyl-2-(4,5,6,7-tetrahydro-1-methyl-1H-indazol-4-yl)-N-methylethanamine (61) (257 mg) is carried out by quiral semipreparative HPLC, using a Chiralpak AD-H, 5 μm t.p., 25*2 cm Daicel column. The mobile phase employed is n-hexane/ethanol/diethylamine (90/10/0.2, v/v/v) at a flow of 17 ml/min.

Data of the Compounds:

1st peak: retention time=9.7 min. (compound 106)

Example 106

(−)-N-bencyl-2-(4,5,6,7-tetrahydro-1-methyl-1H-indazol-4-yl)-N-methylethanamine 97.1 mg, oil, [alpha]$_D^{20}$-9.1 (c=1, MeOH), ee (enantiomeric excess)>99.9%.

2nd peak: retention time=12.9 min. (compound 107)

Example 107

(+)-N-bencyl-2-(4,5,6,7-tetrahydro-1-methyl-1H-indazol-4-yl)-N-methylethanamine 96.9 mg, oil, [alpha]$_D^{20}$+8.2 (c=1, MeOH), ee (enantiomeric excess)>99.9%.

Example 108

N-(2-(4,5,6,7-tetrahydro-1-methyl-1H-indazol-4-yl)ethyl)-N-methylcyclohexanamine (108)

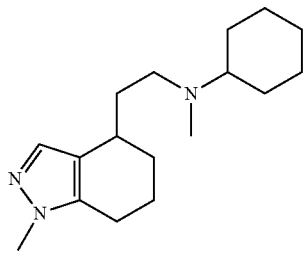 [SMILES: CN(CCC1CCCc2c1cnn2C)C1CCCCC1]

$^1$H RMN (300 MHz, CDCl$_3$): δ 1.03-1.40 (m, 6H), 1.55-2.03 (m, 10H), 2.34 (s, 3H), 2.43-2.58 (m, 3H), 2.60-2.73 (m, 3H), 3.71 (s, 3H), 7.28 (s, 1H).

(155 mg, 0.56 mmol, 77%, oil).

Example 109

4,5,6,7-tetrahydro-4-(2-(4-hydroxy-4-phenylpiperidin-1-yl)ethyl)-1-methyl-1H-indazole (109)

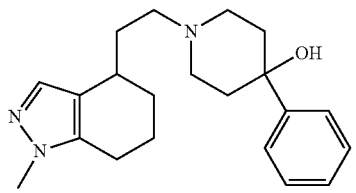 [SMILES: Cn1ncc2c1CCCC2CCN1CCC(O)(c2ccccc2)CC1]

$^1$H RMN (300 MHz, CDCl$_3$): δ 1.40 (m, 1H), 1.50-2.10 (m, 9H), 2.40-3.20 (m, 9H), 3.71 (s, 3H), 7.28 (m, 2H), 7.36 (m, 2H), 7.52 (m, 2H).

(44 mg, 0.13 mmol, 18%, p.f.=130-135° C., orange solid)

Example 110

4,5,6,7-tetrahydro-1-methyl-4-(2-(4-phenylpiperidin-1-yl)ethyl)-1H-indazole (110)

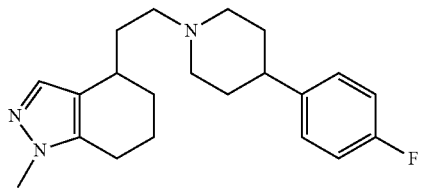 [SMILES: Cn1ncc2c1CCCC2CCN1CCC(c2ccc(F)cc2)CC1]

$^1$H RMN (300 MHz, CDCl$_3$): δ 1.37 (m, 1H), 1.60-2.20 (m, 11H), 2.54 (m, 5H), 2.67 (m, 1H), 3.10 (m, 2H), 3.72 (s, 3H), 6.97 (m, 2H), 7.18 (m, 2H), 7.30 (s, 1H).

(135 mg, 0.40 mmol, 54%, p.f.=47-54° C., orange color)

Example (111)

N-benzyl-2-(4,5,6,7-tetrahydro-1-methyl-1H-indazol-4-yl)-N-methylethanamine (111)

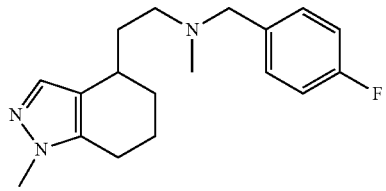 [SMILES: CN(CCC1CCCc2c1cnn2C)Cc1ccc(F)cc1]

$^1$H RMN (300 MHz, CDCl$_3$): δ 1.30 (m, 1H), 1.50-2.02 (m, 5H), 2.27 (br s, 3H), 2.40-2.72 (m, 5H), 3.56 (m, 2H), 3.71 (s, 3H), 7.02 (t, J=8.6 Hz, 2H), 7.23 (s, 1H), 7.34 (m, 2H).

(68 mg, 0.23 mmol, 31%, oil)

Example 112

4,5,6,7-tetrahydro-1-methyl-4-(2-[spiro[isobenzofuran-1(3H), 4'-piperidin]-1'-yl]-ethyl)-1H-indazole (112)

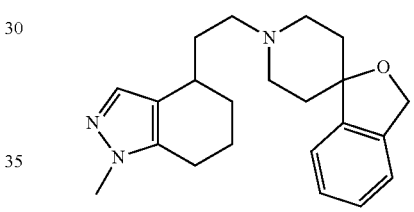

$^1$H RMN (300 MHz, CDCl$_3$): δ 1.38 (m, 1H), 1.42-2.10 (m, 9H), 2.40-2.80 (m, 7H), 3.04 (m, 2H), 3.72 (s, 3H), 5.07 (s, 2H), 7.17-7.37 (m, 5H).

(154 mg, 0.44 mmol, 60%, p.f.=95-100° C., beige solid)

Biological Activity Examples

Some representative compounds of the invention were tested for their activity as sigma (sigma-1 and sigma-2) inhibitors. The following protocols were followed:

Sigma-1

Brain membrane preparation and binding assays for the σ1-receptor were performed as described (DeHaven-Hudkins et al., 1992) with some modifications. In brief, guinea pig brains were homogenized in 10 vols. (w/v) of Tris-HCl 50 mM 0.32 M sucrose, pH 7.4, with a Kinematica Polytron PT 3000 at 15000 r.p.m. for 30 s. The homogenate was centrifuged at 1000 g for 10 min at 4° C. and the supernatants collected and centrifuged again at 48000 g for 15 min at 4° C. The pellet was resuspended in 10 volumes of Tris-HCl buffer (50 mM, pH 7.4), incubated at 37° C. for 30 min, and centrifuged at 48000 g for 20 min at 4° C. Following this, the pellet was resuspended in fresh Tris-HCl buffer (50 mM, pH 7.4) and stored on ice until use.

Each assay tube contained 10 µL of [$^3$H](+)-pentazocine (final concentration of 0.5 nM), 900 µL of the tissue suspension to a final assay volume of 1 mL and a final tissue concentration of approximately 30 mg tissue net weight/mL.

Non-specific binding was defined by addition of a final concentration of 1 µM haloperidol. All tubes were incubated at 37° C. for 150 min before termination of the reaction by rapid filtration over Schleicher & Schuell GF 3362 glass fibre filters [previously soaked in a solution of 0.5% polyethylenimine for at least 1 h]. Filters were then washed with four times with 4 mL of cold Tris-HCl buffer (50 mM, pH 7.4). Following addition of scintillation cocktail, the samples were allowed to equilibrate overnight. The amount of bound radioactivity was determined by liquid scintillation spectrometry using a Wallac Winspectral 1414 liquid scintillation counter. Protein concentrations were determined by the method of Lowry et al. (1951).

REFERENCES

DeHaven-Hudkins, D. L., L. C. Fleissner, and F. Y. Ford-Rice, 1992, Characterization of the binding of [$^3$H](+)pentazocine to a recognition sites in guinea pig brain, *Eur. J. Pharmacol.* 227, 371-378.

Lowry, O. H., N. J. Rosebrough, A. L. Farr, and R. J. Randall, 1951, Protein measurement with the Folin phenol reagent, *J. Biol. Chem.*, 193, 265.

Sigma-2

Binding studies for σ2-receptor were performed as described (Radesca et al., 1991) with some modifications. In brief, brains from sigma receptor type I (sigma-1) knockout mice were homogenized in a volume of 10 mL/g tissue net weight of ice-cold 10 mM Tris-HCl, pH 7.4, containing 320 mM sucrose (Tris-sucrose buffer) with a Potter-Elvehjem homogenizer (10 strokes at 500 r.p.m.) The homogenates were then centrifuged at 1000 g for 10 min at 4° C., and the supernatants were saved. The pellets were resuspended by vortexing in 2 mL/g ice-cold Tris-sucrose buffer and centrifuged again at 1000 g for 10 min. The combined 1000 g supernatants were centrifuged at 31000 g for 15 min at 4° C. The pellets were resuspended by vortexing in 3 mL/g 10 mM Tris-HCl, pH 7.4, and the suspension was kept at 25° C. for 15 min. Following centrifugation at 31000 g for 15 min, the pellets were resuspended by gentle Potter Elvehjem homogenization to a volume of 1.53 mL/g in 10 mM Tris-HCl pH 7.4.

The assay tubes contained 10 µL of [$^3$H]-DTG (final concentration of 3 nM), 400 µL of the tissue suspension (5.3 mL/g in 50 mM Tris-HCl, pH 8.0) to a final assay volume of 0.5 mL. Non-specific binding was defined by addition of a final concentration of 1 µM haloperidol. All tubes were incubated at 25° C. for 120 min before termination of the reaction by rapid filtration over Schleicher & Schuell GF 3362 glass fibre filters [previously soaked in a solution of 0.5% polyethylenimine for at least 1 h]. Filters were washed with three times with 5 mL volumes of cold Tris-HCl buffer (10 mM, pH 8.0). Following addition of scintillation cocktail samples were allowed to equilibrate overnight. The amount of bound radioactivity was determined by liquid scintillation spectrometry using a Wallac Winspectral 1414 liquid scintillation counter. Protein concentrations were determined by the method of Lowry et al. (1951).

REFERENCES

Radesca, L., W. D. Bowen, and L. Di Paolo, B. R. de Costa, 1991, Synthesis and Receptor Binding of Enantiomeric N-Substituted cis-N-[2-(3,4-Dichlorophenyl)ethyl]-2-(1-pyrrolidinyl)ciclohexylamines as High-Affinity a Receptor Ligands, *J. Med. Chem.* 34, 3065-3074.

Langa, F., Codony X., Tovar V., Lavado A., Giménez E., Cozar P., Cantero M., Dordal A., Hernández E., Përez R., Monroy X., Zamanillo D., Guitart X., Montoliu Ll., 2003, Generation and phenotypic análisis of sigma receptor type I (Sigma1) knockout mice, *European Journal of Neuroscience*, Vol. 18, 2188-2196.

Lowry, O. H., N. J. Rosebrough, A. L. Farr, and R. J. Randall, 1951, Protein measurement with the Folin phenol reagent, *J. Biol. Chem.*, 193, 265.

The results are summarized in the following table I:

TABLE I

| compound no. | binding sigma-1 (*) | binding sigma-1 Ki (nM) | binding sigma-2 (*) | binding sigma-2 Ki (nM) |
| --- | --- | --- | --- | --- |
| 1 | 99 | 2.8 | 74 | 474 |
| 4 | 100 | 10.6 | 98 | 316 |
| 5 | 94 | 37.2 | 39 | |
| 7 | 100 | 4.3 | 98.1 | |
| 9 | 101 | 1.5 | 107 | 37.5 |
| 10 | 100.1 | 6.1 | 70.2 | |
| 12 | 100 | 0.9 | 98.8 | 37 |
| 14 | 99.8 | 2.3 | 89 | |
| 16 | 99.9 | 1.5 | 93 | |
| 17 | 100 | 2.5 | 83.8 | 186 |
| 19 | 100.1 | 4.9 | 91 | 479.4 |
| 23 | 99.4 | 23.3 | 67.4 | |
| 24 | 100.4 | 1.1 | 102.6 | 49.5 |
| 27 | 99.6 | 7.5 | 77 | |
| 31 | 101.1 | 1.2 | 88.7 | 17.5 |
| 35 | 101 | 9.3 | 26.4 | |
| 36 | 102.8 | 5.9 | 87.9 | |
| 37 | 102 | 1.1 | 79.9 | |
| 40 | 101 | 3.5 | 97.3 | |
| 44 | 106 | 2.0 | 99.4 | 159 |
| 45 | 76.4 | 143.4 | 22.8 | |
| 47 | 103.8 | 1.8 | 95.9 | |
| 49 | 101.3 | 7.6 | 94.6 | |
| 51 | 106.6 | 31.3 | 113 | |
| 52 | 105.8 | 3.9 | 104 | |
| 54 | 105.1 | 8.7 | 100 | |
| 56 | 105.5 | 0.3 | 108.9 | 1.4 |
| 58 | 105.6 | 1.1 | 100.4 | 6.3 |
| 60 | 103.6 | 3.1 | 88.2 | 18.8 |
| 62 | 103.7 | 11.1 | 93.5 | 11.9 |
| 66 | 98.1 | 2.4 | | |
| 68 | 98 | 14.9 | 99.8 | 35.2 |
| 69 | 102.7 | 2.6 | 99.3 | 21.7 |
| 70 | 100 | 16.2 | 107.9 | 14.4 |
| 74 | 99.4 | 13.4 | 79 | |
| 76 | 102.2 | 1.3 | 60.2 | |
| 94 | 102.9 | 1.9 | | |
| 97 | 101.9 | 0.62 | | |
| 99 | 102.1 | 1.5 | | |

(*) % of radioactively labeled compound replaced by the tested compopund at 10-6 M.

Effect on Capsaicin in Development of Mechanical Allodynia

This model uses the von-Frey Filaments and is a model to test the effects or symptoms of neuropathic pain, allodynia etc.

Interest of the model:

The injection of 1 µg of capsaicin to experimental animals produces acute pain followed by hyperalgesia/allodynia The mechanisms involved in capsaicin-induced acute pain and hyperalgesia are relatively well known (mainly activation of peripheral nociceptors and sensitization of spinal cord neurons, respectively)

FIG. 1 shows the test protocol for all tests with von Frey filaments. After habituation mice were according to FIG. 1 first treated with the test-compound (or solvent in controls). Then 1 capsaicin (1% DMSO) is injected into their paw resulting in developing pain in the effected paw. The effected paw is then treated with a mechanical stimulus and the latency time before the paw is withdrawn is measured.

Using this pharmacological test the compounds according to example 2, 58, 62 and 77 showed a clear antiallodynic effect. With a dosage of 32 mg/kg at least 50% pain relieve was achieved, while the compound according to example 58 as the most potent reached 100% analgesia with 2 mg/kg.

The effect of all these 4 tested compounds could be reversed by applying 40 mg/kg PRE084 (a well-known Sigma Agonist), assuring that the observed effect was due to the sigma binding.

Effect on Carrageenan in Development of Thermal Hyperalgesia

Some compounds were also evaluated for antinociceptive activity in the carrageenan-induced thermal hyperalgesia model in mice. In this model, two hours after carrageenan injection into the paw, the plantar test was used to assess thermal hyperalgesia according to the method described by Hargreaves et al. (1988). The compounds of Examples 58 and 62.

Figure 2:
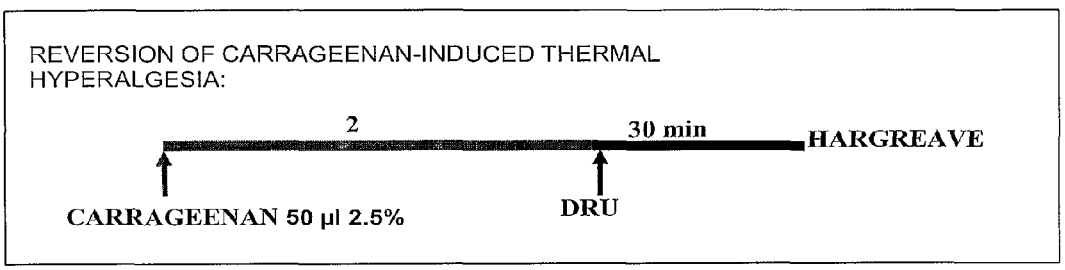
FIG. 2 shows the test protocol for all tests showing that the differences lie in the use of Carrageenan instead of Capsaicin and of Hargreaves measurements instead of von Frey filaments.

FIG. 2 shows the test protocol for all tests, showing that the differences lie in the use of Carrageenan instead of Capsaicin and of Hargreaves measurements instead of von Frey filaments.

Both compounds were highly active in this model, with the compound according to example 58 showing nearly 90% analgesia with 10 mg/kg and 60% with 2.5 mg/kg. The compound according to example 62 showed 90% analgesia with 40 mg/kg, 75% with 10 mg/kg and 40% with 2.5 mg/kg.

The effect of both compounds could be reversed by applying 40 mg/kg PRE084.

Sciatic Nerve

In addition, significant inhibition of mechanical allodynia was also evidenced for the compound according to example 62 at 30 mg/kg s.c. in the partial sciatic nerve ligation model (Seltzer et al., 1990) of neuropathic pain in mice. The von Frey test was used to assess mechanical allodynia 11-13 days after surgery.

REFERENCES

Hargreaves K, Dubner R, Brown F, Flores C, Joris J. "A new and sensitive method for measuring thermal nociception in cutaneous hyperalgesia." *Pain* 1988; 32:77-88.

Seltzer Z, Dubner R, Shir Y. "A novel behavioral model of neuropathic pain disorders produced in rats by partial sciatic nerve injury." *Pain* 1990; 43:205-218.

The invention claimed is:

1. A method of treating pain, comprising administering to a patient a therapeutically effective amount of a compound of formula I:

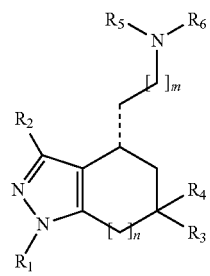

wherein
$R_1$ is selected from the group formed by hydrogen, substituted or unsubstituted alkyl, substituted or unsubstituted cycloalkyl, substituted or unsubstituted heterocyclyl, substituted or unsubstituted aryl, substituted or unsubstituted arylalkyl, and substituted or unsubstituted heterocyclylalkyl;

$R_2$ is selected from the group formed by hydrogen, substituted or unsubstituted alkyl, substituted or unsubstituted cycloalkyl, substituted or unsubstituted alkoxy, substituted or unsubstituted aryl, substituted or unsubstituted heterocyclyl, substituted or unsubstituted arylalkyl, and substituted or unsubstituted heterocyclylalkyl;

$R_3$ and $R_4$ are independently selected from the group formed by hydrogen, substituted or unsubstituted alkyl, substituted or unsubstituted cycloalkyl, substituted or unsubstituted heterocyclyl, substituted or unsubstituted aryl, substituted or unsubstituted arylalkyl and substituted or unsubstituted heterocyclylalkyl or, together, $R_3$ and $R_4$ form a 3 to 6 substituted or unsubstituted member ring;

$R_5$ and $R_6$ are independently selected from the group formed by hydrogen, substituted or unsubstituted alkyl, substituted or unsubstituted cycloalkyl, substituted or unsubstituted heterocyclyl, substituted or unsubstituted aryl, substituted or unsubstituted arylalkyl and substituted or unsubstituted heterocyclylalkyl or, $R_5$ and $R_6$ together, form a substituted or unsubstituted heterocyclyl having 3 to 7 atoms in the ring;

n is selected from 0, 1 and 2;
m is selected from 0, 1, 2, 3, 4;
the dotted line ------ is either a single or a double bond;
with the proviso that when $R_1$ is phenyl, $R_2$ is H, the dotted line ------ is a double bond, m is 1, and $R_5$ and $R_6$ form a 2,5-dioxopyrrolidine or a 5-ethoxy-2-oxopyrrolidine, then $R_3$ and $R_4$ are not both at the same time H or methyl; or a pharmaceutically acceptable salt, stereoisomer, ester, phosphate ester, metal salts sulfonate ester, carbamate, or amide thereof.

2. The method according to claim 1 wherein the pain is neuropathic pain, inflammatory pain or other pain conditions involving allodynia and/or hyperalgesia.

3. The method according to claim 1, wherein in the compound of formula (I) $R_2$ is hydrogen or alkyl.

4. The method according to claim 1, wherein in the compound of formula (I) m is 1 or 2.

5. The method according to claim 1, wherein in the compound of formula (I) n is 0 or 1.

6. The method according to claim 1, wherein in the compound of formula (I) $R_3$ and $R_4$ are both hydrogen or alkyl.

7. The method according to claim 1, wherein in the compound of formula (I) $R_1$ is selected from the group formed by substituted or unsubstituted alkyl, substituted or unsubstituted cycloalkyl, substituted or unsubstituted heterocyclyl and substituted or unsubstituted aryl.

8. The method according to claim 1, wherein in the compound of formula (I) $R_5$ and $R_6$ together form a substituted or unsubstituted heterocyclyl having 3 to 7 atoms in the ring.

9. The method according to claim 1, wherein the compound of formula (I) is:
4,5,6,7-tetrahydro-4-(2-(morpholin-4-yl)ethyl)-1-phenyl-1H-indazole,
4,5,6,7-tetrahydro-4-(2-(morpholin-4-yl)ethyl)-1-phenyl-1H-indazole oxalate,
1-(3,4-dichlorophenyl)-4,5,6,7-tetrahydro-4-(2-(4-phenylpiperidin-1-yl)ethyl)-1H-indazole,
1-(3,4-dichlorophenyl)-4,5,6,7-tetrahydro-4-(2-(4-phenylpiperidin-1-yl)ethyl)-1H-indazole oxalate, (E)-4,5,6,7-tetrahydro-4-(2-(morpholin-4-yl)ethylidene)-1-phenyl-1H-indazole,
1-(3,4-dichlorophenyl)-4,5,6,7-tetrahydro-4-(2-(morpholin-4-yl)ethyl)-1H-indazole,
1-(3,4-dichlorophenyl)-4,5,6,7-tetrahydro-4-(2-(morpholin-4-yl)ethyl)-1H-indazole oxalate,
4,5,6,7-tetrahydro-1-phenyl-4-(2-(4-phenylpiperidin-1-yl)ethyl)-1H-indazole,
4,5,6,7-tetrahydro-1-phenyl-4-(2-(4-phenylpiperidin-1-yl)ethyl)-1H-indazole oxalate,
4-(2-(4-benzylpiperazin-1-yl)ethyl)-4,5,6,7-tetrahydro-1-phenyl-1H-indazole,
4,5,6,7-tetrahydro-1-phenyl-4-(2-[spiro[isobenzofuran-1(3H), 4'-piperidin]-1'-yl]ethyl)-1H-indazole,
4,5,6,7-tetrahydro-1-phenyl-4-(2-[spiro[isobenzofuran-1(3H), 4'-piperidin]-1'-yl]ethyl)-1H-indazole oxalate,
4,5,6,7-tetrahydro-1-phenyl-4-(2-(piperidin-1-yl)ethyl)-1H-indazole,
4,5,6,7-tetrahydro-1-phenyl-4-(2-(piperidin-1-yl)ethyl)-1H-indazole oxalate,
(E)-4-(2-(azepan-1-yl)ethylidene)-4,5,6,7-tetrahydro-1-phenyl-1H-indazole,
(E)-4-(2-(azepan-1-yl)ethylidene)-4,5,6,7-tetrahydro-1-phenyl-1H-indazole oxalate,
(E)-4,5,6,7-tetrahydro-1-phenyl-4-(2-(4-phenylpiperidin-1-yl)ethylidene)-1H-indazole,
(E)-4,5,6,7-tetrahydro-1-phenyl-4-(2-[spiro[isobenzofuran-1(3H), 4'-piperidin]-1'-yl]ethylidene)-1H-indazole,
(E)-4,5,6,7-tetrahydro-1-phenyl-4-(2-[spiro[isobenzofuran-1(3H), 4'-piperidin]-1'-yl]ethylidene)-1H-indazole oxalate,
(E)-4,5,6,7-tetrahydro-1-phenyl-4-(2-(4-phenylpiperazin-1-yl)ethylidene)-1H-indazole,
1,2,3,4-tetrahydro-2-((E)-2-(6,7-dihydro-1-phenyl-1H-indazol-4(5H)-ylidene)ethyl)isoquinoline,
1,2,3,4-tetrahydro-2-((E)-2-(6,7-dihydro-1-phenyl-1H-indazol-4(5H)-ylidene)ethyl)isoquinoline oxalate,
(E)-4,5,6,7-tetrahydro-1-phenyl-4-(2-(3-phenylpiperidin-1-yl)ethylidene)-1H-indazole,
(E)-4,5,6,7-tetrahydro-1-phenyl-4-(2-(3-phenylpyrrolidin-1-yl)ethylidene)-1H-indazole
(E)-4,5,6,7-tetrahydro-1-phenyl-4-(2-(3-phenylpyrrolidin-1-yl)ethylidene)-1H-indazole oxalate,
(E)-4,5,6,7-tetrahydro-1-phenyl-4-(2-(isoindolin-2-yl)ethylidene)-1-phenyl-1H-indazole,
(E)-4,5,6,7-tetrahydro-1-phenyl-4-(2-(piperidin-1-yl)ethylidene)-1H-indazole,
1-(3,4-dichlorophenyl)-4,5,6,7-tetrahydro-4-(2-(4-phenylpiperazin-1-yl)ethyl)-1H-indazole,
1-(3,4-dichlorophenyl)-4,5,6,7-tetrahydro-4-(2-(4-phenylpiperazin-1-yl)ethyl)-1H-indazole oxalate,
1,4,5,6-tetrahydro-4-(2-(morpholin-4-yl)ethyl)-1-phenylcyclopenta[c]pyrazole,
1,4,5,6-tetrahydro-4-(2-(morpholin-4-yl)ethyl)-1-phenylcyclopenta[c]pyrazole oxalate,
4,5,6,7-tetrahydro-1-phenyl-4-(2-(4-phenylpiperazin-1-yl)ethyl)-1H-indazole,
4,5,6,7-tetrahydro-1-phenyl-4-(2-(4-phenylpiperazin-1-yl)ethyl)-1H-indazole oxalate,
2-(2-(1,4,5,6-tetrahydro-1-phenylcyclopenta[c]pyrazol-4-yl)ethyl)isoindoline,
2-(2-(1,4,5,6-tetrahydro-1-phenylcyclopenta[c]pyrazol-4-yl)ethyl)isoindoline oxalate,
1,4,5,6-tetrahydro-1-phenyl-4-(2-(4-phenylpiperidin-1-yl)ethyl)cyclopenta[c]pyrazole,
1,4,5,6-tetrahydro-1-phenyl-4-(2-(piperidin-1-yl)ethyl)cyclopenta[c]pyrazole,
1,4,5,6-tetrahydro-1-phenyl-4-(2-(4-phenylpiperazin-1-yl)ethyl)cyclopenta[c]pyrazole,
1,4,5,6-tetrahydro-1-phenyl-4-(2-(pyrrolidin-1-yl)ethyl)cyclopenta[c]pyrazole,
1,4,5,6-tetrahydro-1-phenyl-4-(2-(pyrrolidin-1-yl)ethyl)cyclopenta[c]pyrazole oxalate,
4-(2-(4-benzylpiperazin-1-yl)ethyl)-1,4,5,6-tetrahydro-1-phenylcyclopenta[c]pyrazole,
4-(2-(4-benzylpiperazin-1-yl)ethyl)-1,4,5,6-tetrahydro-1-phenylcyclopenta[c]pyrazole dioxalate,
1,2,3,4-tetrahydro-2-(2-(1,4,5,6-tetrahydro-1-phenylcyclopenta[c]pyrazol-4-yl)ethyl)isoquinoline,
1,2,3,4-tetrahydro-2-(2-(1,4,5,6-tetrahydro-1-phenylcyclopenta[c]pyrazol-4-yl)ethyl)isoquinoline oxalate,
4-(2-(1H-imidazol-1-yl)ethyl)-1,4,5,6-tetrahydro-1-phenylcyclopenta[c]pyrazole,
cis-1,4,5,6-tetrahydro-4-(2-(2,6-dimethylmorpholin-4-yl)ethyl)-1-phenylcyclopenta[c]pyrazole,
cis-1,4,5,6-tetrahydro-4-(2-(2,6-dimethylmorpholin-4-yl)ethyl)-1-phenylcyclopenta[c]pyrazole oxalate,
cis-4,5,6,7-tetrahydro-4-(2-(2,6-dimethylmorpholin-4-yl)ethyl)-1-phenyl-1H-indazole,
cis-4,5,6,7-tetrahydro-4-(2-(2,6-dimethylmorpholin-4-yl)ethyl)-1-phenyl-1H-indazole oxalate,
1,4,5,6-tetrahydro-1-phenyl-4-(2-[spiro[isobenzofuran-1(3H),4'-piperidin]-1'-yl]-ethyl)cyclopenta[c]pyrazole,
1,4,5,6-tetrahydro-1-phenyl-4-(2-[spiro[isobenzofuran-1(3H),4'-piperidin]-1'-yl]-ethyl)cyclopenta[c]pyrazole oxalate,
N-benzyl-2-(1,4,5,6-tetrahydro-1-phenylcyclopenta[c]pyrazol-4-yl)-N-methyl-ethanamine, diastereomeric mixture of 1,4,5,6-tetrahydro-1-phenyl-4-(2-(3-phenylpiperidin-1-yl)ethyl)cyclopenta[c]pyrazole,
N-benzyl-2-(4,5,6,7-tetrahydro-1-phenyl-1H-indazol-4-yl)-N-methylethanamine,
4,5,6,7-tetrahydro-4-(2-(isoindolin-2-yl)ethyl)-1-phenyl-1H-indazole,
4,5,6,7-tetrahydro-4-(2-(isoindolin-2-yl)ethyl)-1-phenyl-1H-indazole oxalate,
4,5,6,7-tetrahydro-1-methyl-4-(2-(4-phenylpiperidin-1-yl)ethyl)-1H-indazole,
4,5,6,7-tetrahydro-1-methyl-4-(2-(4-phenylpiperidin-1-yl)ethyl)-1H-indazole oxalate,
4,5,6,7-tetrahydro-4-(2-(isoindolin-2-yl)ethyl)-1-methyl-1H-indazole,
4,5,6,7-tetrahydro-4-(2-(isoindolin-2-yl)ethyl)-1-methyl-1H-indazole oxalate,
N-benzyl-2-(4,5,6,7-tetrahydro-1-methyl-1H-indazol-4-yl)-N-methylethanamine,
N-benzyl-2-(4,5,6,7-tetrahydro-1-methyl-1H-indazol-4-yl)-N-methylethanamine oxalate,
4,5,6,7-tetrahydro-1-methyl-4-(2-(morpholin-4-yl)ethyl)-1H-indazole,
4,5,6,7-tetrahydro-1-methyl-4-(2-(morpholin-4-yl)ethyl)-1H-indazole oxalate,
1-(4-fluorophenyl)-4,5,6,7-tetrahydro-4-(2-(morpholin-4-yl)ethyl)-1H-indazole,
1-(4-fluorophenyl)-4,5,6,7-tetrahydro-4-(2-(morpholin-4-yl)ethyl)-1H-indazole oxalate,
cis-1-(4-fluorophenyl)-4,5,6,7-tetrahydro-4-(2-(2,6-dimethylmorpholin-4-yl)ethyl)-1H-indazole,
cis-1-(4-fluorophenyl)-4,5,6,7-tetrahydro-4-(2-(2,6-dimethylmorpholin-4-yl)ethyl)-1H-indazole oxalate,
N-benzyl-2-(1-(4-fluorophenyl)-4,5,6,7-tetrahydro-1H-indazol-4-yl)-N-methyl-ethanamine,
1-(4-fluorophenyl)-4,5,6,7-tetrahydro-4-(2-(isoindolin-2-yl)ethyl)-1H-indazole, 1-(4-fluorophenyl)-4,5,6,7-tetrahydro-4-(2-(isoindolin-2-yl)ethyl)-1H-indazole oxalate,
1-(4-fluorophenyl)-4,5,6,7-tetrahydro-4-(2-(4-phenylpiperidin-1-yl)ethyl)-1H-indazole,
(+)-4,5,6,7-tetrahydro-4-(2-(morpholin-4-yl)ethyl)-1-phenyl-1H-indazole,
(+)-4,5,6,7-tetrahydro-4-(2-(morpholin-4-yl)ethyl)-1-phenyl-1H-indazole oxalate,
(+4,5,6,7-tetrahydro-4-(2-(morpholin-4-yl)ethyl)-1-phenyl-1H-indazole,
(+4,5,6,7-tetrahydro-4-(2-(morpholin-4-yl)ethyl)-1-phenyl-1H-indazole oxalate,
(E)-4,5,6,7-tetrahydro-4-(2-(morpholin-4-yl)ethylidene)-1-phenyl-1H-indazole, oxalate,
(E)-4,5,6,7-tetrahydro-1-phenyl-4-(2-(piperidin-1-yl)ethylidene)-1H-indazole oxalate,
(E)-N-benzyl-2-(6,7-dihydro-1-phenyl-1H-indazol-4(5H)-ylidene)-N-methyl-ethanamine,
(E)-N-benzyl-2-(6,7-dihydro-1-phenyl-1H-indazol-4(5H)-ylidene)-N-methyl-ethanamine oxalate,
(E)-4,5,6,7-tetrahydro-4-(2-(cis-2,6-dimethylmorpholin-4-yl)ethylidene)-1-phenyl-1H-indazole,
(E)-4,5,6,7-tetrahydro-4-(2-(cis-2,6-dimethylmorpholin-4-yl)ethylidene)-1-phenyl-1H-indazole oxalate,
(E)-1-(3,4-dichlorophenyl)-4,5,6,7-tetrahydro-4-(2-(cis-2,6-dimethylmorpholino-4-yl)-ethylidene)-1H-indazole,
(E)-1-(3,4-dichlorophenyl)-4,5,6,7-tetrahydro-4-(2-(cis-2,6-dimethyl-morpholino-4-yl)-ethylidene)-1H-indazole oxalate,
(E)-1-(3,4-dichlorophenyl)-4,5,6,7-tetrahydro-4-(2-(morpholino-4-yl)ethylidene)-1H-indazole,
(E)-1-(3,4-dichlorophenyl)-4,5,6,7-tetrahydro-4-(2-(morpholino-4-yl)-ethylidene)-1H-indazole oxalate,
(E)-1-(3,4-dichlorophenyl)-4,5,6,7-tetrahydro-4-(2-(piperidin-1-yl)ethylidene)-1H-indazole,
(E)-1-(3,4-dichlorophenyl)-4,5,6,7-tetrahydro-4-(2-(piperidin-1-yl)-ethylidene)-1H-indazole oxalate,
(E)-4-(2-(N,N-diethylamino)ethylidene)-4,5,6,7-tetrahydro-1-phenyl-1H-indazole,
(E)-4-(2-(N,N-diethylamino)ethylidene)-4,5,6,7-tetrahydro-1-phenyl-1H-indazole oxalate,
(E)-4-(2-(4-cyclohexylpiperazin-1-yl)ethylidene)-4,5,6,7-tetrahydro-1-phenyl-1H-indazole,
(E)-4,5,6,7-tetrahydro-4-(2-(4-methylpiperidin-1-yl)ethylidene)-1-phenyl-1H-indazole,
4,5,6,7-tetrahydro-4-(2-(4-methylpiperidin-1-yl)ethyl)-1-phenyl-1H-indazole,
4,5,6,7-tetrahydro-4-(2-(4-methylpiperidin-1-yl)ethyl)-1-phenyl-1H-indazole oxalate,
1,4,5,6-tetrahydro-1-phenyl-4-(2-(piperidin-1-yl)ethyl)cyclopenta[c]pyrazole oxalate,
1,4,5,6-tetrahydro-1-phenyl-4-[2-(thiomorpholin-4-yl)ethyl]cyclopenta[c]pyrazole,
1,4,5,6-tetrahydro-1-phenyl-4-[2-(thiomorpholin-4-yl)ethyl]cyclopenta[c]pyrazole oxalate,
1,4,5,6-tetrahydro-4-(2-(4-methylpiperidin-1-yl)ethyl)-1-phenylcyclopenta[c]pyrazole,
1,4,5,6-tetrahydro-4-(2-(4-methylpiperidin-1-yl)ethyl)-1-phenylcyclopenta[c]pyrazole oxalate,
1,4,5,6-tetrahydro-4-(2-(4-methylpiperazin-1-yl)ethyl)-1-phenylcyclopenta[c]pyrazole,
4-(2-(4-cyclohexylpiperazin-1-yl)ethyl)-1,4,5,6-tetrahydro-1-phenylcyclopenta[c]pyrazole,
4-(2-(azepan-1-yl)ethyl)-4,5,6,7-tetrahydro-1-phenyl-1H-indazole,
N-benzyl-2-(1-tert-butyl-4,5,6,7-tetrahydro-1H-indazol-4-yl)-N-methylethanamine,
1-tert-butyl-4,5,6,7-tetrahydro-4-(2-(4-phenylpiperidin-1-yl)ethyl)-1H-indazole,
1-tert-butyl-4,5,6,7-tetrahydro-4-(2-(4-phenylpiperidin-1-yl)ethyl)-1H-indazole oxalate,
(−)-N-bencyl-2-(4,5,6,7-tetrahydro-1-methyl-1H-indazol-4-yl)-N-methylethanamine,
(+)-N-bencyl-2-(4,5,6,7-tetrahydro-1-methyl-1H-indazol-4-yl)-N-methylethanamine,
N-(2-(4,5,6,7-tetrahydro-1-methyl-1H-indazol-4-yl)ethyl)-N-methylcyclohexanamine,
4,5,6,7-tetrahydro-4-(2-(4-hydroxy-4-phenylpiperidin-1-yl)ethyl)-1-methyl-1H-indazole,
4,5,6,7-tetrahydro-1-methyl-4-(2-(4-phenylpiperidin-1-yl)ethyl)-1H-indazole,
N-benzyl-2-(4,5,6,7-tetrahydro-1-methyl-1H-indazol-4-yl)-N-methylethanamine,
4,5,6,7-tetrahydro-1-methyl-4-(2-[spiro[isobenzofuran-1(3H),4'-piperidin]-1'-yl]-ethyl)-1H-indazole,
or any pharmaceutically acceptable salt thereof.

10. The method according to claim 6, wherein in the compound of formula (I) $R_3$ and $R_4$ are both hydrogen or methyl.

11. The method according to claim 10, wherein in the compound of formula (I) $R_3$ and $R_4$ are both hydrogen.

12. The method according to claim 8, wherein in the compound of formula (I) the heterocyclyl formed by $R_5$ and $R_6$ is selected from the group formed by a morpholin-4-yl, 2,6-dimethylmorpholin-4-yl, piperidin-1-yl, 4-phenylpiperidin-1-yl, 3-phenylpiperidin-1-yl, 4-benzylpiperazin-1-yl, 4-phenyl-piperazin-1-yl, 2-[spiro[isobenzofuran-1(3H), 4'-piperidin]-1'-yl, azepan-1-yl, pyrrolidin-1-yl, 3-phenylpyrrolidin-1-yl, and imidazol-1-yl.

* * * * *